US010570182B2

(12) United States Patent
Sheets et al.

(10) Patent No.: US 10,570,182 B2
(45) Date of Patent: Feb. 25, 2020

(54) MODIFIED CRY1CA TOXINS USEFUL FOR CONTROL OF INSECT PESTS

(71) Applicant: DOW AGROSCIENCES LLC, Indianapolis, IN (US)

(72) Inventors: Joel J. Sheets, San Luis Obispo, CA (US); Kenneth Narva, Indianapolis, IN (US); Thomas Meade, Zionsville, IN (US); Timothy D. Hey, Zionsville, IN (US); Sek Yee Tan, Indianapolis, IN (US); Audrey Jane Etter, Indianapolis, IN (US); Todd P. Glancy, Fairmount, IN (US); Janna Mai Armstrong, Indianapolis, IN (US); Tristan E. Coram, Indianapolis, IN (US); Krishna M. Madduri, Indianapolis, IN (US); James E. King, Carmel, IN (US); Ryan M. Lee, Indianapolis, IN (US); Gaofeng Lin, Zionsville, IN (US); Jianquan Li, Cary, NC (US)

(73) Assignee: DOW AGROSCIENCES LLCIN (US)

( * ) Notice: Subject to any disclaimer, the term of this patent is extended or adjusted under 35 U.S.C. 154(b) by 0 days.

(21) Appl. No.: 15/541,303

(22) PCT Filed: Dec. 16, 2015

(86) PCT No.: PCT/US2015/066182

§ 371 (c)(1),
(2) Date: Jun. 30, 2017

(87) PCT Pub. No.: WO2016/109212

PCT Pub. Date: Jul. 7, 2016

(65) Prior Publication Data

US 2017/0369539 A1 Dec. 28, 2017

Related U.S. Application Data

(60) Provisional application No. 62/097,833, filed on Dec. 30, 2014.

(51) Int. Cl.

| | |
|---|---|
| ***C12N 15/82*** | (2006.01) |
| ***C07K 14/325*** | (2006.01) |
| ***A01N 63/02*** | (2006.01) |
| ***A01N 37/46*** | (2006.01) |

(52) U.S. Cl.
CPC ............ *C07K 14/325* (2013.01); *A01N 37/46* (2013.01); *A01N 63/02* (2013.01); *C12N 15/8286* (2013.01); *Y02A 40/162* (2018.01)

(58) Field of Classification Search
None
See application file for complete search history.

(56) References Cited

FOREIGN PATENT DOCUMENTS

| | | |
|---|---|---|
| WO | 2011075588 | 6/2011 |
| WO | 2011084627 | 7/2011 |
| WO | WO2011/084629 A1 * | 7/2011 |
| WO | WO2013/116758 A1 * | 8/2013 |
| WO | 2014055881 | 4/2014 |

OTHER PUBLICATIONS

Zaidi et al, Mol Biotechnol 43:232-42 (2009).*
Maagd et al., Appl. Environ Microbial 65:4369-4374 (1999).*
Tounsi et al., J. Appl. Microbial. 95:23-28, 27 (2003).*
Angsuthanasombat et al., J Biochem Mol Biol 34:402-407 (2001).*
Aronson & Shai, FEMS Microbial. Lett. 195:1-8 (2001).*
De Maagd et al., Trends Genet. 17:193-99 (2001).*
IB/373—International Preliminary Report on Patentability Chapter 1, International Application No. PCT/US2015/066182.
ISA/237—Written Opinion of the International Searching Authority, International Application No. PCT/US2015/066182, dated May 20, 2016.
ISA/201—International Search Report, International Application No. PCT/US2015/066182, dated May 20, 2016.
Maagd et al, Role of Bacillus thuringiensis Toxin Domains in Toxicity and Receptor Binding in the Diamondback Moth; Applied and Envorinmental Microbiology, vol. 65, No. 5; p. 1900-1903; May 1999.

* cited by examiner

*Primary Examiner* — Russell T Boggs

(57) ABSTRACT

The subject invention concerns *Bacillus thuringiensis* modified Cry1Ca insecticidal toxins and the polynucleotide sequences which encode these toxins. Uses in transgenic plants are described as are methods for protecting crops from insect pest damage.

26 Claims, 3 Drawing Sheets

Specification includes a Sequence Listing.

MODIFIED CRY1CA TOXINS USEFUL FOR CONTROL OF INSECT PESTS

CROSS-REFERENCE TO RELATED APPLICATIONS

This application is a national stage entry under 35 USC § 371(b) of PCT International Application No. PCT/US2015/066182, filed Dec. 16, 2015, and claims the benefit of and priority to U.S. Provisional Application Ser. No. 62/097,833 filed Dec. 30, 2014. Each of these applications is expressly incorporated herein by reference.

FIELD OF THE DISCLOSURE

The subject invention concerns modification of a *Bacillus thuringiensis* pesticidal toxin, the polynucleotide sequences which encode these toxins and transgenic plants that produce these toxins.

BACKGROUND OF DISCLOSURE

Insects and other pests cost farmers billions of dollars annually in crop losses and expense to keep these pests under control. In addition to losses in field crops, insect pests are also a burden to vegetable and fruit growers, to producers of ornamental flowers, and to home gardeners. The losses caused by insect pests in agricultural production environments include decrease in crop yield, reduced crop quality, and increased harvesting costs.

Insect pests are mainly controlled by intensive applications of chemical pesticides, which are active through inhibition of insect growth, prevention of insect feeding or reproduction, or cause death. Good insect control can thus be reached, but these chemicals can sometimes affect other beneficial insects. Another problem resulting from the wide use of chemical pesticides is the appearance of resistant insect populations. This has been partially alleviated by various resistance management practices, but there is an increasing need for alternative pest control agents. Biological pest control agents, such as *Bacillus thuringiensis* (B.t.) strains expressing pesticidal toxins like delta-endotoxins, have also been applied to crop plants with satisfactory results, offering an alternative or compliment to chemical pesticides. The genes coding for some of these delta-endotoxins have been isolated and their expression in heterologous hosts have been shown to provide another tool for the control of economically important insect pests. In particular, the expression of insecticidal toxins, such as *Bacillus thuringiensis* delta-endotoxins, in transgenic plants have provided efficient protection against selected insect pests, and transgenic plants expressing such toxins have been commercialized, allowing farmers to reduce applications of chemical insect control agents.

Lepidopterans are an important group of agricultural, horticultural, and household pests which cause a large amount of damage each year. This insect order encompasses foliar- and root-feeding larvae and adults. Lepidopteran insect pests include, but are not limited to: *Achoroia grisella, Acleris gloverana, Acleris variana, Adoxophyes orana, Agrotis ipsilon* (black cutworm "BCW"), *Alabama argillacea, Alsophila pometaria, Amyelois transitella, Anagasta kuehniella, Anarsia lineatella, Anisota senatoria, Antheraea pernyi, Anticarsia gemmatalis* (velvetbean caterpillar "VBC"), *Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmia feneralis, Diaphania hyalinata, Diaphania nitidalis, Diatraea grandiosella* (southwestern corn borer "SWCB"), *Diatraea saccharalis, Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea* (corn earworm "CEW"), *Heliothis virescens* (tobacco budworm "TBW"), *Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis* (European corn borer "ECB"), *Paleacrita vernata, Papiapema nebris* (common stalk borer), *Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella* (diamondback moth "DBM"), *Pontia protodice, Pseudaletia unipuncta, Pseudoplusia includens* (soybean looper "SBL"), *Sabulodes aegrotata, Schizura concinna, Sitotroga cerealella, Spilonta ocellana, Spodoptera eridania* (southern armyworm "SAW"), *Spodoptera frugiperda* (fall armyworm "FAW"), *Spodoptera exigua* (beet armyworm "BAW"), *Thaurnstopoea pityocampa, Ensola bisselliella, Trichoplusia ni* (cabbage looper "CL"), *Udea rubigalis, Xylomyges curiails*, and *Yponomeuta padella*. Any genus listed above (and others), generally, can also be targeted as a part of the subject invention. Any additional insects in any of these genera (as targets) are also included within the scope of this invention.

*Bacillus thuringiensis* (B.t.) is a soil-borne, Gram-positive, spore forming bacterium that produces insecticidal crystal proteins known as delta endotoxins or Cry proteins (reviewed in Schnepf et al., 1998). Novel Crystal (Cry) proteins with new insecticidal properties continue to be discovered at an increasing rate, and over 440 Cry genes have been reported. Currently, there are over 450 unique Cry and Cytotoxin (Cyt) proteins classified among 57 primary homology ranks. Cry proteins are named based on the degree of sequence identity, with primary, secondary and tertiary boundaries occurring at approximately 45%, 78% and 95% identity, respectively; close alleles are assigned new quaternary designations (Crickmore et al., 1998). An expansive list of delta endotoxins is maintained and regularly updated at lifesci.sussex.ac.uk/home/Neil_Crickmore/Bt/intro.html. There are currently over 73 main groups of "Cry" toxins (Cry1-Cry73), with additional Cyt toxins and Vegetative Insecticidal Protein (VIP) toxins and the like. Many of each numeric group have capital-letter subgroups, and the capital letter subgroups have lower-cased letter sub-subgroups. (Cry1 has A-L, and Cry1A has a-i, for example).

B.t. proteins have been used to create the insect-resistant transgenic plants that have been successfully registered or deregulated and commercialized to date. These include Cry1Ab, Cry1Ac, Cry1F, Vip3A, Cry34Ab1/Cry35Ab1, and Cry3Bb in corn, Cry1Ac, Vip3A and Cry2Ab in cotton, and Cry3A in potato. B.t. toxins represent over 90% of the bioinsecticide market and essentially the entire source of genes for transgenic crops that have been developed to provide resistance to insect feeding.

Cry proteins are oral intoxicants that function by acting on midgut cells of susceptible insects. The active forms of many Cry proteins comprise three distinct protein domains. The most well studied B.t. proteins are members of the three-domain Cry delta-endotoxins. These proteins range in size from approximately 70 kDa to 130 kDa. Primary protein sequence analysis reveals five highly conserved sequence blocks and a high degree of sequence variability between conserved blocks three and five (Schnepf et al., 1998).

Three dimensional crystal structures have been determined for Cry1Aa1, Cry2Aa1, Cry3Aa1, Cry3Bb1, Cry4Aa, Cry4Ba and Cry8Ea1 as examples. These structures are remarkably similar and are comprised of three distinct domains with the following features (reviewed in de Maagd et al., 2003). Domain I is a bundle of seven alpha helices where helix five is surrounded by six amphipathic helices. This domain has been implicated in midgut membrane insertion and pore formation. It shares homology with other pore forming proteins including hemolysins and colicins. Domain II is comprised of three anti-parallel beta sheets packed together in a beta prism. This domain shares homology with certain carbohydrate-binding proteins including vitelline and jacaline. The loops of this domain play important roles in binding insect midgut receptors. In Cry1A proteins, surface exposed loops at the apices of domain II beta sheets are involved in binding to lepidopteran cadherin receptors. Domain III is a beta sandwich structure that interacts with a second class of receptors, examples of which are aminopeptidase and alkaline phosphatase in the case of Cry1A proteins (Piggot and Ellar, 2007). Structurally this domain is related to carbohydrate-binding domains of proteins such as glucanases, galactose oxidase, sialidase and others. This domain binds certain classes of receptor proteins and perhaps participates in insertion of an oligomeric toxin pre-pore. Conserved B.t. sequence blocks 2 and 3 map near the N-terminus and C-terminus of domain 2, respectively. Hence, these conserved sequence blocks 2 and 3 are approximate boundary regions between the three functional domains. These regions of conserved DNA and protein homology have been exploited for engineering recombinant B.t. toxins (U.S. Pat. No. 6,090,931, WO 91/01087, WO95/06730, WO 1998022595).

One proposed model for Cry protein mode of action is based on pore formation in the midgut membranes of susceptible insects (Knowles and Ellar, 1987). In the current version of this model (Bravo et al., 2007), binding to both cadherin and aminopeptidase receptors on Lepidopteran midgut membranes are required for Cry protein toxicity. According to the pore formation model, Cry protein intoxication involves several steps: 1) Proteolytic processing of soluble Cry protoxin to an activated core toxin; 2) Cry protein binding to cadherin receptors on the insect midgut; 3) further proteolytic cleavage at the core toxin N-terminus to remove an α-helical region; 4) Cry protein oligomerization to form a pre-pore; 5) pre-pore binding to second site membrane receptors (aminopeptidases and alkaline phosphatases); 6) pre-pore insertion into the membrane and 7) osmotic cell lysis leading to midgut disruption and insect death.

The widespread adoption of insect-resistant transgenic plant technology gives rise to a concern that pest populations will develop resistance to the insecticidal proteins produced by these plants. Several strategies have been suggested for preserving the utility of B.t.-based insect resistance traits which include deploying proteins at a high dose in combination with a refuge, and alternation with, or co-deployment of, different toxins (McGaughey et al. (1998), "B.t. Resistance Management," Nature Biotechnol. 16:144-146).

The development of insect resistance to B.t. Cry proteins can result through several mechanisms (Heckel et al., 2007, Piggot and Ellar, 2007). Multiple receptor protein classes for Cry proteins have been identified within insects, and multiple examples exist within each receptor class. Resistance to a particular Cry protein may develop, for example, by means of a mutation within the toxin-binding portion of a cadherin domain of a receptor protein. A further means of resistance may be mediated through a protoxin-processing protease. Thus, resistance to Cry1A toxins in species of *Lepidoptera* has a complex genetic basis, with at least four distinct, major resistance genes. Lepidopteran insects resistant to Cry proteins have developed in the field for *Plutella xylostella* (Tabashnik, 1994), *Trichoplusia ni* (Janmaat and Myers 2003, 2005), *Helicoverpa zea* (Tabashnik et al., 2008), and *Spodoptera frupperda* (Storer, et al., 2010). Development of new high potency Cry proteins will provide additional tools for management of Lepidopteran insect pests.

This invention provides B.t. insecticidal proteins that are effective in controlling insects that are resistant to Cry1Ac and Cry1F. These protein toxins may be used advantageously to protect agronomic crops from insect feeding damage. The ability to express these insect toxins in such a manner that sufficient quantity of the functionally active protein is present in a crop of interest is also a subject of this invention.

BRIEF SUMMARY OF THE INVENTION

A modified Cry1Ca toxin comprising residues 2 to 68 of SEQ ID NO:2 wherein amino acid residue 54 is chosen from the group consisting of Gly and Ala, amino acid residue 57 is chosen from the group consisting of Leu and Met, and amino acid residue 68 is chosen from the group consisting of Val, Phe, and Ile. A modified Cry1Ca toxin comprising residues 2 to 628 of SEQ ID NO: 10 wherein amino acid residue 54 is chosen from the group consisting of Gly and Ala, amino acid residue 57 is chosen from the group consisting of Leu and Met, amino acid residue 68 is chosen from the group consisting of Val, Phe, and Be, amino acid residue 73 is chosen from the group consisting of Trp, Ala and Met, amino acid residue 596 is chosen from the group consisting of Phe, Met and Ala, and amino acid residue 620 is chosen from the group consisting of Leu and Phe. The modified Cry1Ca toxins of the foregoing further comprising a carboxy terminal extension consisting of amino acid residues 629 to 1164 of SEQ ID NO:36. The modified Cry1Ca toxins of the foregoing further comprising a carboxy terminal extension consisting of amino acid residues 629 to 1164 of SEQ ID NO:36. The modified Cry1Ca toxins of the foregoing further comprising an amino terminal extension consisting of amino acid residues 1 to 74 of SEQ ID NO:40. The modified Cry1Ca toxins of the foregoing further comprising an amino terminal extension consisting of amino acid residues 1 to 74 of SEQ ID NO:40.

DNA encoding modified Cry1Ca toxins, transgenic plants producing modified Cry1Ca toxins and methods of controlling insect pests using the modified Cry1Ca toxins are included in the invention.

The subject invention concerns novel materials and methods for controlling arthropod pests that are detrimental to plants and to agriculture. In a preferred embodiment, the subject invention provides materials and methods for the control of Lepidopteran pests.

Specific B.t. Cry proteins (endotoxins, toxins) useful according to the invention include toxins which can be obtained from the B.t. isolate designated as MR-1206. The subject invention also includes the use of mutants of the exemplified B.t. isolate and toxins which have improved Lepidopteran-active properties, that resist protease processing, or express at high levels when the genes are transformed into a heterologous expression system. Procedures for making mutants are well known in the microbiological art. Ultraviolet light and chemical mutagens such as nitrosoguanidine are used extensively toward this end.

The subject protein toxins can be "applied" or provided to contact the target insects in a variety of ways. For example, transgenic plants (wherein the protein is produced by and present in the plant) can be used and are well-known in the art. Expression of the toxin genes can also be achieved selectively in specific tissues of the plants, such as the roots, leaves, etc. This can be accomplished via the use of tissue-specific promoters, for example. Spray-on applications are another example and are also known in the art. The subject proteins can be appropriately formulated for the desired end use, and then sprayed (or otherwise applied) onto the plant and/or around the plant and/or to the vicinity of the plant to be protected, before an infestation is discovered, after target insects are discovered, both before and after, and the like. The subject protein can also be appropriately formulated and applied to the seeds as a seed treatment that allows the protein to be in contact with the root area of the plant to protect it from root feeding insects. Bait granules, for example, can also be used and are known in the art.

The subject proteins can be used to protect practically any type of plant from damage by a Lepidopteran insect. Examples of such plants include maize, sunflower, soybean, cotton, canola, rice, sorghum, wheat, barley, vegetables, ornamentals, peppers (including hot peppers), sugar beets, fruit, and turf grass, to name but a few. Especially preferred plants are maize, soybean and cotton. A most preferred plant is maize. Another most preferred plant is soybean. Another most preferred plant is cotton.

In one embodiment of the subject invention, the polynucleotide sequences of the subject invention encode toxins of approximately 68-71 kDa. These toxins are used to control Lepidopteran pests, especially fall armyworms, diamondback moths, southwestern corn borer, southern armyworm, corn earworm, and European corn borer. In a preferred embodiment, the subject invention concerns plants cells transformed with at least one polynucleotide sequence of the subject invention such that the transformed plant cells produce and contain pesticidal toxins of the invention in tissues consumed by the target pests.

Alternatively, the B.t. isolate of the subject invention, or recombinant microbes expressing genes encoding the pesticidal toxin proteins described herein, can be used to control insect pests. In this regard, the invention includes the treatment of substantially intact B.t. cells, and/or recombinant cells containing the toxins of the invention, treated to prolong the pesticidal activity when the substantially intact cells are applied to the environment of a target pest. The treated cell acts as a protective coating for the pesticidal toxin. The toxin becomes active upon ingestion by a target insect.

One aspect of the invention pertains to isolated nucleic acid molecules comprising nucleotide sequences encoding pesticidal proteins and polypeptides or biologically active portions thereof, as well as nucleic acid molecules sufficient for use as hybridization probes to identify nucleic acids encoding the claimed toxins. As used herein, the term "nucleic acid molecule" is intended to include DNA molecules (e.g. cDNA or genomic DNA) and RNA molecules (e.g. mRNA) and analogs of the DNA or RNA generated using nucleotide analogs. The nucleic acid molecule can be single-stranded or double-stranded, but preferably is double-stranded DNA.

Nucleotide sequences encoding the proteins of the present invention include the sequences set forth in SEQ ID NOs:1, 3, 5, 7, 9, 11, 13, 15, 17, 19, 21, 23, 25, 27, 29, 31, 33, 35, 37, 39, and complements thereof. By "complement" is intended a nucleotide sequence that is sufficiently complementary to a given nucleotide sequence such that it can hybridize to the given nucleotide sequence to thereby form a stable duplex (double-stranded) molecule. The corresponding amino acid sequences for the pesticidally active modified Cry1Ca toxins encoded by these nucleotide sequences are set forth in SEQ ID NOs:2, 4, 6, 8, 10, 12, 14, 16, 18, 20, 22, 24, 26, 28, 30, 32, 34, 36, 38, and 40.

Nucleic acid molecules that are fragments of the claimed toxin-encoding nucleotide sequences are also encompassed by the present invention. By "fragment" is intended a portion of the nucleotide sequence encoding a fragment of a claimed modified Cry1Ca toxin. A fragment of a nucleotide sequence may encode a biologically active portion of a claimed toxin protein, or it may be a fragment that can be used as a hybridization probe or PCR primer using methods disclosed below.

BRIEF DESCRIPTION OF THE SEQUENCES

SEQ ID NO:1 DNA sequence encoding DIG-468
SEQ ID NO:2 is the DIG-468 protein sequence
SEQ ID NO:3 DNA sequence encoding DIG-483
SEQ ID NO:4 is the DIG-483 protein sequence
SEQ ID NO:5 DNA sequence encoding DIG-485
SEQ ID NO:6 is the DIG-485 protein sequence
SEQ ID NO:7 DNA sequence encoding DIG-487
SEQ ID NO:8 is the DIG-487 protein sequence
SEQ ID NO:9 DNA sequence encoding DIG-462
SEQ ID NO:10 is the DIG-462 protein sequence
SEQ ID NO:11 DNA sequence encoding DIG-463
SEQ ID NO:12 is the DIG-463 protein sequence
SEQ ID NO:13 DNA sequence encoding DIG-464
SEQ ID NO:14 is the DIG-464 protein sequence
SEQ ID NO:15 DNA sequence encoding DIG-465
SEQ ID NO:16 is the DIG-465 protein sequence
SEQ ID NO:17 DNA sequence encoding DIG-466
SEQ ID NO:18 is the DIG-466 protein sequence
SEQ ID NO:19 DNA sequence encoding DIG-467
SEQ ID NO:20 is the DIG-467 protein sequence
SEQ ID NO:21 DNA sequence encoding DIG-469
SEQ ID NO:22 is the DIG-469 protein sequence
SEQ ID NO:23 DNA sequence encoding DIG-473
SEQ ID NO:24 is the DIG-473 protein sequence
SEQ ID NO:25 DNA sequence encoding DIG-474
SEQ ID NO:26 is the DIG-474 protein sequence
SEQ ID NO:27 DNA sequence encoding DIG-482
SEQ ID NO:28 is the DIG-482 protein sequence SEQ ID NO:29 DNA sequence encoding modified Cry1Ca codon optimized for maize (IRDIG544.11)

SEQ ID NO:30 is the modified Cry1Ca protein protein toxin sequence (IRDIG544.11)

SEQ ID NO:31 DNA sequence encoding a modified Cry1Ca, IRDIG544.12, with high GC codon optimization SEQ ID NO:32 protein toxin sequence for IRDIG544.12

SEQ ID NO:33 a dicot optimized DNA sequence encoding modified Cry1Ca, IRDIG544.9

SEQ ID NO:34 protein sequence of modified Cry1Ca, IRDIG544.9

SEQ ID NO:35 a dicot optimized DNA sequence encoding modified Cry1Ca, IRDIG544.8

SEQ ID NO:36 IRDIG544.8 protein encoded by a DNA sequence codon optimized for dicots SEQ ID NO:37 DNA sequence encoding a modified Cry1Ca toxin fused to the Cry1Ab protoxin segment SEQ ID NO:38 is the protein toxin sequence produced from the DNA of SEQ ID NO:37

SEQ ID NO:39 High GC codon optimized DNA sequence encoding a modified Cry1Ca, IRDIG544.12, fused to TraP12

SEQ ID NO:40 Is the modified Cry1Ca toxin, IRDIG544.12, fused to TraP12

DETAILED DESCRIPTION OF THE INVENTION

Figure 1:
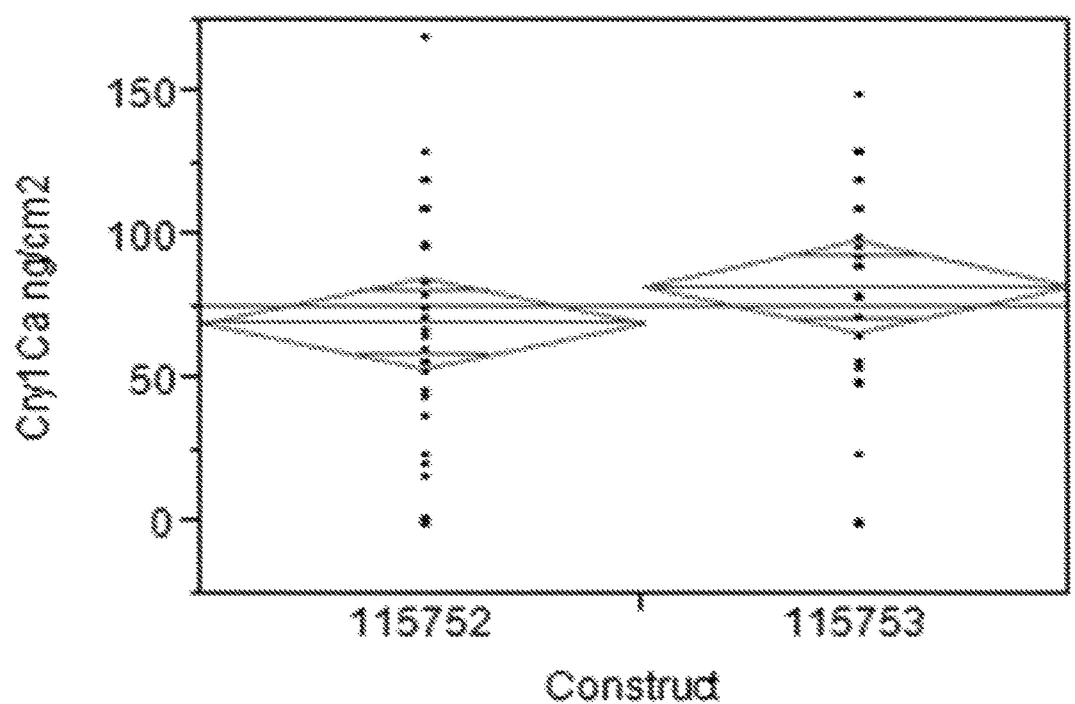
FIG. 1 shows expression levels of DIG-465 by construct 115752 and DIG-473 by construct 115753 in $T_1$ maize leaves sampled by leaf punches.

By the use of the term "genetic material" herein, it is meant to include all genes, nucleic acid, DNA and RNA. These sequences have been altered in such a manner to increase the stability of the expressed protein toxin when the gene is transformed in a plant, specifically maize and dicots. The protein toxins discussed herein are typically referred to as "insecticides" or "insecticidal". By insecticides and insecticidal it is meant herein that the protein toxins have a "functional activity" as further defined herein and are used as insect control agents.

By "functional activity" it is meant herein that the protein toxins function as insect control agents in that the proteins are orally active, or have a toxic effect, or are able to disrupt or deter feeding, which may or may not cause death of the insect. When an insect comes into contact with an effective amount of toxin delivered via transgenic plant expression, formulated protein composition(s), sprayable protein composition(s), a bait matrix or other delivery system, the results are typically death of the insect, or the insects do not feed upon the source which makes the toxins available to the insects.

By the use of the term "oligonucleotides" it is meant a macromolecule consisting of a short chain of nucleotides of either RNA or DNA. Such length could be at least one nucleotide, but typically are in the range of about 10 to about 12 nucleotides. The determination of the length of the oligonucleotide is well within the skill of an artisan and should not be a limitation herein. Therefore, oligonucleotides may be less than 10 or greater than 12. The subject invention concerns not only the polynucleotide sequences which encode these classes of toxins, but also the use of these polynucleotide sequences to produce recombinant hosts which express the toxins.

By the use of the term "toxic" or "toxicity" as used herein it is meant that the toxins produced by *Bacillus thuringiensis* have "functional activity" as defined herein.

By use of the term "modified Cry1Ca toxin(s)" it is meant to include all of the protein sequences of the Sequence Listing and all the variants thereof described herein.

By the use of the term "genetic material" herein, it is meant to include all genes, nucleic acid, DNA and RNA.

For designations of nucleotide residues of polynucleotides, DNA, RNA, oligonucleotides, and primers, and for designations of amino acid residues of proteins, standard IUPAC abbreviations are employed throughout this document. Nucleic acid sequences are presented in the standard 5' to 3' direction, and protein sequences are presented in the standard amino (N) terminal to carboxy (C) terminal direction.

The toxins and genes of the subject invention can be further defined by their amino acid and nucleotide sequences, and the sequence of unique fragments comprised by the full-length DNA and amino sequences. The sequences of the molecules within each novel class can be defined herein in terms of homology to certain exemplified sequences as well as in terms of the ability to hybridize with, or be amplified by, certain exemplified probes and primers. The classes of toxins provided herein can also be identified based on their immunoreactivity with certain antibodies.

Toxin Structure.

The toxin of the subject invention can also be characterized in terms of the structure and domain composition. The correlation of protein sequence variability with differences in bioactivity spectrum led to early hypotheses that the "hypervariable" regions between blocks three and five are responsible for differences in insect specificity among B.t. delta-endotoxins.

When the gene that encodes native full length Cry1Ca protein was inserted and expressed in maize cells, at least 5 detectable proteolytic degradation products were observed. Those five polypeptides were determined to have the following amino acid lengths: 1-1164, 1-628, 29-628, 74-628, and 74-596. Of the five Cry1Ca degradation products detected, two of the fragments were found to be inactive against the key driver insect pests. In most cases, these two inactive fragments represented a major portion of the Cry1Ca-related proteins detected in maize cells. Expressing the native, full length gene for Cry1Ca in maize resulted in plants having insufficient functional activity against key insect pests such as *S. frugiperda.*

When the gene that expresses truncated native Cry1Ca protein (aa 1-628) was inserted and expressed in maize cells, less proteolytic processing occurred. The majority remained unprocessed and functionally active. Thus expressing the truncated Cry1Ca gene in maize cells resulted in plants having sufficient functional activity against key insect pests due to reduced proteolysis in maize cells.

Altering the primary amino acid sequence of Cry1Ca allows for continual biological activity against key insect pests, and results in less proteolytic processing of the protein, as measured in vitro using chymotrypsin as the protease enzyme. Less proteolytic processing of altered Cry1Ca protein results in higher amounts of functionally active protein accumulating in plants and results in greater activity against the target insect pests.

Protease Sensitive Variants.

Insect gut proteases typically function in aiding the insect in obtaining needed amino acids from dietary protein. The best understood insect digestive proteases are serine proteases, which appear to be the most common type (Englemann and Geraerts, 1980), particularly in Lepidopteran species. Coleopteran insects have guts that are more neutral to acidic than are Lepidopteran guts. The majority of Coleopteran larvae and adults, for example Colorado potato beetle, have slightly acidic midguts, and cysteine proteases provide the major proteolytic activity (Wolfson and Murdock, 1990). More precisely, Thie and Houseman (1990) identified and characterized the cysteine proteases, cathepsin B-like and cathepsin H-like, and the aspartyl protease, cathepsin D-like, in Colorado potato beetle. Gillikin et al., (1992) characterized the proteolytic activity in the guts of western corn rootworm larvae and found primarily cysteine proteases. U.S. Pat. No. 7,230,167 disclosed that the serine protease, cathepsin G, exists in western corn rootworm. The diversity and different activity levels of the insect gut proteases may influence an insect's sensitivity to a particular B.t. toxin.

In one embodiment, the toxins have specific changes in their amino acid sequences that significantly reduce the level of protease processing of the expressed protein by proteases found naturally in maize plants. The changes in amino acids results in higher levels of functional activity of the protein when expressed in maize. Protease cleavage sites may be introduced at desired locations by chemical gene synthesis or splice overlap PCR (Horton et al., 1989). Serine protease recognition sequences, for example, can optionally be inserted at specific sites in the Cry protein structure to affect protein processing at desired deletion points within the midgut of certain insect pests. Lepidopteran midgut serine proteases such as trypsin or trypsin-like enzymes, chymotrypsin, elastase, etc. (Christeller et al., 1992) can be exploited for activation of Cry proteins by engineering protease recognition sequences at desired processing sites. Likewise, Coleopteran serine proteases such as trypsin, chymotrypsin and cathepsin G-like protease may similarly be exploited by engineering recognition sequences at desired processing sites. Further, Coleopteran cysteine proteases such as cathepsins (B-like, L-like, O-like, and K-like proteases) (Koiwa et al., 2000 and Bown et al., 2004), metalloproteases such as ADAM10 (Ochoa-Campuzano et al., 2007), and aspartic acid proteases such as cathepsins D-like and E-like, pepsin, plasmepsin, and chymosin may be exploited by engineering recognition sequences at desired processing sites.

The scope of this invention includes variant Cry1Ca insecticidal proteins that are produced by manipulating the encoding sequence for the subject insecticidal proteins by introduction or elimination of protease processing sites at appropriate positions to allow, or eliminate, proteolytic cleavage of a larger variant protein by insect, plant, or microorganism proteases. The end result of such manipulation is the generation of toxin molecules having the same or better activity as the intact (full length) native toxin protein.

Unlike the high sequence specificity associated with Type II restriction endonucleases in the recognition and cleavage of their DNA substrates, proteolytic enzymes are more nonspecific in the amino sequence comprising the cleavage recognition site. Some generalities have been discovered regarding the amino acid structures comprising some protease cleavage sites, in particular, cathepsin G as compared to cathepsins B, K, L, and S (Bown et al., 2004). In the nomenclature of protease cleavage sites in the illustrations below, the amino acid residues upstream (i.e. towards the N-terminus) from the cleavage site are numbered P1, P2, P3, P4, P5, etc, with residue P1 being immediately adjacent to the cleavage site, and residue P5 being the fifth most distal from the cleavage site in the N-terminal direction. Amino acid residues downstream (i.e. towards the C-terminus) from the cleavage site are numbered P1', P2', P3', P4', P5' etc., with residue P1' being immediately adjacent to the cleavage site, and residue P5' being the fifth most distal from the cleavage site in the C-terminal direction. Cathepsin G is known to exhibit preferential cleavage after P1 residues glutamine, lysine, tryptophan, or phenylalanine, where residues P2, P3, P4, P5, etc., and P1', P2', P3', P4' P5', etc. can be any of the 20 amino acids normally found in natural proteins. Somewhat enhanced cleavage site sequence specificity is demonstrated by cathepsins B, K, L, and S, wherein the side chain of the P2 amino acid fits into a substrate binding site S2 of the cathepsin. The S2 site of these cathepsins preferentially interacts with P2 amino acids having large hydrophobic side chains (e.g. as found in valine, leucine, isoleucine, phenylalanine, tryptophan, and tyrosine), and disfavors interaction with P2 residues having charged side chains (except that cathepsins B and L accept the large hydrophilic charged side chain of arginine in the P2 position). Some specificity is seen in the identity of the amino acid in the P3 position. For example, cathepsin L cleaves preferentially after arginine in the P1 position, when phenylalanine or arginine occupy the P2 position. The P3 amino acid can be either an aromatic type (e.g. phenylalanine, tryptophan, histidine, or tyrosine) or a hydrophobic type (e.g. alanine, valine, leucine, isoleucine, phenylalanine, tryptophan, or tyrosine). Positions P4, P5, etc. and P1', P2', P3', P4', P5', etc. can be any of the 20 amino acids normally found in natural proteins.

Proteolytic cleavage is further dependent on the availability of the subject cleavage sequence to the respective protease; sequestration of the potential cleavage site within the three-dimensional structure of the protein may render the protein resistant to cleavage by the particular protease. It is thought that the diversity and different activity levels of the insect gut proteases may influence an insect's sensitivity to a particular B.t. toxin. One skilled in the arts of biochemistry and molecular biology can examine the biochemical characteristics (including, but not limited to, determination of the sequences of the amino acids comprising the N-terminus and C-terminus of the polypeptide) of insecticidal protein fragments generated by protease cleavage/activation of larger proteins by the gut proteases of susceptible insects. One may also characterize the protease regime of the guts of nonsusceptible insects or host plants, and engineer, at appropriate places within the coding sequence for the B.t. insecticidal protein, sequences amenable to cleavage by the gut proteases of nonsusceptible insects or prospective host plants in which the B.t. insecticidal protein will be produced transgenically. Such analyses and manipulations of the subject B.t. insecticidal protein are understood to be within the scope of this invention.

In another embodiment, the toxins have specific changes in their amino acid sequences that significantly enhance the level of protein expression, when expressed in a variety of different expression systems, including plant and bacteria. The result of the increased expression of the protein is increased functional activity in the expression system. This is advantageous in providing a high dose of the toxin to the insect which can prevent the occurrence of resistance in the insects to the toxins due to survival of small populations of insects receiving a sub lethal dose of the protein toxin.

Genes and Toxins.

The protein molecules of the embodiments herein comprise amino acid sequences that are homologous to known pesticidal proteins, particularly B.t. Cry proteins, more particularly Cry1Ca protein (Genbank Accession No. AAA22343). The predicted amino acid sequences encoded by a nucleotide sequences of the embodiments are disclosed as SEQ ID NOs:2, 4, 6, 8, 10, 12, 14, 16, 18, 20, 22, 24, 26, 28, 30, 32, 34, 36, 38, and 40.

The sequence of toxins of the subject invention are provided as SEQ ID NOs:2, 4, 6, 8, 10, 12, 14, 16, 18, 20, 22, 24, 26, 28, 30, 32, 34, 36, 38, and 40. In a preferred embodiment, the toxins of the subject invention have at least one of the following characteristics:

(a) said toxin is encoded by a nucleotide sequence which hybridizes under stringent conditions with a nucleotide sequence selected from the group consisting of SEQ ID NOs:1, 3, 5, 7, 9, 11, 13, 15, 17, 19, 21, 23, 25, 27, 29, 31, 33, 35, 37, 39, or their complementary sequences.

(b) said toxin is immunoreactive with an antibody raised against an approximately 68-71 kDa pesticidal toxin, or a fragment thereof, from a *Bacillus thuringiensis* isolate.

(c) said toxin is encoded by a nucleotide sequence wherein a portion of said nucleotide sequence can be amplified by PCR using a primer pair to produce a fragment of about 25-40 bp, (d) said toxin comprises a pesticidal portion of the amino acid sequences shown in SEQ ID NOs:2, 4, 6, 8, 10, 12, 14, 16, 18, 20, 22, 24, 26, 28, 30, 32, 34, 36, 38, and 40, (e) said toxin comprises an amino acid sequence which has at least about (90%) homology with a pesticidal portion of an amino acid sequence selected from the group consisting of SEQ ID NOs:2, 4, 6, 8, 10, 12, 14, 16, 18, 20, 22, 24, 26, 28, 30, 32, 34, 36, 38, and 40, (f) said toxin is encoded by a nucleotide sequence which hybridizes under stringent conditions with an insecticidal portion of a nucleotide sequence selected from the group consisting of DNA which encodes SEQ ID NOs:2, 4, 6, 8, 10, 12, 14, 16, 18, 20, 22, 24, 26, 28, 30, 32, 34, 36, 38, and 40, (g) said toxin is immunoreactive with an antibody to an approximately 68 kDa or 130 kDa pesticidal toxin, or a fragment thereof, from a *Bacillus thuringiensis* isolate, MR-1206.

(h) said toxin comprises an amino acid sequence which has at least about (90%) homology with an amino acid sequence selected from the group consisting of SEQ ID NOs:2, 4, 6, 8, 10, 12, 14, 16, 18, 20, 22, 24, 26, 28, 30, 32, 34, 36, 38, and 40 and pesticidal portions of SEQ ID NOs:2, 4, 6, 8, 10, 12, 14, 16, 18, 20, 22, 24, 26, 28, 30, 32, 34, 36, 38, and 40.

The specific genes exemplified herein, variations of these genes, and fragments of these genes may also be obtained, for example, by synthetic construction by methods currently practiced by any of several commercial suppliers (see for example, U.S. Pat. No. 7,482,119). These genes, or portions or variants thereof, may also be constructed synthetically, for example, by use of a gene synthesizer and the methods of, for example, U.S. Pat. No. 5,380,831. Alternatively, variations of synthetic or naturally occurring genes may be readily constructed using standard molecular biological techniques for making point mutations. Fragments of these genes can also be made using commercially available exonucleases or endonucleases according to standard procedures. For example, enzymes such as Bal31 or site-directed mutagenesis can be used to systematically cut off nucleotides from the ends of these genes. Also, gene fragments which encode active toxin fragments may be obtained using a variety of restriction enzymes.

Nucleic acid molecules that are fragments of a claimed toxin-encoding nucleotide sequence comprise at least about 15, 20, 30, 40, 50, 60, 75, 100, 200, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 3000, 3500 nucleotides, or up to the number of nucleotides present in a full-length claimed insecticidal toxin-encoding nucleotide sequence disclosed herein (for example, 1,878 nucleotides for SEQ ID NO:1; 3,495 nucleotides for SEQ ID NO:37), depending upon the intended use. A fragment of a nucleotide sequence that encodes a biologically active portion of a claimed protein of the invention will encode at least about 15, 25, 30, 40, 50, 75, 100, 125, 150, 175, 200, 250, 300, 350, 400, 450, 500, 550, 600, 650, 700, 800, 900, 1000, 1100 or 1200 contiguous amino acids, or up to the total number of amino acids present in a full-length insecticidal protein of the invention (for example, 625 amino acids for SEQ ID NO:2 or 1,164 amino acids for SEQ ID NO:38).

Recombinant Hosts.

The toxin-encoding genes of the subject invention can be introduced into a wide variety of microbial or plant hosts. Expression of the toxin gene results, directly or indirectly, in the intracellular production and maintenance of the pesticidal protein. With suitable microbial hosts, e.g. *Pseudomonas*, the microbes can be applied to the environment of the pest, where they will proliferate and can be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type indigenous microorganisms, provide for stable maintenance and expression of the gene expressing the polypeptide pesticide, and, desirably, provide for improved protection of the pesticide from environmental degradation and inactivation.

B.t. spores or recombinant host cells also can be treated prior to being applied or formulated for application to plants. For example, isolated B.t. spores and/or toxin crystals can be chemically treated to prolong insecticidal activity and thereby include a treated polypeptide of the invention (U.S. Pat. No. 4,695,462 and Gaertner et al., 1993).

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g. genera *Pseudomonas, Envinia, Serratia, Klebsiella, Xanthomonas, Streptomyces, Rhizobium, Sinorhizobium, Rhodopseudomonas, Methylophilius, Agrobacterium, Acetobacter, Lactobacillus, Arthrobacter, Azotobacter, Leuconostoc*, and *Alcaligenes*; and fungi, particularly yeast, e.g. genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Agrobacterium radiobacter, Rhodopseudomonas spheroides, Xanthomonas campestris, Sinorhizobium meliloti* (formerly *Rhizobium*

*meliloti*), *Alcaligenes eutrophus*, and *Azotobacter vinelandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A preferred embodiment of the subject invention is the transformation of plants with genes encoding the subject insecticidal protein or its variants. The transformed plants are resistant to attack by an insect target pest by virtue of the presence of controlling amounts of the subject insecticidal protein or its variants in the cells of the transformed plant. By incorporating genetic material that encodes the insecticidal properties of the B.t. insecticidal toxins into the genome of a plant eaten by a particular insect pest, the adult or larvae would die after consuming the food plant. Numerous members of the monocotyledonous and dicotyledonous classifications have been transformed. Transgenic agronomic crops as well as fruits and vegetables are of commercial interest. Such crops include but are not limited to maize, rice, soybeans, canola, sunflower, alfalfa, sorghum, wheat, cotton, peanuts, tomatoes, potatoes, and the like. Several techniques exist for introducing foreign genetic material into monocot or dicot plant cells, and for obtaining fertile plants that stably maintain and express the introduced gene. Such techniques include acceleration of genetic material coated onto microparticles directly into cells (U.S. Pat. Nos. 4,945,050 and 5,141,131). Plants may be transformed using *Agrobacterium* technology, see U.S. Pat. Nos. 5,177,010, 5,104,310, European Patent Application 0131624B1, European Patent Application 120516, European Patent Application 159418B, European Patent Application 176112, U.S. Pat. Nos. 5,149,645, 5,469,976, 5,464,763, 4,940,838, 4,693,976, European Patent Application 116718, European Patent Application 290799, European Patent Application 320500, European Patent Application 604662, European Patent Application 627752, European Patent Application 0267159, European Patent Application 0292435, U.S. Pat. Nos. 5,231,019, 5,463,174, 4,762,785, 5,004,863, and 5,159,135. Other transformation technology includes WHISKERS™ technology, see U.S. Pat. Nos. 5,302,523 and 5,464,765. Electroporation technology has also been used to transform plants, see WO 87/06614, U.S. Pat. Nos. 5,472,869, 5,384,253, WO9209696, and WO9321335. All of these transformation patents and publications are incorporated by reference. In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during dedifferentiation using appropriate techniques within the skill of an artisan.

Genes encoding modified Cry1Ca insecticidal toxins and variants can be inserted into plant cells using a variety of techniques which are well known in the art as disclosed above. For example, a large number of cloning vectors comprising a marker that permits selection of the transformed microbial cells and a replication system functional in *E. coli* are available for preparation and modification of foreign genes for insertion into higher plants. Such manipulations may include, for example, the insertion of mutations, truncations, additions, deletions, or substitutions as desired for the intended use. The vectors comprise, for example, pBR322, pUC series, M13mp series, pACYC184, etc. Accordingly, the sequence encoding the Cry protein or variants can be inserted into the vector at a suitable restriction site. The resulting plasmid is used for transformation of *E. coli*, the cells of which are cultivated in a suitable nutrient medium, then harvested and lysed so that workable quantities of the plasmid are recovered. Sequence analysis, restriction fragment analysis, electrophoresis, and other biochemical-molecular biological methods are generally carried out as methods of analysis. After each manipulation, the DNA sequence used can be cleaved and joined to the next DNA sequence. Each manipulated DNA sequence can be cloned in the same or other plasmids.

Depending on the plant transformation method, ancillary DNA sequences may be necessary. If, for example, a Ti or Ri plasmid is used for the transformation of the plant cell, then at least a T-DNA right border repeat, but often both the right border repeat and the left border repeat of the Ti or Ri plasmid will be joined as the flanking region of the genes desired to be inserted into the plant cell. The use of T-DNA-containing vectors for the transformation of plant cells has been intensively researched and sufficiently described in EP 120516; Lee and Gelvin (2008), Fraley et al., (1986), and An et al., (1985), and is well established in the field.

Once the inserted DNA has been integrated into the plant genome, it is relatively stable throughout subsequent generations. The vector used to transform the plant cell normally contains a selectable marker gene encoding a protein that confers on the transformed plant cells tolerance to a herbicide or an antibiotic, such as bialaphos, kanamycin, G418, bleomycin, or hygromycin, inter alia. The individually employed selectable marker gene should accordingly permit the selection of transformed cells while the growth of cells that do not contain the inserted DNA is suppressed by the selective compound.

A large number of techniques are available for inserting DNA into a host plant cell. Those techniques include transformation with T-DNA delivered by *Agrobacterium tumefaciens* or *Agrobacterium rhizogenes* as the transformation agent. Additionally, fusion of plant protoplasts with liposomes containing the DNA to be delivered, direct injection of the DNA, biolistics transformation (microparticle bombardment), or electroporation, as well as other possible methods, may be employed. One skilled in the field of plant transformation will understand that multiple methodologies are available for the production of transformed plants, and they may be modified and specialized to accommodate biological differences between various host plant species.

If *Agrobacterium* strains are used for the transformation, the DNA to be inserted will be cloned into special plasmids, namely either into an intermediate (shuttle) vector or into a binary vector. The intermediate vectors can be integrated into the Ti or Ri plasmid or derivatives thereof by homologous recombination owing to sequences that are homologous between the Ti or Ri plasmid and the intermediate plasmid. The Ti or Ri plasmid also comprises the vir region comprising vir genes necessary for the transfer of the T-DNA. Intermediate vectors cannot replicate in *Agrobacteria*. The intermediate vector can be transferred into *Agrobacterium tumefaciens* by means of a helper plasmid (via bacterial conjugation), by electroporation, by direct DNA, chemically mediated transformation, or by other methodologies. Binary vectors can replicate autonomously in both *E. coli* and *Agrobacterium* cells. They comprise sequences, framed by the right and left T-DNA border repeat regions, that may include a selectable marker gene functional for the selection of transformed plant cells, a cloning linker, cloning polylinker, or other sequence which can function as an introduction site for genes destined for plant cell transformation. They can be transformed directly into *Agrobacterium* cells (Holsters et al., (1978)) by electroporation, or by direct DNA, chemically mediated transformation, or introduced by bacterial conjugation, or by other methodologies. The *Agrobacterium* used as host cell is to comprise a plasmid carrying a vir region. The vir region is necessary for the transfer of the T-DNA into the plant cell. Additional T-DNA regions additive to the one containing the gene encoding the B.t. insecticidal toxin protein or its variants may be present in the *Agrobacterium* host cell. The bacterium cells so transformed are used for the transformation of plant cells. Plant explants (for example, pieces of leaf, segments of stalk, roots, but also protoplasts or suspension-cultivated cells) can advantageously be cultivated with *Agrobacterium tumefaciens* or *Agrobacterium rhizogenes* for the transfer of the DNA into the plant cell. Whole plants may then be regenerated from the infected plant material following placement in suitable growth conditions and culture medium, which may contain antibiotics or herbicides for selection of the transformed plant cells. The plants so obtained can then be tested for the presence of the inserted DNA.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties, for example, the ability to control the feeding of plant pest insects.

No special demands are made in the construction of the plasmids in the case of those used for injection and electroporation. It is possible to use ordinary plasmids, such as, for example, pUC derivatives appropriately modified to contain all the genes desired to be transferred to plant cells.

The activity of recombinant polynucleotides inserted into plant cells can be dependent upon the influence of endogenous plant DNA adjacent to the insert. Thus, another option is to take advantage of events that are known to be excellent locations in a plant genome for insertions. See e.g. WO 2005/103266 A1, relating to Cry1F and Cry1Ac cotton events; the subject B.t. insecticidal toxin gene can be substituted in those genomic loci in place of the Cry1F or Cry1Ac inserts. Targeted homologous recombination, for example, can be used according to the subject invention. This type of technology is the subject of, for example, WO 03/080809 and the corresponding published U.S. application (USPA 20030232410), relating to the use of zinc fingers for targeted recombination. The use of recombinases (cre-lox and flp-frt for example) is also known in the art.

In a preferred embodiment of the subject invention, plants will be transformed with genes wherein the codon usage of the protein coding region has been optimized for plants. See, for example, U.S. Pat. No. 5,380,831, which is hereby incorporated by reference. Also, advantageously, plants encoding a truncated toxin will be used. The truncated toxin typically will encode about 55% to about 80% of the full length toxin. Methods for creating synthetic B.t. genes for use in plants are known in the art (Stewart 2007).

Another variable is the choice of a selectable marker. The preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which code for tolerance to glyphosate; hygromycin; methotrexate; phosphinothricin (bialaphos); imidazolinones, sulfonylureas and triazolopyrimidine herbicides, such as chlorosulfuron; bromoxynil, dalapon and the like. Examples of such genes are provided in Merlo, (2002), which is incorporated herein by reference.

In addition to a selectable marker, it may be desirable to use a reporter gene. In some instances a reporter gene may be used without a selectable marker. Reporter genes are genes which typically do not provide a growth advantage to the recipient organism or tissue. The reporter gene typically encodes for a protein which provides for some phenotypic change or enzymatic property. A preferred reporter gene is the glucuronidase (GUS) gene. Other examples of reporter genes are provided in Merlo (2002).

Regardless of transformation technique, the gene is preferably incorporated into a gene transfer vector adapted to express the B.t insecticidal toxin genes and variants in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus, and the like may be used. Plant promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g., actin, ubiquitin, CaMV 35S). Tissue specific promoters are responsible for gene expression in specific cell or tissue types, such as the leaves or seeds (e.g., zein, oleosin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Under certain circumstances it may be desirable to use an inducible promoter. An inducible promoter is responsible for expression of genes in response to a specific signal, such as: physical stimulus (e.g. heat shock genes); light (e.g. RUBP carboxylase); hormone (e.g. glucocorticoid); antibiotic (e.g. tetracycline); metabolites; and stress (e.g. drought). Other desirable transcription and translation elements that function in plants may be used, such as 5' untranslated leader sequences, RNA transcription termination sequences and poly-adenylate addition signal sequences. Numerous plant-specific gene transfer vectors are known in the art.

The subject invention includes plant cells that are not totipotent (non-totipotent), plant cells that are not propagative material (for example, leaf cells in some embodiments; seed cells are excluded from some embodiments) and are incapable of differentiating into whole plants. The subject invention includes plant cells that have uses other than for regenerating into a whole plant. For example, said plant cells can be used to produce a protein (such as a DIG-465 protein of the subject invention). Thus, plant cells of the subject invention include those that have uses other than totipotency (that is, some cells of subject invention are not regenerable into a whole plant). However, some embodiments do include seed cells and plant cells that can be regenerated into a whole plant.

A further method for identifying the toxins and genes of the subject invention is through the use of oligonucleotide probes. These probes are detectable nucleotide sequences. These sequences may be rendered detectable by virtue of an appropriate radioactive label or may be made inherently fluorescent as described in U.S. Pat. No. 6,268,132. As is well known in the art, if the probe molecule and nucleic acid sample hybridize by forming strong base-pairing bonds between the two molecules, it can be reasonably assumed that the probe and sample have substantial sequence homology. Preferably, hybridization is conducted under stringent conditions by techniques well-known in the art, as described, for example, in Keller and Manak (1993). Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

As used herein the terms "stringent conditions" or "stringent hybridization conditions" are intended to refer to conditions under which a probe will hybridize (anneal) to its target sequence to a detectably greater degree than to other sequences (e.g. at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA/DNA hybrids, the thermal melting point (Tm) is the temperature (under defined ionic strength and pH) at which 50% of a complementary target sequence hybridizes to a perfectly matched probe. Tm is reduced by about 1° C. for each 1% of mismatching; thus, Tm, hybridization conditions, and/or wash conditions can be adjusted to facilitate annealing of sequences of the desired identity. For example, if sequences with >90% identity are sought, the Tm can be decreased 10° C. Generally, stringent conditions are selected to be about 5° C. lower than the Tm for the specific sequence and its complement at a defined ionic strength and pH. However, highly stringent conditions can utilize a hybridization and/or wash at 1° C., 2° C., 3° C., or 4° C. lower than the Tm; moderately stringent conditions can utilize a hybridization and/or wash at 6° C., 7° C., 8° C., 9° C., or 10° C. lower than the Tm, and low stringency conditions can utilize a hybridization and/or wash at 11° C., 12° C., 13° C., 14° C., 15° C., or 20° C. lower than the Tm.

Tm (in ° C.) may be experimentally determined or may be approximated by calculation. For DNA-DNA hybrids, the Tm can be approximated from the equation of Meinkoth and Wahl (1984):

$$Tm(° C.)=81.5° C.+16.6(\log M)+0.41(\% GC)-0.61(\% \text{formamide})-500/L;$$

where M is the molarity of monovalent cations, % GC is the percentage of guanosine and cytosine nucleotides in the DNA, % formamide is the percentage of formamide in the hybridization solution, and L is the length of the hybrid in base pairs Alternatively, the Tm is described by the following formula (Beltz et al., 1983).

$$Tm(° C.)=81.5° C.+16.6(\log[Na+])+0.41(\% GC)-0.61(\% \text{formamide})-600/L$$

where [Na+] is the molarity of sodium ions, % GC is the percentage of guanosine and cytosine nucleotides in the DNA, % formamide is the percentage of formamide in the hybridization solution, and L is the length of the hybrid in base pairs Using the equations, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen (1993) and Ausubel et al., (1995). Also see Sambrook et al., (1989).

Hybridization of immobilized DNA on Southern blots with radioactively labeled gene-specific probes may be performed by standard methods (Sambrook et al., supra). Radioactive isotopes used for labeling polynucleotide probes may include 32P, 33P, 14C, or 3H. Incorporation of radioactive isotopes into polynucleotide probe molecules may be done by any of several methods well known to those skilled in the field of molecular biology. (See, e.g. Sambrook et al., supra.) In general, hybridization and subsequent washes may be carried out under stringent conditions that allow for detection of target sequences with homology to the claimed toxin encoding genes. For double-stranded DNA gene probes, hybridization may be carried out overnight at 20-25° C. below the Tm of the DNA hybrid in 6×SSPE, 5×Denhardt's Solution, 0.1% SDS, 0.1 mg/mL denatured DNA [20×SSPE is 3M NaCl, 0.2 M NaHPO4, and 0.02M EDTA (ethylenediamine tetra-acetic acid sodium salt); 100×

Denhardt's Solution is 20 gm/L Polyvinylpyrollidone, 20 gm/L Ficoll type 400 and 20 gm/L Bovine Serum Albumin (fraction V)].

Washes may typically be carried out as follows:

(1) Twice at room temperature for 15 minutes in 1×SSPE, 0.1% SDS (low stringency wash).

(2) Once at Tm −20° C. for 15 minutes in 0.2×SSPE, 0.1% SDS (moderate stringency wash).

For oligonucleotide probes, hybridization may be carried out overnight at 10-20° C. below the Tm of the hybrid in 6×SSPE, 5×Denhardt's solution, 0.1% SDS, 0.1 mg/mL denatured DNA. Tm for oligonucleotide probes may be determined by the following formula (Suggs et al., 1981).

Tm(° C.)=2(number of *T/A* base pairs)+4(number of G/C base pairs)

Washes may typically be carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

A practitioner skilled in the art will realize that probe molecules for hybridization and hybrid molecules formed between probe and target molecules may be rendered detectable by means other than radioactive labeling.

Variant Toxins.

The genes and toxins useful according to the subject invention include not only the truncated sequences disclosed but also full length sequences, fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. Further as used herein, the term "equivalent toxins" refers to toxins having the same or essentially the same biological activity against the target pests as the claimed toxins. Thus, the variant or variations of the claimed toxins will have at least about 30%, preferably at least about 50%, more preferably at least about 70%, even more preferably at least about 80% of the activity of the claimed toxins. Methods for measuring pesticidal activity are well known in the art and are exemplified herein. By "variants" it is intended herein to include proteins or polypeptides having an amino acid sequence that is at least about 60%, 65%, preferably about 70%, 75%, more preferably about 80%, 85%, most preferably about 90%, 91%, 92%, 93%, 94%, 95%, 96%, 97%, 98% or 99% identical to the amino acid sequence of SEQ ID NOs:2, 4, 6, 8, 10, 12, 14, 16, 18, 20, 22, 24, 26, 28, 30, 32, 34, 36, 38, and 40. Variants also include polypeptides encoded by a nucleic acid molecule that hybridizes to the nucleic acid molecule of SEQ ID NOs:1, 3, 5, 7, 9, 11, 13, 15, 17, 19, 21, 23, 25, 27, 29, 31, 33, 35, 37, or 39, or a complement thereof, under stringent conditions. Such variants generally will retain the claimed activity. Variants include polypeptides that differ in amino acid sequence due to mutagenesis. Variant proteins encompassed by the present invention are insecticidally active.

Variant proteins can also be designed that differ at the primary amino acid sequence level and which retain the same or similar overall essential three-dimensional structure, surface charge distribution, and the like. See e.g. U.S. Pat. No. 7,058,515; Larson et al., (2002); Crameri et al., (1997); Stemmer, W. P. C. (1994a); Stemmer, W. P. C. (1994b)" Stemmer, W. P. C. (1995); Crameri et al., (1996a); and Crameri et al., (1996b).

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. The amino acid identity will typically be greater than 60%, preferably be greater than 75%, more preferably greater than 80%, more preferably greater than 90%, and can be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: nonpolar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

Classes of Amino Acids and Examples.

| Class of Amino Acid | Examples of Amino Acids |
| --- | --- |
| Nonpolar Side Chains | Ala, Val, Leu, Ile, Pro, Met, Phe, Trp |
| Uncharged Polar Side Chains | Gly, Ser, Thr, Cys, Tyr, Asn, Gln |
| Acidic Side Chains | Asp, Glu |
| Basic Side Chains | Lys, Arg, His |
| Beta-branched Side Chains | Thr, Val, Ile |
| Aromatic Side Chains | Tyr, Phe, Trp, His |

In some instances, non-conservative substitutions can also be made. The critical factor is that these substitutions must not significantly detract from the biological activity of the toxin.

Preferred insecticidal toxins proteins of the present invention are encoded by a nucleotide sequence sufficiently identical to the nucleotide sequences of SEQ ID NOs:1, 3, 5, 7, 9, 11, 13, 15, 17, 19, 21, 23, 25, 27, 29, 31, 33, 35, 37 or 39. By "sufficiently identical" is intended an amino acid or nucleotide sequence that has at least about 60% or 65% sequence identity, preferably about 70% or 75% sequence identity, more preferably about 80% or 85% sequence identity, most preferably about 90%, 91%, 92%, 93%, 94%, 95%, 96%, 97%, 98% or 99% sequence identity compared to a reference sequence as analyzed by one of the alignment programs described herein, employing standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acid sequences, the sequences are aligned for optimal comparison purposes. The percent identity between the two sequences is a function of the number of identical positions shared by the sequences (i.e.

percent identity=number of identical positions/total number of positions (e.g. overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990), modified as in Karlin and Altschul (1993). Such an algorithm is incorporated into the BLASTN and BLASTX programs of Altschul et al., (1990). BLAST searches may be conveniently used to identify sequences homologous (similar) to a query sequence in nucleic or protein databases. BLAST nucleotide searches can be performed with the BLASTN program, score=100, word length=12, to identify nucleotide sequences having homology to claimed nucleic acid molecules of the invention. BLAST protein searches can be performed with the BLASTX program, score=50, word length=3, to identify amino acid sequences having homology to claimed insecticidal protein molecules of the invention.

To obtain gapped alignments for comparison purposes, Gapped BLAST can be utilized as described in Altschul et al., (1997). Alternatively, PSI-Blast can be used to perform an iterated search that detects distant relationships between molecules Altschul et al., (1997). When utilizing BLAST, Gapped BLAST, and PSI-Blast programs, the default parameters of the respective programs (e.g. BLASTX and BLASTN) can be used. See www.ncbi.nlm.nih.gov. Alignment may also be performed manually by inspection.

A non-limiting example of a mathematical algorithm utilized for the comparison of sequences is the ClustalW algorithm (Thompson et al., (1994). ClustalW compares sequences and aligns the entirety of the amino acid or DNA sequence, and thus can provide data about the sequence conservation of the entire amino acid sequence or nucleotide sequence. The ClustalW algorithm is used in several commercially available DNA/amino acid analysis software packages, such as the ALIGNX module of the Vector NTI Program Suite (Invitrogen, Inc., Carlsbad, Calif.). When aligning amino acid sequences with ALIGNX, one may conveniently use the default settings with a Gap open penalty of 10, a Gap extend penalty of 0.1 and the blosum63mt2 comparison matrix. After aligning two protein sequences with ALIGNX, the percent amino acid similarity (consensus) or identity between the two sequences can be assessed. When aligning two DNA sequences with ALIGNX, one may conveniently use the default settings with a Gap open penalty of 15, a Gap extend penalty of 6.6 and the swgapdnamt comparison matrix. After aligning two DNA sequences with ALIGNX, the percent identity between the two sequences can be assessed.

A second non-limiting example of a software program useful for analysis of ClustalW alignments is GeneDoc™ (developed by Karl Nicholas, iubio.bio.indiana.edu/soft/molbio/ibmpc/genedoc-readme.html). GeneDoc™ allows assessment of amino acid (or DNA) similarity and identity between multiple proteins.

Another non-limiting example of a mathematical algorithm utilized for the comparison of sequences is the algorithm of Myers and Miller (1988). Such an algorithm is incorporated into the wSTRETCHER program, which is part of the wEMBOSS sequence alignment software package (available at emboss.sourceforge.net/). STRETCHER calculates an optimal global alignment of two sequences using a modification of the classic dynamic programming algorithm which uses linear space. The output is a standard alignment file. The substitution matrix, gap insertion penalty and gap extension penalties used to calculate the alignment may be specified. When utilizing the STRETCHER program for comparing nucleotide sequences, a Gap open penalty of 16 and a Gap extend penalty of 4 can be used. The scoring matrix file for comparing DNA sequences is EDNAFULL. When used for comparing amino acid sequences, a Gap open penalty of 12 and a Gap extend penalty of 2 can be used. The scoring matrix file for comparing protein sequences is EBLOSUM62.

A further non-limiting example of a mathematical algorithm utilized for the comparison of sequences is the algorithm of Needleman and Wunsch (1970), which is incorporated in the sequence alignment software packages GAP Version 10 and wNEEDLE (emboss.sourceforge.net/). GAP version 10 may be used to determine sequence identity or similarity using the following parameters: for a nucleotide sequence, % identity and % similarity are found using GAP Weight of 50 and Length Weight of 3, and the nwsgapdna.cmp scoring matrix. For amino acid sequence comparison, % identity or % similarity fare determined using GAP weight of 8 and length weight of 2, and the BLOSUM62 scoring program. wNEEDLE reads two input sequences, finds the optimum alignment (including gaps) along their entire length, and writes their optimal global sequence alignment to file. The algorithm uses a dynamic programming method to ensure the alignment is optimum, by exploring all possible alignments and choosing the best. A scoring matrix is read that contains values for every possible residue or nucleotide match. wNEEDLE finds the alignment with the maximum possible score where the score of an alignment is equal to the sum of the matches taken from the scoring matrix, minus penalties arising from opening and extending gaps in the aligned sequences. The substitution matrix and gap opening and extension penalties are user-specified. When amino acid sequences are compared, a default Gap open penalty of 10, a Gap extend penalty of 0.5, and the EBLOSUM62 comparison matrix are used. When DNA sequences are compared using wNEEDLE, a Gap open penalty of 10, a Gap extend penalty of 0.5, and the EDNAFULL comparison matrix are used.

Equivalent programs may also be used. By "equivalent program" is intended any sequence comparison program that, for any two sequences in question, generates an alignment having identical nucleotide residue matches and an identical percent sequence identity when compared to the corresponding alignment generated by ALIGNX, wNEEDLE, or wSTRETCHER. The % identity is the percentage of identical matches between the two sequences over the reported aligned region (including any gaps in the length) and the % similarity is the percentage of matches between the two sequences over the reported aligned region (including any gaps in the length).

Toxin Fragments and Equivalents.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

Alterations can be made at the amino or carboxy terminus of the insecticidal proteins and variants of the invention that result in polypeptides that retain biological activity. Fragments or biologically active portions include polypeptide fragments comprising amino acid sequences sufficiently identical to the amino acid sequence set forth in SEQ ID NOs:2, 4, 6, 8, 10, 12, 14, 16, 18, 20, 22, 24, 26, 28, 30, 32, 34, 36, 38, and 40. A biologically active portion of a delta endotoxin protein can be a polypeptide that is, for example, 10, 25, 50, 100, or more amino acids in length. Such biologically active portions can be prepared by recombinant protein engineering techniques well known in the art and evaluated for insecticidal activity. Methods for measuring pesticidal activity are well known in the art. As used herein a fragment encompasses at least 8 contiguous amino acids of SEQ ID NOs:2, 4, 6, 8, 10, 12, 14, 16, 18, 20, 22, 24, 26, 28, 30, 32, 34, 36, 38, and 40. The invention encompasses other fragments, however, such as any fragment in the protein greater than about 10, 20, 30, 50, 100, 150, 200, 250, 300, 350, 400, 450, 500, 550, 600, 650, 700, 750, 800, 850, 900, 950, 1000, 1050, 1100, 1150, or 1200 amino acids, up to the full length of the insecticidal proteins or variant proteins of SEQ ID NOs:2, 4, 6, 8, 10, 12, 14, 16, 18, 20, 22, 24, 26, 28, 30, 32, 34, 36, 38, and 40.

Fragments with improved biological activity, pest spectrum, or the ability to control resistant insect populations are also provided in the present invention. Modifications can be made to Cry proteins to produce fragments with improved pore formation and thereby pesticidal activity. In the case of three-domain Cry proteins, domain 1 is comprised of seven α-helices involved in pore formation in the midgut of susceptible insects. Modified DIG proteins with improved activity can be designed to have N-terminal deletions in regions with putative secondary structure homology to α-helix 1 and α-helix 2 of domain 1.

Proteases may be used to directly obtain active fragments of these toxins. A fragment of a claimed insecticidal toxin will comprise at least about 15, 25, 30, 50, 75, 100, 125, 150, 175, 200, 250, 300, 350, 400, 450, 500, 550, 600, 650, 700, 800, 900, 1000, 1100 or 1200 contiguous amino acids, or up to the total number of amino acids present in a full-length insecticidal toxin of the invention (for example, 625 amino acids for SEQ ID NO:2, or 625 amino acids for SEQ ID NO:4).

Core Toxin and Protoxin Chimeras.

A majority of *Bacillus thuringiensis* delta-endotoxin crystal protein molecules are composed of two functional segments. The protease-resistant core toxin is the first segment and corresponds to about the first half of the protein molecule. The approximately C-terminal half of the molecule is the second segment. For purposes of this application, this second segment will be referred to herein as the "protoxin segment." The protoxin segment is believed to participate in toxin crystal formation (Arvidson et al., (1989)). The full 130 kDa toxin molecule is rapidly processed to the resistant core segment by protease in the insect gut. The protoxin segment may thus convey a partial insect specificity for the toxin by limiting the accessibility of the core to the insect by reducing the protease processing of the toxin molecule (Haider et al., (1986)) or by reducing toxin solubility (Aronson et al., (1991)).

Chimeric proteins advantageously joined within the toxin domains of Cry1Fa and Cry1Ab have been reported (U.S. Pat. No. 5,527,883). Other success in the area has been reported in the literature. For example, the construction of hybrid delta-endotoxins is reported in the following related art. Intl. Pat. Appl. Publ. No. WO 95/30753 discloses the construction of hybrid *B. thuringiensis* delta-endotoxins for production in *Pseudomonas fluorescens* in which the non-toxic protoxin fragment of Cry1F has been replaced by the non-toxic protoxin fragment from the Cry1Ac/Cry1Ab that is disclosed in U.S. Pat. No. 5,128,130. That patent also discloses the construction of hybrid *B. thuringiensis* delta-endotoxins for production in *P. fluorescens* in which a portion of the non-toxic protoxin segment of Cry1Ac is replaced with the corresponding non-toxic protoxin fragment of Cry1Ab. U.S. Pat. No. 5,055,294 discloses the construction of a specific hybrid delta-endotoxin between Cry1Ac (amino acid residues 1-466) and Cry1Ab (amino acid residues 466-1155) for production in *P. fluorescens*. Although the aforementioned patent discloses the construction of a hybrid toxin within the active toxin segment, no specifics are presented in regard to the hybrid toxin's insecticidal activity. International Patent Application Publication No. WO 95/30752 discloses the construction of hybrid *B. thuringiensis* delta-endotoxins for production in *P. fluorescens* in which the non-toxic protoxin segment of Cry1C is replaced by the non-toxic protoxin segment from Cry1Ab. The afore-mentioned application further discloses that the activity against *Spodoptera exigua* for the hybrid delta-endotoxin is improved over that of the parent active toxin, Cry1C. International Patent Application Publication No. WO 95/06730 discloses the construction of a hybrid *B. thuringiensis* delta-endotoxin consisting of domains 1 and 2 of Cry1E coupled to domain 3 and the non-toxic protoxin segment of Cry1C. Insect bioassays performed against *Manduca sexta* (sensitive to Cry1C and Cry1E), *Spodoptera exigua* (sensitive to Cry1C), and *Mamestra brassicae* (sensitive to Cry1C) show that the hybrid Cry1E/Cry1C hybrid toxin is active against *M. sexta, S. exigua*, and *M. brassicae*. The bioassay results were expressed as $EC_{50}$ values (toxin concentration giving a 50% growth reduction) rather than $LC_{50}$ values (toxin concentration giving 50% mortality). Although the delta-endotoxins used for bioassay were produced in *B. thuringiensis*, only artificially-generated active segments of the delta-endotoxins were used, not the naturally-produced crystals typically produced by *B. thuringiensis* that are present in commercial *B. thuringiensis* formulations. Bioassay results indicated that the $LC_{50}$ values for the hybrid Cry1E/Cry1C crystal against *S. frugiperda* were 1.5 to 1.7 fold lower (i.e. were more active) than for native Cry1C. This art also discloses the construction of a hybrid *B. thuringiensis* delta-endotoxin between Cry1Ab (domains 1 and 2) and Cry1C (domain 3 and the non-toxic protoxin segment), although no data are given regarding the hybrid toxin's activity or usefulness.

Lee et al., (1995) report the construction of hybrid *B. thuringiensis* delta-endotoxins between Cry1Ac and Cry1Aa within the active toxin segment. Artificially generated active segments of the hybrid toxins were used to examine protein interactions in susceptible insect brush border membranes vesicles (BBMV). The bioactivity of the hybrid toxins was not reported. Honee et al., (1991) report the construction of hybrid delta-endotoxins between Cry1C (domain 1) and Cry1Ab (domains 2 and 3) and the reciprocal hybrid between Cry1Ab (domain 1) and Cry1C (domains 2 and 3). These hybrids failed to show any significant increase in activity against susceptible insects. Furthermore, the Cry1C (domain 1)/Cry1Ab (domains 2 and 3) hybrid toxin was found to be hypersensitive to protease degradation. A report by Schnepf et al., (1990) discloses the construction of Cry1Ac hybrid toxin in which a small portion of domain 2 was replaced by the corresponding region of Cry1Aa, although no significant increase in activity against susceptible insect larvae was observed.

The chimeric toxins of the subject invention comprise a full core N-terminal toxin portion of a B.t. toxin and, at some point past the end of the toxin portion, the protein has a transition to a heterologous protoxin sequence. The transition to the heterologous protoxin segment can occur at approximately the native toxin/protoxin junction or a portion of the native protoxin (extending past the toxin portion) can be retained with the transition to the heterologous protoxin occurring downstream. For example, a chimeric toxin of the subject invention may have the full toxin portion of a modified Cry1Ca toxin such as amino acids 1-628 of DIG-473 or DIG-465 and a heterologous protoxin segment (amino acids 629 to the C-terminus). In a preferred embodiment, the heterologous protoxin segment portion is taken from Cry1Ab.

A person skilled in this art will appreciate that B.t. toxins, even within a certain class, will vary to some extent in length and in the precise location of the transition from the core toxin portion to protoxin portion. The transition from core toxin portion to protoxin portion will typically occur at between about 50% to about 60% of the full length toxin. The chimeric toxin of the subject invention includes the full expanse of this core N-terminal toxin portion, such is the full 628 amino acid length of IRDIG544.12 insecticidal toxin protein. SEQ ID NO:15 discloses the 1887 nucleotide sequence of the DIG-465-encoding DNA, of which the 5'-terminal 1887 nucleotides comprise the coding region for the core toxin segment of Cry1Ca with a mutation L57A (leucine at amino acid position 57 substituted for alanine), one embodiment of the subject invention. SEQ ID NO:16 discloses the 628 amino acid sequence of the full-length DIG-465 polypeptide, of which the N-terminal core portion of Cry1Ca with the above mentioned amino acid substitutions. SEQ ID NO:23 discloses the 1887 nucleotide sequence of DIG-473-encoding DNA, which comprises the coding region for the core toxin segment of Cry1Ca with a mutation F596M (phenylalanine at amino acid position 596, substituted for methionine), another subject of the invention. SEQ ID NO:24 discloses the 628 amino acid sequence of the full-length DIG-473 polypeptide, which comprises the portion of Cry1Ca with the above mentioned amino acid substitutions.

With regard to the protoxin portion, the full expanse of the native Cry1Ab protoxin portion extends from the end of the toxin portion of the Cry1Ab full length protein to the C-terminus of the molecule. Attention is drawn to the last about 100 to 150 amino acids of this protoxin, which are most critical to include in the chimeric toxin of the subject invention.

Because Cry proteins have selective insecticidal activity, most are active on a limited range of target pests. There is, therefore, a need to further improve the biological activity attributes of Cry proteins. Cry proteins with unique binding characteristics and modes of action are useful in strategies to expand the range of insect pests controlled or counter the development of B.t. resistance.

Domain III Modifications.

As described herein, the B.t. insecticidal toxins of the subject invention are 3-domain type toxins, comprising Domain I, Domain II, and Domain III. Domain III binds certain classes of receptor proteins and perhaps participates in insertion of an oligomeric toxin pre-pore. Specific hybrid toxins that comprised domain III substitutions were shown to have superior toxicity against *Spodoptera exigua* (de Maagd et al., 1996) and guidance exists on the design of the Cry toxin domain swaps (Knight et al., 2004).

Domain I modifications. Numerous studies using biochemical and molecular approaches have provided information on the determinants of Cry protein binding and insertion into insect midgut membranes (reviewed in Piggot and Ellar, 2007). Domain I from Cry1A and Cry3A proteins has been studied for the ability to insert and form pores in membranes. α-helices 4 and 5 of domain I play key roles in membrane insertion and pore formation (Walters et al., 1993, Gazit et al., 1998; Nunez-Valdez et al., 2001), with the other helices proposed to contact the membrane surface like the ribs of an umbrella (Gazit et al., 1998).

Alpha-helix 3 appears in some instances to be required for oligomeric pre-pore formation and toxicity. Some α-helix 3 mutants are able to bind receptors but do not form oligomers and are non-toxic to *Manduca sexta* (reviewed in Jimenez-Juarez et al., 2008). However, proteolytically activated forms of Cry3Aa1 lack α-helices 1, 2 and 3 (Carroll et al., 1997).

Alpha-helix 1 is removed following receptor binding. Gomez et al., (2002) found that Cry1Ab oligomers formed upon BBMV receptor binding lacked the α-helix 1 portion of domain I. Also, Soberon et al., (2007) have shown that N-terminal deletion mutants of Cry1Ab and Cry1Ac which lack approximately 60 amino acids encompassing α-helix 1 on the three dimensional Cry structure are capable of assembling monomers of molecular weight about 60 kDa into pre-pores in the absence of cadherin binding. These N-terminal deletion mutants were reported to be active on Cry-resistant insect larvae. Furthermore, Diaz-Mendoza et al., (2007) described Cry1Ab fragments of 43 kDa and 46 kDa that retained activity on Mediterranean corn borer (*Sesamia nonagrioides*). These fragments were demonstrated to include amino acid residues 116 to 423; however the precise amino acid sequences were not elucidated and the mechanism of activity of these proteolytic fragments is unknown. The results of Gomez et al., (2002), Soberon et al., 2007 and Diaz-Mendoza et al., (2007) contrast with those of Hofte et al., (1986), who reported that deletion of 36 amino acids from the N-terminus of Cry1Ab resulted in loss of insecticidal activity.

Anti-Toxin Antibodies.

Equivalent toxins and/or genes encoding these equivalent toxins can be derived from *Bacillus thuringiensis* isolates and/or DNA libraries using the teachings provided herein. There are a number of methods for obtaining the pesticidal toxins of the instant invention. For example, antibodies immunoreactive to the pesticidal toxins disclosed and claimed herein can be used to identify and isolate other toxins from a mixture of proteins. Specifically, antibodies may be raised to the portions of the toxins which are most constant and most distinct from other B.t. toxins. These antibodies can then be used to specifically identify equivalent toxins with the characteristic activity by, for example, immunoprecipitation, enzyme linked immunosorbent assay (ELISA), or immunoblotting (western blotting). Antibodies to the toxins disclosed herein, or to equivalent toxins, or fragments of these toxins, can readily be prepared using standard procedures in this art. The genes which encode these toxins can then be obtained from the microorganisms that produce the toxins.

Once the B.t. insecticidal toxin has been isolated, antibodies specific for the toxin may be raised by conventional methods that are well known in the art. Repeated injections into a host of choice over a period of weeks or months will elicit an immune response and result in significant anti-B.t. toxin serum titers. Preferred hosts are mammalian species and more highly preferred species are rabbits, goats, sheep, and mice. Blood drawn from such immunized animals may be processed by established methods to obtain antiserum (polyclonal antibodies) reactive with the B.t. insecticidal toxin. The antiserum may then be affinity purified by adsorption to the toxin according to techniques known in the art. Affinity purified antiserum may be further purified by isolating the immunoglobulin fraction within the antiserum using procedures known in the art. The resulting material will be a heterogeneous population of immunoglobulins reactive with the B.t. insecticidal toxin.

Anti-B.t. toxin antibodies may also be generated by preparing a semi-synthetic immunogen consisting of a synthetic peptide fragment of the B.t. insecticidal toxin conjugated to an immunogenic carrier. Numerous schemes and instruments useful for making peptide fragments are well known in the art. Many suitable immunogenic carriers such as bovine serum albumin (BSA) or keyhole limpet hemocyanin are also well known in the art, as are techniques for coupling the immunogen and carrier proteins. Once the semi-synthetic immunogen has been constructed, the procedure for making antibodies specific for the B.t. insecticidal toxin fragment is identical to those used for making antibodies reactive with natural B.t. toxin.

Anti-B.t. toxin monoclonal antibodies (MAbs) are readily prepared using purified B.t. insecticidal toxin. Methods for producing MAbs have been practiced for over 15 years and are well known to those of ordinary skill in the art. Repeated intraperitoneal or subcutaneous injections of purified B.t. insecticidal toxin in adjuvant will elicit an immune response in most animals. Hyperimmunized B-lymphocytes are removed from the animal and fused with a suitable fusion partner cell line capable of being cultured indefinitely. Preferred animals whose B-lymphocytes may be hyperimmunized and used in the production of MAbs are mammals. More preferred animals are rats and mice and most preferred is the BALB/c mouse strain.

Numerous mammalian cell lines are suitable fusion partners for the production of hybridomas. Many such lines are available from the American Type Culture Collection (ATCC, Manassas, Va.) and commercial suppliers. Preferred fusion partner cell lines are derived from mouse myelomas and the HL-1® Friendly myeloma-653 cell line (Ventrex, Portland, Me.) is most preferred. Once fused, the resulting hybridomas are cultured in a selective growth medium for one to two weeks. Two well known selection systems are available for eliminating unfused myeloma cells, or fusions between myeloma cells, from the mixed hybridoma culture. The choice of selection system depends on the strain of mouse immunized and myeloma fusion partner used. The AAT selection system, described by Taggart and Samloff (1983), may be used; however, the HAT (hypoxanthine, aminopterin, thymidine) selection system, described by Littlefield (1964), is preferred because of its compatibility with the preferred mouse strain and fusion partner mentioned above. Spent growth medium is then screened for immunospecific MAb secretion. Enzyme linked immunosorbent assay (ELISA) procedures are best suited for this purpose; though, radioimmunoassays adapted for large volume screening are also acceptable. Multiple screens designed to consecutively pare down the considerable number of irrelevant or less desired cultures may be performed. Cultures that secrete MAbs reactive with the B.t. insecticidal toxin may be screened for cross-reactivity with known B.t. insecticidal toxins. MAbs that preferentially bind to the preferred B.t. insecticidal toxin may be isotyped using commercially available assays. Preferred MAbs are of the IgG class, and more highly preferred MAbs are of the IgG1 and IgG2a subisotypes.

Hybridoma cultures that secrete the preferred MAbs may be sub-cloned several times to establish monoclonality and stability. Well known methods for sub-cloning eukaryotic, non-adherent cell cultures include limiting dilution, soft agarose and fluorescence activated cell sorting techniques. After each subcloning, the resultant cultures preferably are re-assayed for antibody secretion and isotype to ensure that a stable preferred MAb-secreting culture has been established.

The anti-B.t. toxin antibodies are useful in various methods of detecting the claimed B.t. insecticidal toxin of the instant invention, and variants or fragments thereof. It is well known that antibodies labeled with a reporting group can be used to identify the presence of antigens in a variety of milieus. Antibodies labeled with radioisotopes have been used for decades in radioimmunoassays to identify, with great precision and sensitivity, the presence of antigens in a variety of biological fluids. More recently, enzyme labeled antibodies have been used as a substitute for radiolabeled antibodies in the ELISA assay. Further, antibodies immunoreactive to the B.t. insecticidal toxin of the present invention can be bound to an immobilizing substance such as a polystyrene well or particle and used in immunoassays to determine whether the B.t. toxin is present in a test sample.

In one preferred embodiment, insecticidal proteins or a variant is delivered orally through a transgenic plant comprising a nucleic acid sequence that expresses a toxin of the present invention. The present invention provides a method of producing an insect-resistant transgenic plant, comprising introducing a nucleic acid molecule of the invention into the plant wherein the toxin is expressible in the transgenic plant in an effective amount to control an insect. In a non-limiting example, a basic cloning strategy may be to subclone full length or modified Cry coding sequences (CDS) into a plant expression plasmid at NcoI and SacI restriction sites. The resulting plant expression cassettes containing the appropriate Cry coding region under the control of plant expression elements, (e.g., plant expressible promoters, 3' terminal transcription termination and polyadenylate addition determinants, and the like) are subcloned into a binary vector plasmid, utilizing, for example, Gateway® technology or standard restriction enzyme fragment cloning procedures. LR Clonase™ (Invitrogen) for example, may be used to recombine the full length and modified gene plant expression cassettes into a binary plant transformation plasmid if the Gateway® technology is utilized. It is convenient to employ a binary plant transformation vector that harbors a bacterial gene that confers resistance to the antibiotic spectinomycin when the plasmid is present in *E. coli* and *Agrobacterium* cells. It is also convenient to employ a binary vector plasmid that contains a plant-expressible selectable marker gene that is functional in the desired host plants. Examples of plant-expressible selectable marker genes include but are not limited to aminoglycoside phosphotransferase gene of transposon Tn5 (Aph II) which encodes resistance to the antibiotics kanamycin, neomycin and G418, as well as those genes which code for tolerance to glyphosate; hygromycin; methotrexate; phosphinothricin (bialaphos), imidazolinones, sulfonylureas and triazolopyrimidine herbicides, such as chlorosulfuron, bromoxynil, dalapon and the like.

Alternatively, the plasmid structure of the binary plant transformation vector containing the DIG-465, DIG-473, DIG-468, DIG-483, DIG-462, DIG-463, DIG-464, DIG-466, DIG-467, DIG-469, DIG-474, DIG-482, DIG-485, DIG-487, IRDIG544.8, IRDIG544.9, IRDIG544.11, or IRDIG544.12 gene insert is performed by restriction digest fingerprint mapping of plasmid DNA prepared from candidate *Agrobacterium* isolates by standard molecular biology methods well known to those skilled in the art of *Agrobacterium* manipulation.

Those skilled in the art of obtaining transformed plants via *Agrobacterium*-mediated transformation methods will understand that other *Agrobacterium* strains besides Z707S may be used, and the choice of strain may depend upon the identity of the host plant species to be transformed.

Following are examples which illustrate procedures for practicing the invention. These examples should not be construed as limiting. All percentages are by weight and all solvent mixture proportions are by volume unless otherwise noted. All patents, patent applications, provisional applications, and publications referred to or cited herein are incorporated by reference in their entirety to the extent they are not inconsistent with the explicit teachings of this specification. Unless specifically indicated or implied, the terms "a", "an", and "the" signify "at least one" as used herein.

EXAMPLE 1

Design of a Plant-Optimized Version of the Coding Sequence for B.t. Insecticidal Proteins A DNA sequence having a plant codon bias was designed and synthesized to produce the insecticidal proteins in transgenic monocot and dicot plants. A codon usage table for maize (*Zea mays* L.) was calculated from 706 protein coding sequences (CDS) obtained from sequences deposited in GenBank. Codon usage tables for tobacco (*Nicotiana tabacum,* 1268 CDS), canola (*Brassica napus,* 530 CDS), cotton (*Gossypium hirsutum,* 197 CDS), and soybean (*Glycine max*; ca. 1000 CDS) were downloaded from data at the website www kazusa.or.jp/codon/. A biased codon set that comprises highly used codons common to both maize and dicot datasets, in appropriate weighted average relative amounts, was calculated after omitting any redundant codon used less than about 10% of total codon uses for that amino acid in either plant type. To derive a plant optimized sequence encoding the insecticidal protein, codon substitutions to the insecticidal protein DNA sequences were made such that the resulting DNA sequence had the overall codon composition of the plant-optimized codon bias table. Further refinements of the sequence were made to eliminate undesirable restriction enzyme recognition sites, potential plant intron splice sites, long runs of A/T or C/G residues, and other motifs that might interfere with RNA stability, transcription, or translation of the coding region in plant cells. Other changes were made to introduce desired restriction enzyme recognition sites, and to eliminate long internal Open Reading Frames (frames other than +1). These changes were all made within the constraints of retaining the plant-biased codon composition. To complete the design, a sequence encoding translational Stop codons in all 6 open reading frames was added to the 3' end of the coding regions, and appropriate restriction recognition sites were added to the 5' and 3' ends of the sequences. Synthesis of the designed sequence was performed by a commercial vendor (DNA2.0, Menlo Park, Calif.). Additional guidance regarding the production of synthetic genes can be found in, for example, WO 97/13402 and U.S. Pat. No. 5,380,831.

Plant-optimized DNA sequences encoding DIG proteins of the subject invention (SEQ ID NOs:2, 4, 6, 8, 10, 12, 14, 16, 18, 20, 22, 24, 26, 28, 30, 32, 34, 36, 38, and 40) are disclosed as SEQ ID NOs:1, 3, 5, 7, 9, 11, 13, 15, 17, 19, 21, 23, 25, 27, 29, 31, 33, 35, 37, and 39. DNA molecules comprising sequences disclosed in SEQ ID NOs: 1, 3, 5, 7, 9, 11, 13, 15, 17, 19, 21, 23, 25, 27, 29, 31, 33, 35, 37, and 39 were synthetically assembled by a commercial entity (DNA2.0).

EXAMPLE 2

Construction of Expression Plasmids Encoding Insecticidal Toxins and Expression in Bacterial Hosts Standard cloning methods were used in the construction of *Pseudomonas fluorescens* (Pf) expression plasmids engineered to produce DIG-465 (SEQ ID NO:16), DIG-473 (SEQ ID NO:24), DIG-468 (SEQ ID NO:2), DIG-483 (SEQ ID NO:4), DIG-462 (SEQ ID NO:10), DIG-463 (SEQ ID NO:12), DIG-464 (SEQ ID NO:14), DIG-466 (SEQ ID NO:18), DIG-467 (SEQ ID NO:20), DIG-469 (SEQ ID NO:22), DIG-474 (SEQ ID NO:26), DIG-482 (SEQ ID NO:28), DIG-485 (SEQ ID NO:6), and DIG-487 (SEQ ID NO:8) proteins encoded by plant-optimized coding regions. Restriction endonucleases were obtained from New England BioLabs (NEB; Ipswich, Mass.) and T4 DNA Ligase (Invitrogen Corporation, Carlsbad, Calif.) was used for DNA ligation.

The basic cloning strategy entailed subcloning the DIG-465, DIG-473, DIG-468, DIG-483, DIG-462, DIG-463, DIG-464, DIG-466, DIG-467, DIG-469, DIG-474, DIG-482, DIG-485, or DIG-487 toxin coding sequence (CDS) into pDOW1169 at restriction sites such as SpeI and XhoI, whereby it was placed under the expression control of the Ptac promoter and the rrnBT1T2 terminator from plasmid pKK223-3 (PL Pharmacia, Milwaukee, Wis.). pDOW1169 is a low copy plasmid with the RSF1010 origin of replication, a pyrF gene, and a ribosome binding site preceding the restriction enzyme recognition sites into which DNA fragments containing protein coding regions may be introduced, (US Patent Application US20080193974). The expression plasmid was transformed by electroporation into DC454 (a near wild-type *P. fluorescens* strain having mutations ΔpyrF and lsc::lacIQI), or its derivatives, recovered in SOC-Soy hydrolysate medium, and plated on selective medium (M9 glucose agar lacking uracil, Sambrook et al., supra). Details of the microbiological manipulations are available in Squires, C. H. et al., (2004), US Patent Application 20060008877, US Patent Application 20080193974, and US Patent Application 20080058262, incorporated herein by reference. Strains were validated by restriction digestion of miniprep plasmid DNA.

Growth and Expression Analysis in Shake Flasks.

Production of DIG-465, DIG-473, DIG-468, DIG-483, DIG-462, DIG-463, DIG-464, DIG-466, DIG-467, DIG-469, DIG-474, DIG-482, DIG-485, or DIG-487 toxin for characterization and insect bioassay was accomplished by shake-flask-grown *P. fluorescens* strains harboring expression constructs. Seed cultures grown in M9 medium supplemented with 1% glucose and trace elements were used to inoculate 50 mL of defined minimal medium with 5% glycerol (Teknova Cat. #3D7426, Hollister, Calif.). Expression of the insecticidal protein toxin gene via the Ptac promoter was induced by addition of isopropyl-β-D-1-thiogalactopyranoside (IPTG) after an initial incubation of 24 hours at 30° C. with shaking. Cultures were sampled at the time of induction and at various times post-induction. Cell density was measured by optical density at 600 nm ($OD_{600}$). Other culture media suitable for growth of *Pseudomonas fluorescens* may also be utilized, for example, as described in Huang et al., 2007 and US Patent Application 20060008877.

Cell Fractionation and SDS-PAGE Analysis of Shake Flask Samples.

At each sampling time, 0.5 mL aliquots were centrifuged at 14000× g for five minutes. The cell pellets were frozen at −80° C. Soluble and insoluble fractions from frozen shake flask cell pellet samples were generated using BugBuster Master Mix (EMDMillipore® Darmstadt, Germany). Each cell pellet was resuspended in 0.5 mL BugBuster Master Mix™ solution and incubated with shaking at room temperature for 30 minutes. The samples were lysed using a beadbeater with 0.1 mm glass beads for 3 minutes. The lysate was centrifuged at 14,000 rpm for 5 minutes and the supernatant was recovered as the soluble fraction. The pellet (insoluble fraction) was then resuspended in an equal volume of extraction buffer (8 M urea, 0.5 M NaCl, 25 mM NaPO4, pH 10.4).

Samples were mixed 1:1 with 2× NuPAGE Tris Glycine SDS Sample Buffer (Invitrogen, Carlsbad, Calif.) containing dithiothreitol (DTT) and boiled for 5 minutes prior to loading onto Novex 4-20% Tris Glycine SDS polyacrylamide gel (Invitrogen, Carlsbad, Calif.). Electrophoresis was performed in the recommended Tris-Glycine buffer. Gels were stained with Bio-Safe Coomassie Stain according to the manufacturer's (Bio-Rad Inc., Hercules, Calif.) protocol and imaged using the GE Typhoon Series Imaging system (Pittsburgh, Pa.).

Inclusion Body Preparation.

Cry protein inclusion body (IB) preparations were performed on cells from *P. fluorescens* fermentations that produced insoluble B.t. insecticidal protein, as demonstrated by SDS-PAGE and MALDI-MS (Matrix Assisted Laser Desorption/Ionization Mass Spectrometry). *P. fluorescens* fermentation pellets were thawed in a 37° C. water bath. The cells were resuspended to 25% w/v in lysis buffer (50 mM Tris, pH 7.5, 200 mM NaCl, 20 mM EDTA disodium salt (Ethylenediaminetetraacetic acid), 1% Triton X-100, and 5 mM Dithiothreitol (DTT); 5 mL/L of bacterial protease inhibitor cocktail (P8465 Sigma-Aldrich, St. Louis, Mo.) were added just prior to use). The cells were suspended using a hand-held homogenizer at the lowest setting (Tissue Tearor, BioSpec Products, Inc Bartlesville, Okla.). Lysozyme (25 mg of Sigma-Aldrich L7651, from chicken egg white) was added to the cell suspension by mixing with a metal spatula, and the suspension was incubated at room temperature for one hour. The suspension was cooled on ice for 15 minutes, then sonicated using a Branson Sonifier 250 (two 1-minute sessions, at 50% duty cycle, 30% output). Cell lysis was checked by microscopy. An additional 25 mg of lysozyme was added if necessary, and the incubation and sonication were repeated. When cell lysis was confirmed via microscopy, the lysate was centrifuged at 11,500× g for 25 minutes (4° C.) to form the IB pellet, and the supernatant was discarded. The IB pellet was suspended with 100 mL lysis buffer, homogenized with the hand-held mixer and centrifuged as above. The IB pellet was repeatedly washed by suspension (in 50 mL lysis buffer), homogenization, sonication, and centrifugation until the supernatant became colorless and the IB pellet became firm and off-white in color. For the final wash, the IB pellet was suspended in sterile-filtered (0.22 μm) distilled water containing 2 mM EDTA, and centrifuged. The final pellet was suspended in sterile-filtered distilled water containing 2 mM EDTA, and stored in 1 mL aliquots at −80° C.

SDS-PAGE analysis and quantification of protein in IB preparations was done by thawing a 1 mL aliquot of IB pellet and diluting 1:20 with sterile-filtered distilled water. The diluted sample was then boiled with 4× reducing sample buffer [250 mM Tris, pH 6.8, 40% glycerol (v/v), 0.4% Bromophenol Blue (w/v), 8% SDS (w/v) and 8% β-Mercapto-ethanol (v/v)] and loaded onto a Novex® 4-20% Tris-Glycine, 12+2 well gel (Invitrogen) run with 1× Tris/Glycine/SDS buffer (BioRad). The gel was run for 60 min at 200 volts then stained with Coomassie Blue (50% G-250/50% R-250 in 45% methanol, 10% acetic acid), and destained with 7% acetic acid, 5% methanol in distilled water. Quantification of target bands was done by comparing densitometric values for the bands against Bovine Serum Albumin (BSA) samples run on the same gel to generate a standard curve.

Solubilization of Inclusion Bodies.

Six mL of inclusion body suspension from Pf clone containing DIG-465, DIG-473, DIG-468, DIG-483, DIG-462, DIG-463, DIG-464, DIG-466, DIG-467, DIG-469, DIG-474, DIG-482, DIG-485, or DIG-487 protein were centrifuged on the highest setting of an Eppendorf model 5415C microfuge (approximately 14,000× g) to pellet the inclusions. The storage buffer supernatant was removed and replaced with 25 mL of 100 mM sodium carbonate buffer, pH 11, in a 50 mL conical tube. Inclusions were resuspended using a pipette and vortexed to mix thoroughly. The tube was placed on a gently rocking platform at 4° C. overnight to extract the target protein. The extract was centrifuged at 30,000× g for 30 min at 4° C., and the resulting supernatant was concentrated 5-fold using an Amicon Ultra-15 regenerated cellulose centrifugal filter device (30,000 Molecular Weight Cutoff; Millipore). The sample buffer was then changed to 10 mM CAPS [3-(cyclohexamino)1-propanesulfonic acid] pH 10, using disposable PD-10 columns (GE Healthcare, Piscataway, N.J.).

Gel Electrophoresis.

The concentrated extract was prepared for electrophoresis by diluting 1:50 in NuPAGE® LDS sample buffer (Invitrogen) containing 5 mM dithiothreitol as a reducing agent and heated at 95° C. for 4 minutes. The sample was loaded in duplicate lanes of a 4-12% NuPAGE® gel alongside five BSA standards ranging from 0.2 to 2 μg/lane (for standard curve generation). Voltage was applied at 200V using MOPS SDS running buffer (Invitrogen) until the tracking dye reached the bottom of the gel. The gel was stained with 0.2% Coomassie Blue G-250 in 45% methanol, 10% acetic acid, and destained, first briefly with 45% methanol, 10% acetic acid, and then at length with 7% acetic acid, 5% methanol until the background cleared. Following destaining, the gel was scanned with a Biorad Fluor-S MultiImager. The instrument's Quantity One v.4.5.2 Software was used to obtain background-subtracted volumes of the stained protein bands and to generate the BSA standard curve that was used to calculate the concentration of DIG-465, DIG-473, DIG-468, DIG-483, DIG-462, DIG-463, DIG-464, DIG-466, DIG-467, DIG-469, DIG-474, DIG-482, DIG-485, or DIG-487 protein in the stock solution.

The level of expression of DIG-465, DIG-473, DIG-468, DIG-483, DIG-463, DIG-464, DIG-466, DIG-467, DIG- 469, DIG-474, DIG-482, DIG-485, and DIG-487 was compared to the level of expression of truncated Cry1Ca (DIG-462) when expressed in *Pseudomonas fluorescens* bacterial cells. Truncated Cry1Ca (DIG-462) expressed at approximately 1 g/l, whereas DIG-473 expressed at approximately 0.5 g/l. DIG-465 expressed at approximately 5-fold higher than truncated Cry1Ca, at 4.9 g/l. These in vitro results show that the L57A mutation results in greater expression of truncated Cry1Ca protein.

EXAMPLE 3

Insecticidal Activity of DIG Proteins Produced in *Pseudomonas Fluorescens*

B.t. insecticidal toxins DIG-462, DIG-463, DIG-464, DIG-465, DIG-466, DIG-467, DIG-468, DIG-469, DIG-470, DIG-473, and DIG-474 were demonstrated to be active on Lepidopteran species including diamondback moth (DBM; *Plutella xylostella* (Linnaeus)) and fall armyworm (FAW, *Spodoptera frugiperda* (Smith)).

Sample Preparation and Bioassays.

Inclusion body preparations in 10 mM CAPS pH10 were diluted appropriately in 10 mM CAPS, pH 10, and all bioassays contained a control treatment consisting of this buffer, which served as a background check for mortality or growth inhibition.

Protein concentrations in bioassay buffer were estimated by gel electrophoresis using BSA to create a standard curve for gel densitometry, which was measured using a BioRad imaging system (Fluor-S MultiImager with Quantity One software version 4.5.2). Proteins in the gel matrix were stained with Coomassie Blue-based stain and destained before reading.

Purified proteins were tested for insecticidal activity in bioassays conducted with neonate Lepidopteran larvae on artificial insect diet. Larvae of DBM and FAW were hatched from eggs obtained from a colony maintained by a commercial insectary (Benzon Research Inc., Carlisle, Pa.). Larvae of rFAW were hatched from eggs harvested from a proprietary colony (Dow AgroSciences LLC, Indianapolis, Ind.).

These bioassays were conducted in 128-well plastic trays specifically designed for insect bioassays (C-D International, Pitman, N.J.). Each well contained 1.0 mL of multi-species *Lepidoptera* diet (Southland Products, Lake Village, Ark.). A 40 μL aliquot of protein sample was delivered by pipette onto the 1.5 $cm^2$ diet surface of each well (26.7 $\mu L/cm^2$). Cry protein concentrations were calculated as the amount (ng) of DIG protein per square centimeter ($cm^2$) of surface area in the well. The treated trays were held in a fume hood until the liquid on the diet surface had evaporated or was absorbed into the diet.

Within a few hours of eclosion, individual larvae were picked up with a moistened camel hair brush and deposited on the treated diet, one larva per well. The infested wells were then sealed with adhesive sheets of clear plastic, vented to allow gas exchange (C-D International, Pitman, N.J.). Bioassay trays were held under controlled environmental conditions (28° C., ~60% Relative Humidity, 16:8 [Light: Dark]) for 5 days, after which the total number of insects exposed to each protein sample, the number of dead insects, and the weight of surviving insects were recorded. Percent mortality and percent growth inhibition were calculated for each treatment. Growth inhibition (GI) was calculated as follows:

$$GI=[1-(TWIT/TNIT)/(TWIBC/TNIBC)]$$

where TWIT is the Total Weight of Insects in the Treatment,

TNIT is the Total Number of Insects in the Treatment

TWIBC is the Total Weight of Insects in the Background Check (Buffer control), and TNIBC is the Total Number of Insects in the Background Check (Buffer control).

In the DBM bioassay, 10 and 300 ng/$cm^2$ of DIG-462, DIG-463, DIG-464, DIG-465, DIG-466, DIG-467, DIG-468, DIG-469, DIG-470, DIG-471, DIG-472, DIG-473, and DIG-474 were tested against the insect sp. The FAW were tested with inclusion body preparation of DIG-462, DIG-465, DIG-473 at 1× and 5× dilution rate. Percent mortality and growth inhibition results were compared.

Mortality was 100% at 300 ng/$cm^2$ for DIG-462, DIG-463, DIG-464, DIG-465, DIG-466, DIG-468, DIG-469, DIG-473, and DIG-474 treatments (Table 2 and Table 3). Growth inhibition was 70-90% inhibition of growth at 10 ng/$cm^2$ and 100% inhibition at 300 ng/$cm^2$ for DIG-465 and DIG-473 treatments (Table 2).

TABLE 2

Results of bioassay tests of DIG-462, DIG-465 and DIG-473 proteins on DBM, measuring both mortality and growth inhibition

| Protein | Mortality | Growth Inhibition |
|---|---|---|
| DIG-462 | +++ | ++++ |
| DIG-465 | ++ | ++++ |
| DIG-473 | +++ | ++++ |

For Mortality ++ = 0-20% at 10 ng/$cm^2$ and 100% at 300 ng/$cm^2$, +++ = 30-60% at 10 ng/$cm^2$ and 100% at 300 ng/$cm^2$.

For Growth Inhibition ++++ = 70-90% inhibition of growth at 10 ng/$cm^2$ and 100% inhibition at 300 ng/$cm^2$.

TABLE 3

Bioassay results of protein mutants tested against DBM at 10 ng/$cm^2$ and 300 ng/$cm^2$ concentrations.

| Protein | % Mortality at 10 ng/$cm^2$ | % Mortality at 300 ng/$cm^2$ |
|---|---|---|
| DIG-462 | 38 | 100 |
| DIG-463 | 63 | 100 |
| DIG-464 | 38 | 100 |
| DIG-465 | 0 | 100 |
| DIG-466 | 38 | 100 |
| DIG-467 | 38 | 88 |
| DIG-468 | 13 | 100 |
| DIG-469 | 0 | 100 |
| DIG-470 | 0 | 50 |
| DIG-471 | 0 | 0 |
| DIG-472 | 0 | 0 |
| DIG-473 | 38 | 100 |
| DIG-474 | 0 | 100 |
| BSA | 0 | 0 |

Growth inhibition of Cry1Ca core toxin (DIG-462), DIG-465, and DIG-473 protein to FAW larvae was determined to be >40% for all treatments (Table 4). Proteins were tested at full strength and diluted 5-fold with buffer (10 mM CAPS, pH 10).

TABLE 4

| Percent growth inhibition of DIG-462, DIG-465, and DIG-473 to FAW | | |
|---|---|---|
| Protein | Dilution | % Growth Inhibition |
| DIG-462 | 1X | 43 |
| DIG-462 | 5X | 47 |
| DIG-465 | 1X | 81 |
| DIG-465 | 5X | 58 |
| DIG-473 | 1X | 56 |
| DIG-473 | 5X | 48 |
| Buffer | 1X | 0 |

DBM activity and the susceptibility of the purified protein to be digested by chymotrypsin were assessed. An unexpected and surprising finding was that DIG-473 was resistant to chymotrypsin cleavage while at the same time having the same potency against DBM as DIG-462. This is in contrast to the Cry1Ca core (DIG-462) and DIG-465 proteins, which were susceptible to chymotrypsin cleavage in vitro (Table 5).

TABLE 5

| Proteins with activity against DBM (DIG-462 is the standard) and protein resistance to cleavage by Chymotrypsin. | | | |
|---|---|---|---|
| DIG # | Mutation Type | Activity on DBM | Resistant to Chymotrypsin |
| 462 | truncated | ++++ | No |
| 463 | G54A | ++++ | No |
| 464 | L57M | ++++ | No |
| 465 | L57A | ++++ | No |
| 466 | V68F | ++++ | No |
| 467 | V68I | ++++ | No |
| 468 | ΔGPS | +++ | No |
| 469 | W73A | +++ | Partial |
| 473 | F596M | ++++ | Yes |
| 474 | F596A | ++++ | No |
| 482 | G54A/W73M | +++ | Yes |
| 483 | G54A/ΔGPS | +++ | Yes |
| 485 | L57A/ΔGPS | +++ | No |
| 487 | L57M/ΔGPS | +++ | No |

EXAMPLE 4

European Corn Borer (ECB), Southwestern Corn Borer (SWCB) and Southern Armyworm (SAW) Bioassays Bioassays were conducted in 32-well test trays. Approximately 5 mL of a 2% water-agar solution was applied to each well and the agar was allowed to solidify completely.

Plants were approximately 3 weeks old and tested at $T_1$ generation. Three replicates of $T_1$ leaf material were completed. One leaf was cut (1"×0.5" rectangular) and placed in a single well of the tray. Each well was infested with 10 individual insect larvae (usually less than 24 hours old) of the ECB, Cry1Fa rECB or SWCB. For SAW, 5 individual insect larvae were infested per well. Seed based plants originated from B104 inbred lines and Yellow Fluorescent Protein (YFP) transformed plants served as negative controls.

The infested wells were then sealed with adhesive sheets of clear plastic, vented to allow gas exchange (C-D International, Pitman, N.J.). Trays were placed in a conviron incubator and maintained at 28° C. (16:8 h light:dark, 60% RH) for 3 days, after which the total amount of damage to each leaf piece (0, 5, 10, 15, 25, 50, 75% damage, etc., up to 100%) was recorded.

There was reduced feeding damage caused by ECB and Cry1Fa resistant ECB (rECB) when the insect larvae were exposed to plants containing truncated Cry1Ca modified protein. When tested in a diet bioassay, where purified full length Cry1Ca is placed on top of an artificial insect diet and individual insects are allowed to feed on the diet containing the toxin, modified Cry1Ca is found to be inactive against ECB and rECB. However, when expressed in maize, at concentrations of >120 ng/cm$^2$, the expression of Cry1Ca in the plant provides unexpected protection against feeding damage caused by ECB and especially rECB.

TABLE 6

| Bioassay results of IRDIG544.12 $T_1$ maize when fed to European Corn Borer (ECB) and Cry1Fa-resistant ECB (rECB) | | | | |
|---|---|---|---|---|
| Plant Name | Description | ECB Avg. Damage | rECB Avg. Damage | Toxinng/cm$^2$ |
| YFP negative control | control | 100 | 88.3 | 0 |
| YFP negative control | control | 100 | 93.3 | 0 |
| YFP negative control | control | 97.7 | 98.3 | 0 |
| YFP negative control | control | 99.3 | 98 | 0 |
| YFP negative control | control | 100 | 92.7 | 0 |
| 114269[1]-021.001AJ.025 | IRDIG544.12 w/TraP12 | 96 | 85 | 41 |
| 114269[1]-021.001AJ.018 | IRDIG544.12 w/TraP12 | 94.3 | 90 | 42 |
| 114269[1]-021.001AJ.017 | IRDIG544.12 w/TraP12 | 99.3 | 95 | 34 |
| 114269[1]-021.001AJ.023 | IRDIG544.12 w/TraP12 | 99.3 | 50 | 36 |
| 114269[1]-021.001AJ.016 | IRDIG544.12 w/TraP12 | 99.3 | 80 | 33 |
| 114260[1]-021.AJ001.023 | IRDIG544.12 | 66.7 | 11.7 | 210 |
| 114260[1]-021.AJ001.029 | IRDIG544.12 | 69.7 | 13.3 | 230 |
| 114260[1]-021.AJ001.021 | IRDIG544.12 | 66.7 | 16.7 | 210 |
| 114260[1]-021.AJ001.016 | IRDIG544.12 | 50 | 18.3 | 230 |
| 114260[1]-021.AJ001.019 | IRDIG544.12 | 50 | 18.3 | 210 |

TABLE 6-continued

Bioassay results of IRDIG544.12 $T_1$ maize when fed to European Corn Borer (ECB) and Cry1Fa-resistant ECB (rECB)

| Plant Name | Description | ECB Avg. Damage | rECB Avg. Damage | Toxinng/cm$^2$ |
|---|---|---|---|---|
| 114259[1]-009.AJ001.018 | IRDIG544.12 | 95 | 85 | 100 |
| 114259[1]-009.AJ001.022 | IRDIG544.12 | 86 | 61.7 | 130 |
| 114259[1]-009.AJ001.021 | IRDIG544.12 | 93.3 | 75 | 140 |
| 114259[1]-009.AJ001.026 | IRDIG544.12 | 80 | 95 | 67 |
| 114259[1]-009.AJ001.027 | IRDIG544.12 | 100 | 61.7 | 92 |
| 114260[1]-010.001AJ.054 | IRDIG544.12 | 68.3 | 25 | 180 |
| 114260[1]-010.001AJ.048 | IRDIG544.12 | 71.7 | 18.3 | 180 |
| 114260[1]-010.001AJ.047 | IRDIG544.12 | 66.7 | 50 | 140 |
| 114260[1]-010.001AJ.052 | IRDIG544.12 | 71.7 | 20 | 220 |
| 114260[1]-010.001AJ.046 | IRDIG544.12 | 86.7 | 16.7 | 200 |
| 114269[1]-029.001AJ.027 | IRDIG544.12 w/TraP12 | 91 | 66.7 | 39 |
| 114269[1]-029.001AJ.028 | IRDIG544.12 w/TraP12 | 88.3 | 66.7 | 30 |
| 114269[1]-029.001AJ.023 | IRDIG544.12 w/TraP12 | 96.7 | 88.3 | 41 |
| 114269[1]-029.001AJ.026 | IRDIG544.12 w/TraP12 | 96 | 76.7 | 37 |
| 114269[1]-029.001AJ.019 | IRDIG544.12 w/TraP12 | 96.7 | 95 | 41 |
| 114267[1]-009.001AJ.044 | IRDIG544.12 w/TraP12 | 95 | 70 | 36 |
| 114267[1]-009.001AJ.034 | IRDIG544.12 w/TraP12 | 88.3 | 56.7 | 44 |
| 114267[1]-009.001AJ.032 | IRDIG544.12 w/TraP12 | 96.7 | 86.7 | 41 |
| 114267[1]-009.001AJ.037 | IRDIG544.12 w/TraP12 | 96.7 | 88.3 | 43 |
| 114267[1]-009.001AJ.030 | IRDIG544.12 w/TraP12 | 91.7 | 80 | 43 |
| 114259[1]-006.001AJ.015 | IRDIG544.12 | 91.7 | 90 | 38 |
| 114259[1]-006.001AJ.014 | IRDIG544.12 | 98.3 | 85 | 41 |
| 114259[1]-006.001AJ.005 | IRDIG544.12 | 95 | 80 | 40 |
| 114259[1]-006.001AJ.010 | IRDIG544.12 | 81.7 | 86 | 39 |
| 114259[1]-006.001AJ.013 | IRDIG544.12 | 85 | 88.3 | 47 |
| 114270[1]-027.AJ001.029 | IRDIG544.12 w/TraP12 | 98.7 | 96.7 | 170 |
| 114270[1]-027.AJ001.030 | IRDIG544.12 w/TraP12 | 91.7 | 99.3 | 150 |
| 114270[1]-027.AJ001.023 | IRDIG544.12 w/TraP12 | 93.3 | 95 | 170 |
| 114270[1]-027.AJ001.028 | IRDIG544.12 w/TraP12 | 96.7 | 85 | 160 |
| 114270[1]-027.AJ001.027 | IRDIG544.12 w/TraP12 | 98.3 | 86.7 | 150 |
| 114257[1]-016.AJ001.030 | IRDIG544.12 | 100 | 86.7 | 100 |
| 114257[1]-016.AJ001.024 | IRDIG544.12 | 68.3 | 97 | 140 |
| 114257[1]-016.AJ001.021 | IRDIG544.12 | 100 | 99.3 | 130 |
| 114257[1]-016.AJ001.027 | IRDIG544.12 | 100 | 71.7 | 130 |
| 114257[1]-016.AJ001.022 | IRDIG544.12 | 100 | 81.7 | 120 |
| 114267[1]-021.AJ001.039 | IRDIG544.12 w/TraP12 | 91.7 | 61.7 | 230 |
| 114267[1]-021.AJ001.034 | IRDIG544.12 w/TraP12 | 95 | 80 | 180 |
| 114267[1]-021.AJ001.044 | IRDIG544.12 w/TraP12 | 83.3 | 75 | 210 |
| 114268[1]-023.AJ001.036 | IRDIG544.12 w/TraP12 | 81 | 99 | 320 |
| 114268[1]-023.AJ001.041 | IRDIG544.12 w/TraP12 | 100 | 83.3 | 410 |
| 114268[1]-023.AJ001.034 | IRDIG544.12 w/TraP12 | 93.3 | 55 | 520 |
| 114268[1]-023.AJ001.039 | IRDIG544.12 w/TraP12 | 91.7 | 80 | 620 |
| 114268[1]-023.AJ001.026 | IRDIG544.12 w/TraP12 | 98.3 | 96 | 440 |
| 114268[1]-026.AJ001.053 | IRDIG544.12 w/TraP12 | 90 | 73.3 | 390 |
| 114268[1]-026.AJ001.046 | IRDIG544.12 w/TraP12 | 90 | 84.3 | 500 |
| 114268[1]-026.AJ001.037 | IRDIG544.12 w/TraP12 | 99.3 | 71.7 | 320 |
| 114268[1]-026.AJ001.038 | IRDIG544.12 w/TraP12 | 91.7 | 65 | 320 |

TABLE 6-continued

| Bioassay results of IRDIG544.12 $T_1$ maize when fed to European Corn Borer (ECB) and Cry1Fa-resistant ECB (rECB) | | | | |
|---|---|---|---|---|
| Plant Name | Description | ECB Avg. Damage | rECB Avg. Damage | Toxinng/cm$^2$ |
| 114268[1]-026.AJ001.052 | IRDIG544.12 w/TraP12 | 97.7 | 66.7 | 360 |
| 114271[1]-011.001AJ.031 | IRDIG544.12 w/TraP12 | 100 | 95 | 4 |
| 114271[1]-011.001AJ.042 | IRDIG544.12 w/TraP12 | 100 | 95 | 4 |
| 114271[1]-011.001AJ.043 | IRDIG544.12 w/TraP12 | 96 | 91.7 | 4 |
| 114271[1]-011.001AJ.047 | IRDIG544.12 w/TraP12 | 100 | 97.7 | 3 |
| 114271[1]-011.001AJ.046 | IRDIG544.12 w/TraP12 | 100 | 98 | 3 |
| 114270[1]-023.001AJ.050 | IRDIG544.12 w/TraP12 | 90 | 80 | 210 |
| 114270[1]-023.001AJ.055 | IRDIG544.12 w/TraP12 | 99.3 | 73.3 | 260 |
| 114270[1]-023.001AJ.044 | IRDIG544.12 w/TraP12 | 100 | 92 | 250 |
| 114270[1]-023.001AJ.054 | IRDIG544.12 w/TraP12 | 100 | 88.3 | 210 |
| 114270[1]-023.001AJ.058 | IRDIG544.12 w/TraP12 | 100 | 82.7 | 140 |
| B104 | control | 100 | 100 | 0 |
| B104 | control | 100 | 100 | 0 |
| B104 | control | 100 | 100 | 0 |
| B104 | control | 100 | 99.3 | 0 |
| B104 | control | 100 | 86 | 0 |

Reduced feeding damage caused by southwestern corn borer (SWCB) and southern armyworm (SAW) was observed when the insect larvae were exposed to plants containing truncated Cry1Ca modified protein, at a range of protein expression from 140-340 ng/cm$^2$ (Table 7). The average expression was 210 ng/cm$^2$ with a standard deviation of 35.

TABLE 7

| Bioassay of IRDIG544.12 $T_1$ maize plants when fed to southwestern corn borer (SWCB) and southern army worm (SAW) | | |
|---|---|---|
| Plant Name | SWCB Avg. Dmg. | SAW Avg. Dmg. |
| 112726[1]-015.AJ001.047 | 2 | 3.0 |
| 112726[1]-015.AJ001.030 | 4 | 3.0 |
| 112726[1]-015.AJ001.019 | 1 | 1.3 |
| 112726[1]-015.AJ001.034 | 2 | 2.0 |
| YFP negative control | 98.3 | 94.3 |
| YFP negative control | 93.3 | 62.5 |
| YFP negative control | 100 | 27.5 |
| YFP negative control | 92.7 | 67.5 |
| YFP negative control | 97.7 | 30.0 |
| YFP negative control | 100 | 45.0 |
| B104 | 98.3 | 94.3 |
| B104 | 100 | 91.7 |
| B104 | 100 | 97.0 |
| B104 | 65 | 70.0 |
| B104 | 100 | 86.7 |

Field trials on corn borers were conducted at two locations: one in Indiana (IN), United States and the other in Mississippi (MS), United States. Multiple constructs and events were tested for each treatment. Cry1Ab and Cry1F served as positive controls in the ECB trials. The null served as a negative control.

To assess ECB efficacy, each plant received ten second-instar ECB larvae in the whorl of V6-V7 stage plants. In MS, Southwestern corn borer (SWCB) second-instar larvae were also artificially infested in the whorls of V9 corn (22 larvae per plant). The ECB and SWCB used were obtained from Benzon laboratory. In both ECB trials, plants were evaluated 2 weeks after infestation for foliar damage (Guthrie 1-9 scale) (Guthrie et al. 1960) where 1 is no visible injury and 9 is most leaves with long lesions (Table 8). In the MS SWCB trials, the plants were examined 4-5 days after the whorl rating for stalk damage and live insects. Data collected included number of tunnels per stalk, length of tunnels and live larvae/pupae per stalk.

TABLE 8

| Corn Borer damage score criterion (whorl damage). | |
|---|---|
| Score | Criterion |
| 1 | No visible leaf injury or small amount of shot hole type injury on a few leaves. |
| 2 | Small amount of shot-hole type lesions on a few leaves. |
| 3 | Shot-hole injury common on several leaves. |
| 4 | Several leaves with shot-holes and elongated lesions. |
| 5 | Several leaves with elongated lesions. |
| 6 | Several leaves with elongated lesions (ca. 1 inch). |
| 7 | Long lesions common on one-half of the leaves. |
| 8 | Long lesions common on about ⅔ of the leaves. |
| 9 | Most leaves with long lesions. |

ECB Field Trials. ECB whorl damage was measured for Cry1Ca activity and showed significantly better whorl protection when compared to the null. Cry1Ca event activities were not statistically equivalent to the whorl protection provided by Cry1Ab and Cry1F.

Data generated in MS further reinforced the unexpected high level of plant protection for Cry1Ca. High feeding pressure was established in this study. Significant control was measured for Cry1Ca when compared to foliar and stalk damage on the null. Very few live insects were found surviving in the Cry1Ca stalks. Significant whorl and stalk protection was measured for Cry1Ab and Cry1F events when compared to the null.

TABLE 9

ECB Foliar Whorl Data, IN (Average Across Multiple Events)

| Gene | Events | Avg. Whorl Damage Rating (1-9 rating) | Range of means |
|---|---|---|---|
| Cry1Ca | 4 | 2.31 B | 2.00-2.65 |
| Cry1Ab | 8 | 1.00 A | 1.00 |
| Cry1F | 12 | 1.03 A | 1.00-1.20 |
| Null | 1 | 4.65 C | |

Means followed by different letters are significantly different ($P \leq 0.05$).

TABLE 10

ECB Foliar Whorl and Stalk Data, MS (Average Across Multiple Events)

| Toxin Gene | Number of Events | Avg. Whorl Damage Rating (1-9) | Avg. # Tunnels Per Stalk | Avg. Length (cm) of Tunnels | Avg. # of Larvae + Pupae Per Stalk |
|---|---|---|---|---|---|
| Cry1Ca | 3 | 2.74 B | 0.53 B | 1.43 B | 0.25 B |
| Cry1Ab | 8 | 1.66 D | 0.00 C | 0.00 C | 0.00 C |
| Cry1F | 8 | 1.85 C | 0.00 C | 0.00 C | 0.00 C |
| Null | 1 | 6.77 A | 1.93 A | 9.15 A | 1.89 A |

For all data columns, all gene events were significantly different from the null values ($P < 0.05$).
Within each column, means followed by different letters are significantly different ($P \leq 0.05$).

In the SWCB trial, only 2 events per B.t. were evaluated. High feeding pressure was established in this study. Statistically equivalent stalk protection and number of larvae and pupae per stalk were measured for Cry1Ab, Cry1F, and Cry1Ca events.

TABLE 11

SWCB Foliar Whorl and Stalk Data, MS

| Toxin Gene | Number of Events | Avg. Whorl Damage Rating (1-9) | Avg. # Tunnels Per Stalk | Avg. Length (cm) of Tunnels | Avg. # of Larvae + Pupae Per Stalk |
|---|---|---|---|---|---|
| Cry1Ca | 2 | 1.90 C | 0.07 B | 0.20 B | 0.02 B |
| Cry1Ab | 2 | 1.91 C | 0.00 B | 0.00 B | 0.00 B |
| Cry1F | 2 | 2.18 B | 0.07 B | 0.54 B | 0.03 B |
| Null | 1 | 7.17 A | 3.53 A | 28.62 A | 3.06 A |

Within each column, means followed by different letters are significantly different ($P \leq 0.05$).

The active form of Cry1Ca is composed of amino acids 29-628. The full length (1-1164), or cleaved forms (1-628 and 29-628) are active when presented to insects, since they are processed to the 29-628 form.

EXAMPLE 5

Corn Earworm Field Trials

Field trials on corn earworm were conducted in Fowler, Ind. with multiple constructs and events (SEQ ID NO:31). The null served as a negative control. Each plant received five first instar larvae in the green silks of corn ears. CEW were obtained from Benzon Laboratory. Ten corn ears per plot per event were evaluated to assess the level of kernel damage in corn ears infested with CEW. All transgenic events provided significantly lower levels of kernel damage when compared to the null. There was significant suppression of larval feeding on Cry1Ca plants (Table 12).

TABLE 12

CEW Kernel Consumption Data, IN

| Gene | Entries | Avg. area ($cm^2$) of kernel consumed* | % reduction in area consumed kernels (compared to null) |
|---|---|---|---|
| Cry1Ca | 4 | 1.72 B | 63.2 |
| Cry1F | 12 | 1.86 B | 60.3 |
| Null | 1 | 4.68 A | |

EXAMPLE 6

*Agrobacterium* Transformation

Standard cloning methods were used in the construction of binary plant transformation and expression plasmids. *Agrobacterium* binary plasmids which contained the cry1Ca expression cassettes were engineered using Gateway® Technology (Invitrogen, Carlsbad, Calif.) and used in *Agrobacterium*-mediated plant transformation. Restriction endonucleases were obtained from New England BioLabs (NEB; Ipswich, Mass.) and T4 DNA Ligase (Invitrogen) were used for DNA ligation. Gateway reactions were performed using Gateway® LR Clonase® enzyme mix (Invitrogen) Plasmid preparations were performed using the NucleoSpin® Plasmid Preparation kit or the NucleoBond® AX Xtra Midi kit (both from Macherey-Nagel), following the instructions of the manufacturers. DNA fragments were purified using the QIAquick PCR Purification Kit or the QIAEX II Gel Extraction Kit (both from Qiagen) after gel isolation.

DNA fragments comprising the nucleotide sequences that encode the insecticidal proteins, or fragments thereof, were synthesized by a commercial vendor (e.g. DNA2.0, Menlo Park, Calif.) and supplied as cloned fragments in standard plasmid vectors, or were obtained by standard molecular biology manipulation of other constructs containing appropriate nucleotide sequences. Unique restriction sites internal to each gene was identified and a fragment of each gene synthesized, each containing a specific deletion or insertion. The modified Cry fragments were subcloned into other Cry fragments at an appropriate restriction site to obtain a region encoding the desired full-length protein, fused proteins, or deleted variant proteins.

Electro-competent cells of *Agrobacterium tumefaciens* strain Z707S (a streptomycin-resistant derivative of Z707; Hepburn et al., 1985) were prepared and transformed using electroporation (Weigel and Glazebrook, 2002). After electroporation, 1 mL of YEP broth (gm/L: yeast extract, 10; peptone, 10; NaCl, 5) was added to the cuvette and the cell-YEP suspension was transferred to a 15 mL culture tube for incubation at 28° C. in a water bath with constant agitation for 4 hours. The cells were plated on YEP plus agar (25 gm/L) with spectinomycin (200 μg/mL) and streptomycin (250 μg/mL) and the plates were incubated for 2-4 days at 28° C. Well separated single colonies were selected and streaked onto fresh YEP+agar plates with spectinomycin and streptomycin as before, and incubated at 28° C. for 1-3 days.

The presence of the insecticidal protein gene insert in the binary plant transformation vector was performed by PCR analysis using vector-specific primers with template plasmid DNA prepared from selected *Agrobacterium* colonies. The cell pellet from a 4 mL aliquot of a 15 mL overnight culture grown in YEP with spectinomycin and streptomycin as before was extracted using Qiagen Spin Mini Preps, performed per manufacturer's instructions. Plasmid DNA from the binary vector used in the *Agrobacterium* electroporation transformation was included as a control. The PCR reaction was completed using Taq DNA polymerase from Invitrogen per manufacturer's instructions at 0.5× concentrations. PCR reactions were carried out in a MJ Research Peltier Thermal Cycler programmed with the following conditions: Step 1) 94° C. for 3 minutes; Step 2) 94° C. for 45 seconds; Step 3) 55° C. for 30 seconds; Step 4) 72° C. for 1 minute per kb of expected product length; Step 5) 29 times to Step 2; Step 6) 72° C. for 10 minutes. The reaction was maintained at 4° C. after cycling. The amplification products were analyzed by agarose gel electrophoresis (e.g. 0.7% to 1% agarose, w/v) and visualized by ethidium bromide staining. A colony was selected whose PCR product was identical to the plasmid control.

TABLE 13

Description of plasmids for expressing DIG-465 and DIG-473 in maize.

| Plasmid | Description |
|---|---|
| pDAB115752 | ZmUbi1/DIG-465/ZmPer5::SCBV(MAM)v2/AAD-1v3/ZmLip |
| pDAB115753 | ZmUbi1/DIG-473/ZmPer5::SCBV(MAM)v2/AAD-1v3/ZmLip |
| pDAB112725 | ZmUbi1/Cry1Ca(Zm)/ZmPer5::SCBV(MAM)/AAD-1v3./ZmLip |
| pDAB112726 | ZmUbi1/Cry1Ca(HGC)/ZmPer5::SCBV(MAM)/AAD-1v3/ZmLip |

EXAMPLE 7

Production of DIG-465 and DIG-473 B.t. Insecticidal Proteins and Variants in Monocot Plants

*Agrobacterium*-Mediated Transformation of Maize.

Seeds from a High II $F_1$ cross (Armstrong et al., 1991) were planted into 5-gallon-pots containing a mixture of 95% Metro-Mix 360 soilless growing medium (Sun Gro Horticulture, Bellevue, Wash.) and 5% clay/loam soil. The plants were grown in a greenhouse using a combination of high pressure sodium and metal halide lamps with a 16:8 hour Light:Dark photoperiod. For obtaining immature $F_2$ embryos for transformation, controlled sib-pollinations were performed. Immature embryos were isolated at 8-10 days post-pollination when embryos were approximately 1.0 to 2.0 mm in size.

Infection and Co-Cultivation.

Maize ears were surface sterilized by scrubbing with liquid soap, immersing in 70% ethanol for 2 minutes, and then immersing in 20% commercial bleach (0.1% sodium hypochlorite) for 30 minutes before being rinsed with sterile water. A suspension *Agrobacterium* cells containing a superbinary vector was prepared by transferring 1-2 loops of bacteria grown on YEP solid medium containing 100 mg/L spectinomycin, 10 mg/L tetracycline, and 250 mg/L streptomycin at 28° C. for 2-3 days into 5 mL of liquid infection medium (LS Basal Medium (Linsmaier and Skoog, 1965), N6 vitamins (Chu et al., 1975), 1.5 mg/L 2,4-Dichlorophenoxyacetic acid (2,4-D), 68.5 gm/L sucrose, 36.0 gm/L glucose, 6 mM L-proline, pH 5.2) containing 100 μM acetosyringone. The solution was vortexed until a uniform suspension was achieved, and the concentration was adjusted to a final density of 200 Klett units, using a Klett-Summerson colorimeter with a purple filter. Immature embryos were isolated directly into a micro centrifuge tube containing 2 mL of the infection medium. The medium was removed and replaced with 1 mL of the *Agrobacterium* solution with a density of 200 Klett units, and the *Agrobacterium* and embryo solution was incubated for 5 minutes at room temperature and then transferred to co-cultivation medium (LS Basal Medium, N6 vitamins, 1.5 mg/L 2,4-D, 30.0 gm/L sucrose, 6 mM L-proline, 0.85 mg/L AgNO3, 100 μM Acetosyringone, 3.0 gm/L Gellan gum (PhytoTechnology Laboratories., Lenexa, Kans.), pH 5.8) for 5 days at 25° C. under dark conditions.

After co-cultivation, the embryos were transferred to selective medium after which transformed isolates were obtained over the course of approximately 8 weeks. For selection of maize tissues transformed with a superbinary plasmid containing a plant expressible pat or bar selectable marker gene, an LS based medium (LS Basal medium, N6 vitamins, 1.5 mg/L 2,4-D, 0.5 gm/L MES (2-(N-morpholino)ethanesulfonic acid monohydrate; PhytoTechnologies Labr.), 30.0 gm/L sucrose, 6 mM L-proline, 1.0 mg/L AgNO3, 250 mg/L cefotaxime, 2.5 gm/L Gellan gum, pH 5.7) was used with Bialaphos (Gold BioTechnology). The embryos were transferred to selection media containing 3 mg/L Bialaphos until embryogenic isolates were obtained. Recovered isolates were bulked up by transferring to fresh selection medium at 2-week intervals for regeneration and further analysis.

Regeneration and Seed Production.

For regeneration, the cultures were transferred to "28" induction medium (MS salts and vitamins, 30 gm/L sucrose, 5 mg/L Benzylaminopurine, 0.25 mg/L 2, 4-D, 3 mg/L Bialaphos, 250 mg/L cefotaxime, 2.5 gm/L Gellan gum, pH 5.7) for 1 week under low-light conditions (14 μEm-2s-1) then 1 week under high-light conditions (approximately 89 μEm-2s-1). Tissues were subsequently transferred to "36" regeneration medium (same as induction medium except lacking plant growth regulators). When plantlets grew to 3-5 cm in length, they were transferred to glass culture tubes containing SHGA medium (Schenk and Hildebrandt salts and vitamins (1972); PhytoTechnologies Labr.), 1.0 gm/L myo-inositol, 10 gm/L sucrose and 2.0 gm/L Gellan gum, pH 5.8) to allow for further growth and development of the shoot and roots. Plants were transplanted to the same soil mixture as described earlier herein and grown to flowering in the greenhouse. Controlled pollinations for seed production were conducted.

The level of expression of DIG-465 by construct 115752 and the level of expression of DIG-473 by construct 115753 is presented in FIG. 1. Both expressed similar levels of their respective proteins, at approximately 70-80 ng/cm$^2$ measured in leaves using a leaf punch to obtain the tissue sample.

SDS-PAGE of extract was taken from maize expressing the gene that encodes full length Cry1Ca protein (MR-1206) (mw 130 kDa). At least five protein products were detected by immune-blotting using a polyclonal antibody directed against Cry1Ca. The full length (130 kDa) protein, as encoded by the gene inserted into maize was detected. The other bands represent proteolytic products of this protein. A protein fragment composed of amino acid sequences 1-628, representing the core toxin was determined to have a molecular weight of 70 kDa. A 68 kDa band represented a protein composed of amino acids 29-628, where the first 28 amino acids from the N-terminus were deleted. The first three bands were functionally active against *S. frugiperda* and other lepidopteran insects. A fourth band represented a cleaved protein composed of amino acids 74-628 (mw 62 kDa), and a fifth band represented the Cry1Ca protein that was further processed to amino acids 74-596 (mw 59 kDa). The 62 kDa and 59 kDa bands were not functionally active against *S. frugiperda* and other lepidopteran insects, yet represent major protein products.

EXAMPLE 8

Bioassay of Transgenic Maize

Bioactivity of the DIG-465 and DIG-473 protein and variants produced in plant cells was demonstrated by methods known to those skilled in the art (see, for example Huang et al., 2006). Efficacy may be demonstrated by feeding various plant tissues or tissue pieces derived from a plant producing the DIG-465 or DIG-473 protein or variants to target insects in a controlled feeding environment. Alternatively, protein extracts may be prepared from various plant tissues derived from a plant producing the DIG-465 or DIG-473 protein or variants and incorporated in an artificial diet bioassay as previously described herein. It is to be understood that the results of such feeding assays are to be compared to similarly conducted bioassays that employ appropriate control tissues from host plants that do not produce the DIG-465 or DIG-473 protein or variants, or to other control samples.

Figure 2:
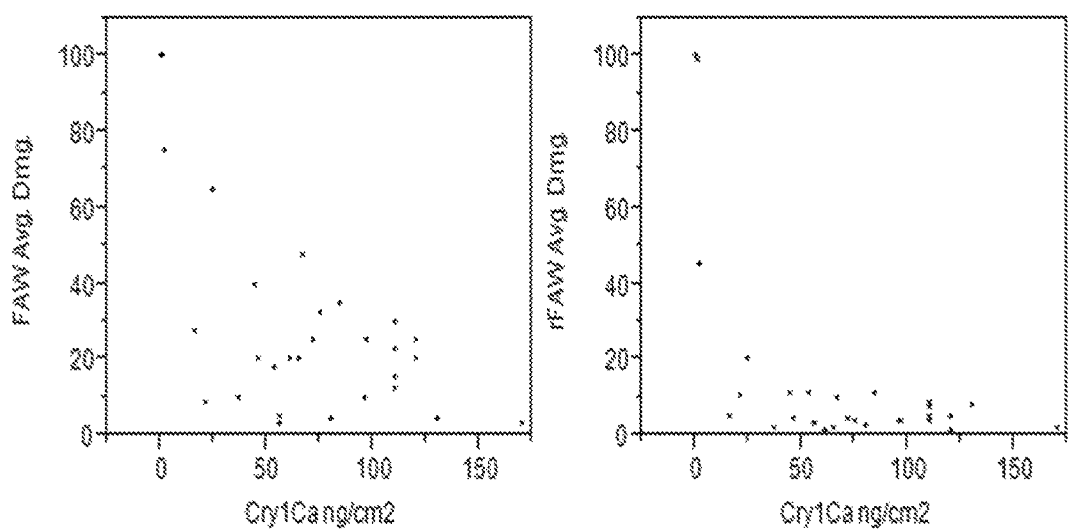
FIG. 2 is a plot of the amount of leaf damage in maize caused by FAW or Cry1Fa resistant FAW versus the level of expression of DIG-465.

The biological activity of various events produced in maize from construct 115752 (DIG-465) were tested for preventing leaf damage caused by the feeding activity of either FAW or Cry1Fa resistant FAW (rFAW). The results show that events that expressed DIG-465 protein exhibited less feeding damage than plants not expressing the protein, and that the effect was dose dependent, with higher expression of DIG-465 resulting in less feeding damage caused by either FAW or rFAW, with the affect apparently greater against rFAW (Table 14 and FIG. 2).

Figure 3:
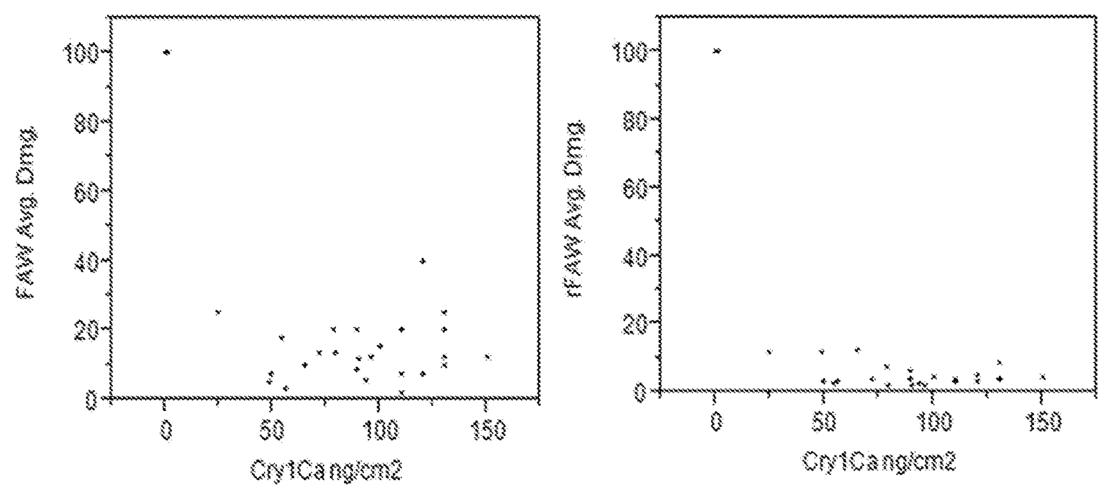
FIG. 3 is a plot of the amount of leaf damage in maize caused by FAW or Cry1Fa resistant FAW versus the level of expression of DIG-473.

Similarly, the biological activity of various events produced in maize from construct 115753 (DIG-473) were tested for preventing leaf damage caused by the feeding activity of either FAW or Cry1Fa resistant FAW (rFAW). The results show that events that expressed DIG-473 protein exhibited less feeding damage than plants not expressing the protein, and that the effect was dose dependent, with higher expression of DIG-473 resulting in less feeding damage caused by either FAW or rFAW, with the affect apparently greater against rFAW (Table 14 and FIG. 3).

TABLE 14

FAW bioassay data when exposed to DIG-465, DIG-473, or controls

| Plant Name | DIG # | FAW Avg. Dmg. | rFAW Avg. Dmg. | Accumulated toxin (ng/cm$^2$) |
|---|---|---|---|---|
| 115752[1]-001.001 | DIG-465 | 65 | 20 | 24 |
| 115752[1]-002.001 | DIG-465 | 20 | 4.375 | 46 |
| 115752[1]-003.001 | DIG-465 | 32.5 | 3.75 | 75 |
| 115752[1]-004.001 | DIG-465 | 100 | 98.75 | 0.7 |
| 115752[1]-005.001 | DIG-465 | 30 | 8.75 | 110 |
| 115752[1]-006.001 | DIG-465 | 40 | 11.25 | 44 |
| 115752[1]-007.001 | DIG-465 | 22.5 | 5 | 110 |
| 115752[1]-009.001 | DIG-465 | 3.125 | 3.125 | 56 |
| 115752[1]-010.001 | DIG-465 | 17.5 | 11.25 | 53 |
| 115752[1]-011.001 | DIG-465 | 3.125 | 1.75 | 170 |
| 115752[1]-012.001 | DIG-465 | 27.5 | 5 | 16 |
| 115752[1]-013.001 | DIG-465 | 20 | 1 | 61 |
| 115752[1]-014.001 | DIG-465 | 25 | 3.75 | 97 |
| 115752[1]-016.001 | DIG-465 | 15 | 3.75 | 110 |
| 115752[1]-017.001 | DIG-465 | 75 | 45 | 2 |
| 115752[1]-018.001 | DIG-465 | 25 | 4.375 | 72 |
| 115752[1]-019.001 | DIG-465 | 10 | 2.125 | 37 |
| 115752[1]-020.001 | DIG-465 | 25 | 1 | 120 |
| 115752[1]-021.001 | DIG-465 | 20 | 1.75 | 65 |
| 115752[1]-022.001 | DIG-465 | 12.5 | 7.5 | 110 |
| 115752[1]-023.001 | DIG-465 | 35 | 11.25 | 84 |
| 115752[1]-024.001 | DIG-465 | 47.5 | 10 | 67 |
| 115752[1]-025.001 | DIG-465 | 20 | 5 | 120 |
| 115752[1]-026.001 | DIG-465 | 4.375 | 8 | 130.00 |
| 115752[1]-027.001 | DIG-465 | 5 | 3.125 | 56 |
| 115752[1]-028.001 | DIG-465 | 10 | 3.75 | 96 |
| 115752[1]-029.001 | DIG-465 | 4.375 | 2.5 | 80 |
| 115752[1]-030.001 | DIG-465 | 8.75 | 10.625 | 21 |
| 115752[1]-031.001 | DIG-465 | 100 | 100 | 0 |
| 115753[1]-001.001 | DIG-473 | 100 | 100 | 0 |
| 115753[1]-002.001 | DIG-473 | 12.5 | 8.75 | 130 |
| 115753[1]-003.001 | DIG-473 | 20 | 7.5 | 78 |
| 115753[1]-004.001 | DIG-473 | 20 | 3.125 | 110 |
| 115753[1]-005.001 | DIG-473 | 25 | 11.875 | 24 |
| 115753[1]-006.001 | DIG-473 | 12.5 | 1.75 | 96 |
| 115753[1]-007.001 | DIG-473 | 8.75 | 3.75 | 89 |
| 115753[1]-008.001 | DIG-473 | 25 | 3.375 | 130 |
| 115753[1]-010.001 | DIG-473 | 20 | 6.25 | 89 |
| 115753[1]-011.001 | DIG-473 | 15 | 4.375 | 100 |
| 115753[1]-012.001 | DIG-473 | 13.75 | 2.125 | 79 |
| 115753[1]-013.001 | DIG-473 | 17.5 | 2.75 | 54 |
| 115753[1]-014.001 | DIG-473 | 10 | 12.5 | 65 |
| 115753[1]-015.001 | DIG-473 | 20 | 3.75 | 130 |
| 115753[1]-016.001 | DIG-473 | 7.5 | 3.125 | 49 |
| 115753[1]-017.001 | DIG-473 | 2.125 | 3.125 | 110 |
| 115753[1]-018.001 | DIG-473 | 100 | 100 | 0.7 |
| 115753[1]-019.001 | DIG-473 | 100 | 100 | 0 |
| 115753[1]-020.001 | DIG-473 | 11.875 | 1.75 | 90 |
| 115753[1]-021.001 | DIG-473 | 10 | 3.75 | 130 |
| 115753[1]-022.001 | DIG-473 | 40 | 5 | 120 |
| 115753[1]-023.001 | DIG-473 | 7.5 | 3.75 | 110 |
| 115753[1]-025.001 | DIG-473 | 13.75 | 3.375 | 72 |
| 115753[1]-026.001 | DIG-473 | 12.5 | 4.375 | 150 |
| 115753[1]-027.001 | DIG-473 | 5.625 | 2.5 | 93 |
| 115753[1]-028.001 | DIG-473 | 5 | 11.875 | 48 |
| 115753[1]-029.001 | DIG-473 | 3.125 | 3.125 | 56 |
| 115753[1]-030.001 | DIG-473 | 7.5 | 3.125 | 120.00 |
| B104 | | 100 | 100 | N/A |
| B104 | | 100 | 100 | N/A |
| B104 | | 100 | 100 | N/A |
| YFP negative control | | 100 | 100 | N/A |
| YFP negative control | | 100 | 100 | N/A |
| YFP negative control | | 100 | 100 | N/A |
| B104 | | 100 | 100 | N/A |
| B104 | | 100 | 100 | N/A |
| B104 | | 100 | 100 | N/A |
| YFP negative control | | 100 | 100 | N/A |
| YFP negative control | | 100 | 100 | N/A |
| YFP negative control | | 100 | 100 | N/A |

EXAMPLE 9

Production of Bt Insecticidal Proteins and Variants in Dicot Plants

*Arabidopsis* Transformation.

*Arabidopsis thaliana* Col-01 was transformed using the floral dip method (Weigel and Glazebrook, 2002). The selected *Agrobacterium* colony was used to inoculate 1 mL to 15 mL cultures of YEP broth containing appropriate antibiotics for selection. The culture was incubated overnight at 28° C. with constant agitation at 220 rpm. Each culture was used to inoculate two 500 mL cultures of YEP broth containing appropriate antibiotics for selection and the new cultures were incubated overnight at 28° C. with constant agitation. The cells were centrifuged at approximately 8700× g for 10 minutes at room temperature, and the resulting supernatant was discarded. The cell pellet was gently resuspended in 500 mL of infiltration media containing: ½× Murashige and Skoog salts (Sigma-Aldrich)/Gamborg's B5 vitamins (Gold BioTechnology, St. Louis, Mo.), 10% (w/v) sucrose, 0.044 μM benzylaminopurine (10 μL/L of 1 mg/mL stock in DMSO) and 300 μL/L Silwet L-77. Plants approximately 1 month old were dipped into the media for 15 seconds, with care taken to assure submergence of the newest inflorescence. The plants were then laid on their sides and covered (transparent or opaque) for 24 hours, washed with water, and placed upright. The plants were grown at 22° C., with a 16:8 light:dark photoperiod. Approximately 4 weeks after dipping, the seeds were harvested.

*Arabidopsis* Growth and Selection

Freshly harvested $T_1$ seed was allowed to dry for at least 7 days at room temperature in the presence of desiccant. Seed was suspended in a 0.1% agar/water (Sigma-Aldrich) solution and then stratified at 4° C. for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) was covered with fine vermiculite, sub-irrigated with Hoagland's solution (Hoagland and Arnon, 1950) until wet, then allowed to drain for 24 hours. Stratified seed was sown onto the vermiculite and covered with humidity domes (KORD Products, Bramalea, Ontario, Canada) for 7 days. Seeds were germinated and plants were grown in a Conviron (Models CMP4030 or CMP3244; Controlled Environments Limited, Winnipeg, Manitoba, Canada) under long day conditions (16:8 light: dark photoperiod) at a light intensity of 120-150 μmol/$m^2$sec under constant temperature (22° C.) and humidity (40-50%). Plants were initially watered with Hoagland's solution and subsequently with deionized water to keep the soil moist but not wet.

The domes were removed 5-6 days post sowing and plants were sprayed with a chemical selection agent to kill plants germinated from nontransformed seeds. For example, if the plant expressible selectable marker gene provided by the binary plant transformation vector was a pat or bar gene (Wehrmann et al., 1996), transformed plants may be selected by spraying with a 1000× solution of Finale (5.78% glufosinate ammonium, Farnam Companies Inc., Phoenix, Ariz.). Two subsequent sprays were performed at 5-7 day intervals. Survivors (plants actively growing) were identified 7-10 days after the final spraying and were transplanted into pots prepared with Sunshine Mix LP5. Transplanted plants were covered with a humidity dome for 3-4 days and placed in a Conviron incubator under the above-mentioned growth conditions.

Those skilled in the art of dicot plant transformation will understand that other methods of selection of transformed plants are available when other plant expressible selectable marker genes (e.g. herbicide tolerance genes) are used.

EXAMPLE 10

Transgenic *Glycine max* Comprising DIG Protein

Ten to 20 transgenic $T_0$ *Glycine max* plants harboring expression vectors for nucleic acids comprising Cry1Ca protein were generated as is known in the art, including for example by *Agrobacterium*-mediated transformation. Mature soybean (*Glycine max*) seeds were sterilized overnight with chlorine gas for sixteen hours. Following sterilization with chlorine gas, the seeds were placed in an open container in a LAMINAR™ flow hood to dispel the chlorine gas. Next, the sterilized seeds were imbibed with sterile $H_2O$ for sixteen hours in the dark using a black box at 24° C.

Preparation of split-seed soybeans. The split soybean seed comprising a portion of an embryonic axis protocol required preparation of soybean seed material which was cut longitudinally, using a #10 blade affixed to a scalpel, along the hilum of the seed to separate and remove the seed coat, and to split the seed into two cotyledon sections. Careful attention was made to partially remove the embryonic axis, wherein about ½-⅓ of the embryo axis remained attached to the nodal end of the cotyledon.

Inoculation. The split soybean seeds comprising a partial portion of the embryonic axis were then immersed for about 30 minutes in a solution of *Agrobacterium tumefaciens* (e.g., strain EHA 101 or EHA 105) containing binary plasmid comprising DIG protein. The *Agrobacterium tumefaciens* solution was diluted to a final concentration of $\lambda$=0.6 $OD_{650}$ before immersing the cotyledons comprising the embryo axis.

Co-cultivation. Following inoculation, the split soybean seed was allowed to co-cultivate with the *Agrobacterium tumefaciens* strain for 5 days on co-cultivation medium (Wang, Kan. *Agrobacterium Protocols*. 2. 1. New Jersey: Humana Press, 2006. Print.) in a Petri dish covered with a piece of filter paper.

Shoot induction. After 5 days of co-cultivation, the split soybean seeds were washed in liquid Shoot Induction (SI) media consisting of B5 salts, B5 vitamins, 28 mg/L Ferrous, 38 mg/L $Na_2$EDTA, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds were then cultured on Shoot Induction I (SI I) medium consisting of B5 salts, B5 vitamins, 7 g/L Noble agar, 28 mg/L Ferrous, 38 mg/L $Na_2$EDTA, 30 g/L sucrose, 0.6 g/L MES, 1.11 mg/L BAP, 50 mg/L TIMENTIN™, 200 mg/L cefotaxime, 50 mg/L vancomycin (pH 5.7), with the flat side of the cotyledon facing up and the nodal end of the cotyledon imbedded into the medium. After 2 weeks of culture, the explants from the transformed split soybean seed were transferred to the Shoot Induction II (SI II) medium containing SII medium supplemented with 6 mg/L glufosinate (LIBERTY®).

Shoot elongation. After 2 weeks of culture on SI II medium, the cotyledons were removed from the explants and a flush shoot pad containing the embryonic axis were excised by making a cut at the base of the cotyledon. The isolated shoot pad from the cotyledon was transferred to Shoot Elongation (SE) medium. The SE medium consisted of MS salts, 28 mg/L Ferrous, 38 mg/L $Na_2$EDTA, 30 g/L sucrose and 0.6 g/L MES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, 7 g/L Noble agar, (pH 5.7). The cultures were transferred to fresh SE medium every 2 weeks. The cultures were grown in a CONVIRON™ growth chamber at 24° C. with an 18 h photoperiod at a light intensity of 80-90 μmol/$m^2$sec.

Rooting. Elongated shoots which developed from the cotyledon shoot pad were isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots were transferred to rooting medium (MS salts, B5 vitamins, 28 mg/L Ferrous, 38 mg/L $Na_2EDTA$, 20 g/L sucrose and 0.59 g/L MES, 50 mg/L asparagine, 100 mg/L L-pyroglutamic acid 7 g/L Noble agar, pH 5.6) in phyta trays.

Cultivation. Following culture in a CONVIRON™ growth chamber at 24° C., 18 h photoperiod, for 1-2 weeks, the shoots which had developed roots were transferred to a soil mix in a covered sundae cup and placed in a CONVIRON™ growth chamber (models CMP4030 and CMP3244, Controlled Environments Limited, Winnipeg, Manitoba, Canada) under long day conditions (16 hours light/8 hours dark) at a light intensity of 120-150 μmol/m$^2$sec under constant temperature (22° C.) and humidity (40-50%) for acclimatization of plantlets. The rooted plantlets were acclimated in sundae cups for several weeks before they were transferred to the greenhouse for further acclimatization and establishment of robust transgenic soybean plants.

Development and morphological characteristics of transgenic lines were compared with nontransformed plants. Plant root, shoot, foliage and reproduction characteristics were compared. There were no observable difference in root length and growth patterns of transgenic and nontransformed plants. Plant shoot characteristics such as height, leaf numbers and sizes, time of flowering, floral size and appearance were similar. In general, there were no observable morphological differences between transgenic lines and those without expression of DIG proteins when cultured in vitro and in soil in the glasshouse.

EXAMPLE 11

Transformation of Additional Crop Species

Cotton is transformed with B.t. proteins (with or without a chloroplast transit peptide) to provide control of lepidopteran insects by utilizing a method known to those of skill in the art, for example, substantially the same techniques previously described in EXAMPLE 9 of U.S. Pat. No. 7,838,733, or Example 12 of PCT International Patent Publication No. WO 2007/053482.

It should be understood that the examples and embodiments described herein are for illustrative purposes only and that various modifications or changes in light thereof will be suggested to persons skilled in the art and are to be included within the spirit and purview of this application and the scope of the appended claims. With the teachings provided herein, one skilled in the art could readily produce and use the various toxins and polynucleotide sequences described herein.

We claim:

1. A modified Cry1Ca toxin comprising residues 2 to 68 of SEQ ID NO:2 wherein amino acid residue 54 of SEQ ID NO:2 is Ala, amino acid residue 57 of SEQ ID NO:2 is selected from the group consisting of Leu and Met, and amino acid residue 68 of SEQ ID NO:2 is selected from the group consisting of Val, Phe, and Ile.

2. A modified Cry1Ca toxin comprising residues 2 to 628 of SEQ ID NO:10 wherein amino acid residue 54 Ala, amino acid residue 57 is selected from the group consisting of Leu and Met, amino acid residue 68 is selected from the group consisting of Val, Phe, and Ile, amino acid residue 73 is selected from the group consisting of Trp, Ala and Met, amino acid residue 596 is selected from the group consisting of Phe, Met and Ala, and amino acid residue 620 is selected from the group consisting of Leu and Phe.

3. The modified Cry1Ca toxin of claim 1 further comprising a carboxy terminal extension consisting of amino acid residues 629 to 1164 of SEQ ID NO:36.

4. The modified Cry1Ca toxin of claim 2 further comprising a carboxy terminal extension consisting of amino acid residues 629 to 1164 of SEQ ID NO:36.

5. The modified Cry1Ca toxin of claim 1 further comprising an amino terminal extension consisting of amino acid residues 1 to 74 of SEQ ID NO:40.

6. The modified Cry1Ca toxin of claim 2 further comprising an amino terminal extension consisting of amino acid residues 1 to 74 of SEQ ID NO:40.

7. The modified Cry1Ca toxin of claim 3 further comprising an amino terminal extension consisting of amino acid residues 1 to 74 of SEQ ID NO:40.

8. The modified Cry1Ca toxin of claim 4 further comprising an amino terminal extension consisting of amino acid residues 1 to 74 of SEQ ID NO:40.

9. A modified Cry1Ca toxin selected from the group consisting of SEQ ID NO:4, SEQ ID NO:6, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:38, and SEQ ID NO:40.

10. A nucleic acid molecule comprising a nucleic acid sequence encoding the modified Cry1Ca toxin of claim 1.

11. A nucleic acid molecule comprising a nucleic acid sequence encoding the modified Cry1Ca toxin of claim 2.

12. A nucleic acid molecule comprising a nucleic acid sequence encoding the modified Cry1Ca toxin of claim 3.

13. A nucleic acid molecule comprising a nucleic acid sequence encoding the modified Cry1Ca toxin of claim 4.

14. A nucleic acid molecule comprising a nucleic acid sequence encoding the modified Cry1Ca toxin of claim 5.

15. A nucleic acid molecule comprising a nucleic acid sequence encoding the modified Cry1Ca toxin of claim 6.

16. A nucleic acid molecule comprising a nucleic acid sequence encoding the modified Cry1Ca toxin of claim 7.

17. A nucleic acid molecule comprising a nucleic acid sequence encoding the modified Cry1Ca toxin of claim 8.

18. A nucleic acid molecule comprising a nucleic acid sequence chosen from the group consisting of SEQ ID NO:3, SEQ ID NO:5, SEQ ID NO:7, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:37, and SEQ ID NO:39.

19. A transgenic plant, plant part, or seed that produces the modified Cry1Ca toxin of claim 1.

20. The transgenic plant, plant part, or seed of claim 19 selected from the group consisting of maize, sunflower, soybean, cotton, canola, rice, sorghum, wheat, barley, vegetables, ornamentals, peppers, sugar beets, fruit, and turf grass.

21. The transgenic plant, plant part, or seed of claim 19 selected from the group consisting of maize, soybean and cotton.

22. The transgenic plant, plant part, or seed of claim 19 that is maize.

23. The transgenic plant, plant part, or seed of claim 19 that is soybean.

24. The transgenic plant, plant part, or seed of claim 19 that is cotton.

25. A method of controlling plant insect pests comprising growing a transgenic plant that expresses the modified Cry1Ca toxin of claim 1 or claim 2 and allowing susceptible pests to feed on said transgenic plant.

26. A method of controlling plant insect pests that have developed resistance to other Cry toxins comprising growing a transgenic plant that expresses the modified Cry1Ca toxin of claim 1 or claim 2 and allowing susceptible pests to feed on said transgenic plant.

* * * * *

SEQUENCE LISTING

```
<160> NUMBER OF SEQ ID NOS: 40

<210> SEQ ID NO 1
<211> LENGTH: 1878
<212> TYPE: DNA
<213> ORGANISM: Artificial Sequence
<220> FEATURE:
<223> OTHER INFORMATION: synthesized coding region

<400> SEQUENCE: 1

atggataaca accccaacat taacgagtgc atcccgtaca actgcctctc gaatccagaa      60

gaagtgctct tggatggcga gaggatttcg actggcaaca gctccatcga catttccctc     120

tccttggttc agttccttgt gtctaacttc gtccctggcg gtggcttcct tgttggcctt     180

atcgacttcg tctggggaat tgtccagtgg gatgcgtttc tggtgcagat agagcagctg     240

atcaacgaga ggatcgctga gttcgcgaga aatgctgcaa tcgccaacct tgaagggctt     300

ggcaacaact tcaacatcta cgtggaggcg ttcaaggagt gggaagagga ccctaagaat     360

ccagcgacca gaacgagggt tatagatcgg ttccgcatcc tcgatggcct tttggagagg     420

gacatcccga gcttccgcat ttcgggattt gaggttcctc tgctctcagt ctacgctcaa     480

gctgctaatc tgcatctggc catcttgagg gattcagtca tctttggcga acgctggggt     540

cttacgacta tcaacgtgaa cgagaactac aatcggttga ttcggcacat agacgagtat     600

gccgaccact gtgctaacac ctacaatagg ggtctgaaca atctgccaaa gtcaacgtat     660

caagactgga taacctacaa taggctcaga cgggacctca ctctcaccgt gctggacata     720

gctgccttct ttccgaacta cgacaaccgg agatatccta ttcaacccgt tggtcagctc     780

actcgcgagg tctacaccga tcccctcatc aacttcaatc cccagctgca atcggtcgca     840

cagctgccca ccttcaatgt gatggaaaac tcagcgatcc ggaatcccca tctgtttgac     900

atacttaaca acctcactat cttcaccgat tggttttcag ttggacgcaa cttctactgg     960

ggagggcaca gagtgatttc aagcctcatt ggaggaggga acattacatc gcctatctat    1020

ggaagggagg ccaaccaaga gccaccaagg tctttcacct tcaacggtcc ggtgttcaga    1080
```

```
acacttagca atcccacatt gcgcttgctg caacagccgt ggccagcacc accattcaat   1140

ctgaggggag tggagggtgt ggagttctcg acgcctacaa actcctttac gtacagaggc   1200

agagggacag tggactcact gacagaactc ccacctgagg acaactctgt tcctccgagg   1260

gagggctact cgcaccggct ttgccatgcc accttcgtcc agaggtctgg cacgcctttt   1320

ctgaccactg ggttgtctt tagctggact caccgctcag cgacgctgac caacacaatc   1380

gacccagaga ggatcaatca gatccctctg gtgaagggct ttcgcgtttg gggtggcaca   1440

agcgtgatca ccggacctgg tttcactggt ggggatatcc tcagacgcaa tacgtttggc   1500

gatttcgtga gccttcaagt caacatcaat tccccaatca cccagagata tcggctccgc   1560

ttcagatacg cctcatccag agacgcaagg gtcatcgtcc ttactggagc agccagcacc   1620

ggagtcggag gccaagttag cgtcaacatg ccgttgcaga aaacgatgga aatcggtgaa   1680

aacctcacca gcagaacctt tcgctataca gatttcagca accctttctc cttcagagcc   1740

aatccggaca taatcggcat atccgagcag cccttgttcg gtgctgggtc catctcttct   1800

ggcgagctgt acatcgacaa gattgagatc attctcgcag atgcgactct ggaggctgaa   1860

tcggatcttg aaaggtga                                                 1878
```

```
<210> SEQ ID NO 2
<211> LENGTH: 625
<212> TYPE: PRT
<213> ORGANISM: Artificial Sequence
<220> FEATURE:
<223> OTHER INFORMATION: translated from synthesized coding region

<400> SEQUENCE: 2

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gln Trp Asp Ala Phe Leu Val Gln Ile Glu Gln Leu
65                  70                  75                  80

Ile Asn Glu Arg Ile Ala Glu Phe Ala Arg Asn Ala Ala Ile Ala Asn
                85                  90                  95

Leu Glu Gly Leu Gly Asn Asn Phe Asn Ile Tyr Val Glu Ala Phe Lys
            100                 105                 110

Glu Trp Glu Glu Asp Pro Lys Asn Pro Ala Thr Arg Thr Arg Val Ile
        115                 120                 125

Asp Arg Phe Arg Ile Leu Asp Gly Leu Leu Glu Arg Asp Ile Pro Ser
    130                 135                 140

Phe Arg Ile Ser Gly Phe Glu Val Pro Leu Leu Ser Val Tyr Ala Gln
145                 150                 155                 160

Ala Ala Asn Leu His Leu Ala Ile Leu Arg Asp Ser Val Ile Phe Gly
                165                 170                 175

Glu Arg Trp Gly Leu Thr Thr Ile Asn Val Asn Glu Asn Tyr Asn Arg
            180                 185                 190

Leu Ile Arg His Ile Asp Glu Tyr Ala Asp His Cys Ala Asn Thr Tyr
        195                 200                 205

Asn Arg Gly Leu Asn Asn Leu Pro Lys Ser Thr Tyr Gln Asp Trp Ile
```

```
    210                 215                 220

Thr Tyr Asn Arg Leu Arg Arg Asp Leu Thr Leu Thr Val Leu Asp Ile
225                 230                 235                 240

Ala Ala Phe Phe Pro Asn Tyr Asp Asn Arg Arg Tyr Pro Ile Gln Pro
                245                 250                 255

Val Gly Gln Leu Thr Arg Glu Val Tyr Thr Asp Pro Leu Ile Asn Phe
            260                 265                 270

Asn Pro Gln Leu Gln Ser Val Ala Gln Leu Pro Thr Phe Asn Val Met
        275                 280                 285

Glu Asn Ser Ala Ile Arg Asn Pro His Leu Phe Asp Ile Leu Asn Asn
    290                 295                 300

Leu Thr Ile Phe Thr Asp Trp Phe Ser Val Gly Arg Asn Phe Tyr Trp
305                 310                 315                 320

Gly Gly His Arg Val Ile Ser Ser Leu Ile Gly Gly Gly Asn Ile Thr
                325                 330                 335

Ser Pro Ile Tyr Gly Arg Glu Ala Asn Gln Glu Pro Pro Arg Ser Phe
            340                 345                 350

Thr Phe Asn Gly Pro Val Phe Arg Thr Leu Ser Asn Pro Thr Leu Arg
        355                 360                 365

Leu Leu Gln Gln Pro Trp Pro Ala Pro Pro Phe Asn Leu Arg Gly Val
    370                 375                 380

Glu Gly Val Glu Phe Ser Thr Pro Thr Asn Ser Phe Thr Tyr Arg Gly
385                 390                 395                 400

Arg Gly Thr Val Asp Ser Leu Thr Glu Leu Pro Pro Glu Asp Asn Ser
                405                 410                 415

Val Pro Pro Arg Glu Gly Tyr Ser His Arg Leu Cys His Ala Thr Phe
            420                 425                 430

Val Gln Arg Ser Gly Thr Pro Phe Leu Thr Thr Gly Val Val Phe Ser
        435                 440                 445

Trp Thr His Arg Ser Ala Thr Leu Thr Asn Thr Ile Asp Pro Glu Arg
    450                 455                 460

Ile Asn Gln Ile Pro Leu Val Lys Gly Phe Arg Val Trp Gly Gly Thr
465                 470                 475                 480

Ser Val Ile Thr Gly Pro Gly Phe Thr Gly Gly Asp Ile Leu Arg Arg
                485                 490                 495

Asn Thr Phe Gly Asp Phe Val Ser Leu Gln Val Asn Ile Asn Ser Pro
            500                 505                 510

Ile Thr Gln Arg Tyr Arg Leu Arg Phe Arg Tyr Ala Ser Ser Arg Asp
        515                 520                 525

Ala Arg Val Ile Val Leu Thr Gly Ala Ala Ser Thr Gly Val Gly Gly
    530                 535                 540

Gln Val Ser Val Asn Met Pro Leu Gln Lys Thr Met Glu Ile Gly Glu
545                 550                 555                 560

Asn Leu Thr Ser Arg Thr Phe Arg Tyr Thr Asp Phe Ser Asn Pro Phe
                565                 570                 575

Ser Phe Arg Ala Asn Pro Asp Ile Ile Gly Ile Ser Glu Gln Pro Leu
            580                 585                 590

Phe Gly Ala Gly Ser Ile Ser Ser Gly Glu Leu Tyr Ile Asp Lys Ile
        595                 600                 605

Glu Ile Ile Leu Ala Asp Ala Thr Leu Glu Ala Glu Ser Asp Leu Glu
    610                 615                 620

Arg
625
```

<210> SEQ ID NO 3
<211> LENGTH: 1878
<212> TYPE: DNA
<213> ORGANISM: Artificial Sequence
<220> FEATURE:
<223> OTHER INFORMATION: synthesized coding region

<400> SEQUENCE: 3

```
atggataaca accccaacat taacgagtgc atcccgtaca actgcctctc gaatccagaa     60
gaagtgctct tggatggcga gaggatttcg actggcaaca gctccatcga catttccctc    120
tccttggttc agttccttgt gtctaacttc gtccctggcg ccggcttcct tgttggcctt    180
atcgacttcg tctggggaat tgtccagtgg gatgcgtttc tggtgcagat agagcagctg    240
atcaacgaga ggatcgctga gttcgcgaga aatgctgcaa tcgccaacct tgaagggctt    300
ggcaacaact tcaacatcta cgtggaggcg ttcaaggagt gggaagagga ccctaagaat    360
ccagcgacca gaacgagggt tatagatcgg ttccgcatcc tcgatggcct tttggagagg    420
gacatcccga gcttccgcat ttcgggattt gaggttcctc tgctctcagt ctacgctcaa    480
gctgctaatc tgcatctggc catcttgagg gattcagtca tctttggcga acgctggggt    540
cttacgacta tcaacgtgaa cgagaactac aatcggttga ttcggcacat agacgagtat    600
gccgaccact gtgctaacac ctacaatagg ggtctgaaca atctgccaaa gtcaacgtat    660
caagactgga taacctacaa taggctcaga cgggacctca ctctcaccgt gctggacata    720
gctgccttct ttccgaacta cgacaaccgg agatatccta ttcaacccgt tggtcagctc    780
actcgcgagg tctacaccga tcccctcatc aacttcaatc cccagctgca atcggtcgca    840
cagctgccca ccttcaatgt gatggaaaac tcagcgatcc ggaatcccca tctgtttgac    900
atacttaaca acctcactat cttcaccgat tggttttcag ttggacgcaa cttctactgg    960
ggagggcaca gagtgatttc aagcctcatt ggaggaggga acattacatc gcctatctat   1020
ggaagggagg ccaaccaaga gccaccaagg tctttcacct tcaacggtcc ggtgttcaga   1080
acacttagca atcccacatt gcgcttgctg caacagccgt ggccagcacc accattcaat   1140
ctgaggggag tggagggtgt ggagttctcg acgcctacaa actcctttac gtacagaggc   1200
agagggacag tggactcact gacagaactc ccacctgagg acaactctgt tcctccgagg   1260
gagggctact cgcaccggct ttgccatgcc accttcgtcc agaggtctgg cacgcctttt   1320
ctgaccactg ggttgtcttt tagctggact caccgctcag cgacgctgac caacacaatc   1380
gacccagaga ggatcaatca gatccctctg gtgaagggct ttcgcgtttg ggggtggcaca  1440
agcgtgatca ccggacctgg tttcactggt ggggatatcc tcagacgcaa tacgtttggc   1500
gatttcgtga gccttcaagt caacatcaat tccccaatca cccagagata tcggctccgc   1560
ttcagatacg cctcatccag agacgcaagg gtcatcgtcc ttactggagc agccagcacc   1620
ggagtcggag gccaagttag cgtcaacatg ccgttgcaga aaacgatgga aatcggtgaa   1680
aacctcacca gcagaacctt tcgctataca gatttcagca accctttctc cttcagagcc   1740
aatccggaca taatcggcat atccgagcag ccccttgttcg gtgctgggtc catctcttct  1800
ggcgagctgt acatcgacaa gattgagatc attctcgcag atgcgactct ggaggctgaa   1860
tcggatcttg aaaggtga                                                 1878
```

<210> SEQ ID NO 4
<211> LENGTH: 625
<212> TYPE: PRT

<213> ORGANISM: Artificial Sequence
<220> FEATURE:
<223> OTHER INFORMATION: translated from synthesized coding region

<400> SEQUENCE: 4

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Ala Gly Phe Leu Val Gly Leu Ile Asp Phe Val
    50                  55                  60

Trp Gly Ile Val Gln Trp Asp Ala Phe Leu Val Gln Ile Glu Gln Leu
65                  70                  75                  80

Ile Asn Glu Arg Ile Ala Glu Phe Ala Arg Asn Ala Ala Ile Ala Asn
                85                  90                  95

Leu Glu Gly Leu Gly Asn Asn Phe Asn Ile Tyr Val Glu Ala Phe Lys
            100                 105                 110

Glu Trp Glu Glu Asp Pro Lys Asn Pro Ala Thr Arg Thr Arg Val Ile
        115                 120                 125

Asp Arg Phe Arg Ile Leu Asp Gly Leu Leu Glu Arg Asp Ile Pro Ser
    130                 135                 140

Phe Arg Ile Ser Gly Phe Glu Val Pro Leu Leu Ser Val Tyr Ala Gln
145                 150                 155                 160

Ala Ala Asn Leu His Leu Ala Ile Leu Arg Asp Ser Val Ile Phe Gly
                165                 170                 175

Glu Arg Trp Gly Leu Thr Thr Ile Asn Val Asn Glu Asn Tyr Asn Arg
            180                 185                 190

Leu Ile Arg His Ile Asp Glu Tyr Ala Asp His Cys Ala Asn Thr Tyr
        195                 200                 205

Asn Arg Gly Leu Asn Asn Leu Pro Lys Ser Thr Tyr Gln Asp Trp Ile
    210                 215                 220

Thr Tyr Asn Arg Leu Arg Arg Asp Leu Thr Leu Thr Val Leu Asp Ile
225                 230                 235                 240

Ala Ala Phe Phe Pro Asn Tyr Asp Asn Arg Arg Tyr Pro Ile Gln Pro
                245                 250                 255

Val Gly Gln Leu Thr Arg Glu Val Tyr Thr Asp Pro Leu Ile Asn Phe
            260                 265                 270

Asn Pro Gln Leu Gln Ser Val Ala Gln Leu Pro Thr Phe Asn Val Met
        275                 280                 285

Glu Asn Ser Ala Ile Arg Asn Pro His Leu Phe Asp Ile Leu Asn Asn
    290                 295                 300

Leu Thr Ile Phe Thr Asp Trp Phe Ser Val Gly Arg Asn Phe Tyr Trp
305                 310                 315                 320

Gly Gly His Arg Val Ile Ser Ser Leu Ile Gly Gly Gly Asn Ile Thr
                325                 330                 335

Ser Pro Ile Tyr Gly Arg Glu Ala Asn Gln Glu Pro Pro Arg Ser Phe
            340                 345                 350

Thr Phe Asn Gly Pro Val Phe Arg Thr Leu Ser Asn Pro Thr Leu Arg
        355                 360                 365

Leu Leu Gln Gln Pro Trp Pro Ala Pro Pro Phe Asn Leu Arg Gly Val
    370                 375                 380

Glu Gly Val Glu Phe Ser Thr Pro Thr Asn Ser Phe Thr Tyr Arg Gly
```

385 390 395 400

Arg Gly Thr Val Asp Ser Leu Thr Glu Leu Pro Pro Glu Asp Asn Ser
405 410 415

Val Pro Pro Arg Glu Gly Tyr Ser His Arg Leu Cys His Ala Thr Phe
420 425 430

Val Gln Arg Ser Gly Thr Pro Phe Leu Thr Thr Gly Val Val Phe Ser
435 440 445

Trp Thr His Arg Ser Ala Thr Leu Thr Asn Thr Ile Asp Pro Glu Arg
450 455 460

Ile Asn Gln Ile Pro Leu Val Lys Gly Phe Arg Val Trp Gly Gly Thr
465 470 475 480

Ser Val Ile Thr Gly Pro Gly Phe Thr Gly Gly Asp Ile Leu Arg Arg
485 490 495

Asn Thr Phe Gly Asp Phe Val Ser Leu Gln Val Asn Ile Asn Ser Pro
500 505 510

Ile Thr Gln Arg Tyr Arg Leu Arg Phe Arg Tyr Ala Ser Ser Arg Asp
515 520 525

Ala Arg Val Ile Val Leu Thr Gly Ala Ala Ser Thr Gly Val Gly Gly
530 535 540

Gln Val Ser Val Asn Met Pro Leu Gln Lys Thr Met Glu Ile Gly Glu
545 550 555 560

Asn Leu Thr Ser Arg Thr Phe Arg Tyr Thr Asp Phe Ser Asn Pro Phe
565 570 575

Ser Phe Arg Ala Asn Pro Asp Ile Ile Gly Ile Ser Glu Gln Pro Leu
580 585 590

Phe Gly Ala Gly Ser Ile Ser Ser Gly Glu Leu Tyr Ile Asp Lys Ile
595 600 605

Glu Ile Ile Leu Ala Asp Ala Thr Leu Glu Ala Glu Ser Asp Leu Glu
610 615 620

Arg
625

<210> SEQ ID NO 5
<211> LENGTH: 1878
<212> TYPE: DNA
<213> ORGANISM: Artificial Sequence
<220> FEATURE:
<223> OTHER INFORMATION: synthesized coding region

<400> SEQUENCE: 5
atggataaca accccaacat taacgagtgc atcccgtaca actgcctctc gaatccagaa 60
gaagtgctct tggatggcga gaggatttcg actggcaaca gctccatcga catttccctc 120
tccttggttc agttccttgt gtctaacttc gtccctggcg gtggcttcgc cgttggcctt 180
atcgacttcg tctggggaat tgtccagtgg gatgcgtttc tggtgcagat agagcagctg 240
atcaacgaga ggatcgctga gttcgcgaga aatgctgcaa tcgccaacct tgaagggctt 300
ggcaacaact tcaacatcta cgtggaggcg ttcaaggagt gggaagagga ccctaagaat 360
ccagcgacca gaacgagggt tatagatcgg ttccgcatcc tcgatggcct tttggagagg 420
gacatcccga gcttccgcat ttcgggattt gaggttcctc tgctctcagt ctacgctcaa 480
gctgctaatc tgcatctggc catcttgagg gattcagtca tctttggcga acgctggggt 540
cttacgacta tcaacgtgaa cgagaactac aatcggttga ttcggcacat agacgagtat 600
gccgaccact gtgctaacac ctacaatagg ggtctgaaca atctgccaaa gtcaacgtat 660

```
caagactgga taacctacaa taggctcaga cgggacctca ctctcaccgt gctggacata    720
gctgccttct ttccgaacta cgacaaccgg agatatccta ttcaacccgt tggtcagctc    780
actcgcgagg tctacaccga tcccctcatc aacttcaatc cccagctgca atcggtcgca    840
cagctgccca ccttcaatgt gatggaaaac tcagcgatcc ggaatcccca tctgtttgac    900
atacttaaca acctcactat cttcaccgat tggttttcag ttggacgcaa cttctactgg    960
ggagggcaca gagtgatttc aagcctcatt ggaggaggga acattacatc gcctatctat   1020
ggaagggagg ccaaccaaga gccaccaagg tctttcacct tcaacggtcc ggtgttcaga   1080
acacttagca atcccacatt gcgcttgctg caacagccgt ggccagcacc accattcaat   1140
ctgaggggag tggagggtgt ggagttctcg acgcctacaa actcctttac gtacagaggc   1200
agagggacag tggactcact gacagaactc ccacctgagg acaactctgt tcctccgagg   1260
gagggctact cgcaccggct ttgccatgcc accttcgtcc agaggtctgg cacgcctttt   1320
ctgaccactg ggttgtcttt tagctggact caccgctcag cgacgctgac caacacaatc   1380
gacccagaga ggatcaatca gatccctctg gtgaagggct ttcgcgtttg ggtggcaca    1440
agcgtgatca ccggacctgg tttcactggt ggggatatcc tcagacgcaa tacgtttggc   1500
gatttcgtga gccttcaagt caacatcaat tccccaatca cccagagata tcggctccgc   1560
ttcagatacg cctcatccag agacgcaagg gtcatcgtcc ttactggagc agccagcacc   1620
ggagtcggag gccaagttag cgtcaacatg ccgttgcaga aaacgatgga aatcggtgaa   1680
aacctcacca gcagaacctt tcgctataca gatttcagca accctttctc cttcagagcc   1740
aatccggaca taatcggcat atccgagcag cccttgttcg gtgctgggtc catctcttct   1800
ggcgagctgt acatcgacaa gattgagatc attctcgcag atgcgactct ggaggctgaa   1860
tcggatcttg aaaggtga                                                 1878
```

<210> SEQ ID NO 6
<211> LENGTH: 625
<212> TYPE: PRT
<213> ORGANISM: Artificial Sequence
<220> FEATURE:
<223> OTHER INFORMATION: translated from synthesized coding region

<400> SEQUENCE: 6

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Ala Val Gly Leu Ile Asp Phe Val
    50                  55                  60

Trp Gly Ile Val Gln Trp Asp Ala Phe Leu Val Gln Ile Glu Gln Leu
65                  70                  75                  80

Ile Asn Glu Arg Ile Ala Glu Phe Ala Arg Asn Ala Ala Ile Ala Asn
                85                  90                  95

Leu Glu Gly Leu Gly Asn Asn Phe Asn Ile Tyr Val Glu Ala Phe Lys
            100                 105                 110

Glu Trp Glu Glu Asp Pro Lys Asn Pro Ala Thr Arg Thr Arg Val Ile
        115                 120                 125

Asp Arg Phe Arg Ile Leu Asp Gly Leu Leu Glu Arg Asp Ile Pro Ser
    130                 135                 140
```

-continued

```
Phe Arg Ile Ser Gly Phe Glu Val Pro Leu Leu Ser Val Tyr Ala Gln
145                 150                 155                 160

Ala Ala Asn Leu His Leu Ala Ile Leu Arg Asp Ser Val Ile Phe Gly
                165                 170                 175

Glu Arg Trp Gly Leu Thr Thr Ile Asn Val Asn Glu Asn Tyr Asn Arg
            180                 185                 190

Leu Ile Arg His Ile Asp Glu Tyr Ala Asp His Cys Ala Asn Thr Tyr
        195                 200                 205

Asn Arg Gly Leu Asn Asn Leu Pro Lys Ser Thr Tyr Gln Asp Trp Ile
    210                 215                 220

Thr Tyr Asn Arg Leu Arg Arg Asp Leu Thr Leu Thr Val Leu Asp Ile
225                 230                 235                 240

Ala Ala Phe Phe Pro Asn Tyr Asp Asn Arg Arg Tyr Pro Ile Gln Pro
                245                 250                 255

Val Gly Gln Leu Thr Arg Glu Val Tyr Thr Asp Pro Leu Ile Asn Phe
            260                 265                 270

Asn Pro Gln Leu Gln Ser Val Ala Gln Leu Pro Thr Phe Asn Val Met
        275                 280                 285

Glu Asn Ser Ala Ile Arg Asn Pro His Leu Phe Asp Ile Leu Asn Asn
    290                 295                 300

Leu Thr Ile Phe Thr Asp Trp Phe Ser Val Gly Arg Asn Phe Tyr Trp
305                 310                 315                 320

Gly Gly His Arg Val Ile Ser Ser Leu Ile Gly Gly Gly Asn Ile Thr
                325                 330                 335

Ser Pro Ile Tyr Gly Arg Glu Ala Asn Gln Glu Pro Pro Arg Ser Phe
            340                 345                 350

Thr Phe Asn Gly Pro Val Phe Arg Thr Leu Ser Asn Pro Thr Leu Arg
        355                 360                 365

Leu Leu Gln Gln Pro Trp Pro Ala Pro Pro Phe Asn Leu Arg Gly Val
    370                 375                 380

Glu Gly Val Glu Phe Ser Thr Pro Thr Asn Ser Phe Thr Tyr Arg Gly
385                 390                 395                 400

Arg Gly Thr Val Asp Ser Leu Thr Glu Leu Pro Pro Glu Asp Asn Ser
                405                 410                 415

Val Pro Pro Arg Glu Gly Tyr Ser His Arg Leu Cys His Ala Thr Phe
            420                 425                 430

Val Gln Arg Ser Gly Thr Pro Phe Leu Thr Thr Gly Val Val Phe Ser
        435                 440                 445

Trp Thr His Arg Ser Ala Thr Leu Thr Asn Thr Ile Asp Pro Glu Arg
    450                 455                 460

Ile Asn Gln Ile Pro Leu Val Lys Gly Phe Arg Val Trp Gly Gly Thr
465                 470                 475                 480

Ser Val Ile Thr Gly Pro Gly Phe Thr Gly Gly Asp Ile Leu Arg Arg
                485                 490                 495

Asn Thr Phe Gly Asp Phe Val Ser Leu Gln Val Asn Ile Asn Ser Pro
            500                 505                 510

Ile Thr Gln Arg Tyr Arg Leu Arg Phe Arg Tyr Ala Ser Ser Arg Asp
        515                 520                 525

Ala Arg Val Ile Val Leu Thr Gly Ala Ala Ser Thr Gly Val Gly Gly
    530                 535                 540

Gln Val Ser Val Asn Met Pro Leu Gln Lys Thr Met Glu Ile Gly Glu
545                 550                 555                 560

Asn Leu Thr Ser Arg Thr Phe Arg Tyr Thr Asp Phe Ser Asn Pro Phe
```

-continued

```
                565                 570                 575

Ser Phe Arg Ala Asn Pro Asp Ile Ile Gly Ile Ser Glu Gln Pro Leu
            580                 585                 590

Phe Gly Ala Gly Ser Ile Ser Ser Gly Glu Leu Tyr Ile Asp Lys Ile
        595                 600                 605

Glu Ile Ile Leu Ala Asp Ala Thr Leu Glu Ala Glu Ser Asp Leu Glu
    610                 615                 620

Arg
625


<210> SEQ ID NO 7
<211> LENGTH: 1878
<212> TYPE: DNA
<213> ORGANISM: Artificial Sequence
<220> FEATURE:
<223> OTHER INFORMATION: synthesized coding region

<400> SEQUENCE: 7

atggataaca accccaacat taacgagtgc atcccgtaca actgcctctc gaatccagaa     60

gaagtgctct tggatggcga gaggatttcg actggcaaca gctccatcga catttccctc    120

tccttggttc agttccttgt gtctaacttc gtccctggcg gtggcttcat ggttggcctt    180

atcgacttcg tctggggaat tgtccagtgg gatgcgtttc tggtgcagat agagcagctg    240

atcaacgaga ggatcgctga gttcgcgaga aatgctgcaa tcgccaacct tgaagggctt    300

ggcaacaact tcaacatcta cgtggaggcg ttcaaggagt gggaagagga ccctaagaat    360

ccagcgacca gaacgagggt tatagatcgg ttccgcatcc tcgatggcct tttggagagg    420

gacatcccga gcttccgcat ttcgggattt gaggttcctc tgctctcagt ctacgctcaa    480

gctgctaatc tgcatctggc catcttgagg gattcagtca tctttggcga acgctggggt    540

cttacgacta tcaacgtgaa cgagaactac aatcggttga ttcggcacat agacgagtat    600

gccgaccact gtgctaacac ctacaatagg ggtctgaaca atctgccaaa gtcaacgtat    660

caagactgga taacctacaa taggctcaga cgggacctca ctctcaccgt gctggacata    720

gctgccttct ttccgaacta cgacaaccgg agatatccta ttcaacccgt tggtcagctc    780

actcgcgagg tctacaccga tcccctcatc aacttcaatc cccagctgca atcggtcgca    840

cagctgccca ccttcaatgt gatggaaaac tcagcgatcc ggaatcccca tctgtttgac    900

atacttaaca acctcactat cttcaccgat tggttttcag ttggacgcaa cttctactgg    960

ggagggcaca gagtgatttc aagcctcatt ggaggaggga acattacatc gcctatctat   1020

ggaagggagg ccaaccaaga gccaccaagg tctttcacct tcaacggtcc ggtgttcaga   1080

acacttagca atcccacatt gcgcttgctg caacagccgt ggccagcacc accattcaat   1140

ctgaggggag tggagggtgt ggagttctcg acgcctacaa actcctttac gtacagaggc   1200

agagggacag tggactcact gacagaactc ccacctgagg acaactctgt tcctccgagg   1260

gagggctact cgcaccggct ttgccatgcc accttcgtcc agaggtctgg cacgcctttt   1320

ctgaccactg ggttgtcttt tagctggact caccgctcag cgacgctgac caacacaatc   1380

gacccagaga ggatcaatca gatccctctg gtgaagggct ttcgcgtttg ggggtggcaca   1440

agcgtgatca ccggacctgg tttcactggt ggggatatcc tcagacgcaa tacgtttggc   1500

gatttcgtga gccttcaagt caacatcaat tccccaatca cccagagata tcggctccgc   1560

ttcagatacg cctcatccag agacgcaagg gtcatcgtcc ttactggagc agccagcacc   1620

ggagtcggag gccaagttag cgtcaacatg ccgttgcaga aaacgatgga aatcggtgaa   1680
```

```
aacctcacca gcagaacctt tcgctataca gatttcagca accctttctc cttcagagcc   1740

aatccggaca taatcggcat atccgagcag cccttgttcg gtgctgggtc catctcttct   1800

ggcgagctgt acatcgacaa gattgagatc attctcgcag atgcgactct ggaggctgaa   1860

tcggatcttg aaaggtga                                                  1878


<210> SEQ ID NO 8
<211> LENGTH: 625
<212> TYPE: PRT
<213> ORGANISM: Artificial Sequence
<220> FEATURE:
<223> OTHER INFORMATION: translated from synthesized coding region

<400> SEQUENCE: 8

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Met Val Gly Leu Ile Asp Phe Val
    50                  55                  60

Trp Gly Ile Val Gln Trp Asp Ala Phe Leu Val Gln Ile Glu Gln Leu
65                  70                  75                  80

Ile Asn Glu Arg Ile Ala Glu Phe Ala Arg Asn Ala Ala Ile Ala Asn
                85                  90                  95

Leu Glu Gly Leu Gly Asn Asn Phe Asn Ile Tyr Val Glu Ala Phe Lys
            100                 105                 110

Glu Trp Glu Glu Asp Pro Lys Asn Pro Ala Thr Arg Thr Arg Val Ile
        115                 120                 125

Asp Arg Phe Arg Ile Leu Asp Gly Leu Leu Glu Arg Asp Ile Pro Ser
    130                 135                 140

Phe Arg Ile Ser Gly Phe Glu Val Pro Leu Leu Ser Val Tyr Ala Gln
145                 150                 155                 160

Ala Ala Asn Leu His Leu Ala Ile Leu Arg Asp Ser Val Ile Phe Gly
                165                 170                 175

Glu Arg Trp Gly Leu Thr Thr Ile Asn Val Asn Glu Asn Tyr Asn Arg
            180                 185                 190

Leu Ile Arg His Ile Asp Glu Tyr Ala Asp His Cys Ala Asn Thr Tyr
        195                 200                 205

Asn Arg Gly Leu Asn Asn Leu Pro Lys Ser Thr Tyr Gln Asp Trp Ile
    210                 215                 220

Thr Tyr Asn Arg Leu Arg Arg Asp Leu Thr Leu Thr Val Leu Asp Ile
225                 230                 235                 240

Ala Ala Phe Phe Pro Asn Tyr Asp Asn Arg Arg Tyr Pro Ile Gln Pro
                245                 250                 255

Val Gly Gln Leu Thr Arg Glu Val Tyr Thr Asp Pro Leu Ile Asn Phe
            260                 265                 270

Asn Pro Gln Leu Gln Ser Val Ala Gln Leu Pro Thr Phe Asn Val Met
        275                 280                 285

Glu Asn Ser Ala Ile Arg Asn Pro His Leu Phe Asp Ile Leu Asn Asn
    290                 295                 300

Leu Thr Ile Phe Thr Asp Trp Phe Ser Val Gly Arg Asn Phe Tyr Trp
305                 310                 315                 320
```

```
Gly Gly His Arg Val Ile Ser Ser Leu Ile Gly Gly Gly Asn Ile Thr
                325                 330                 335

Ser Pro Ile Tyr Gly Arg Glu Ala Asn Gln Glu Pro Pro Arg Ser Phe
            340                 345                 350

Thr Phe Asn Gly Pro Val Phe Arg Thr Leu Ser Asn Pro Thr Leu Arg
        355                 360                 365

Leu Leu Gln Gln Pro Trp Pro Ala Pro Pro Phe Asn Leu Arg Gly Val
    370                 375                 380

Glu Gly Val Glu Phe Ser Thr Pro Thr Asn Ser Phe Thr Tyr Arg Gly
385                 390                 395                 400

Arg Gly Thr Val Asp Ser Leu Thr Glu Leu Pro Pro Glu Asp Asn Ser
                405                 410                 415

Val Pro Pro Arg Glu Gly Tyr Ser His Arg Leu Cys His Ala Thr Phe
            420                 425                 430

Val Gln Arg Ser Gly Thr Pro Phe Leu Thr Thr Gly Val Val Phe Ser
        435                 440                 445

Trp Thr His Arg Ser Ala Thr Leu Thr Asn Thr Ile Asp Pro Glu Arg
    450                 455                 460

Ile Asn Gln Ile Pro Leu Val Lys Gly Phe Arg Val Trp Gly Gly Thr
465                 470                 475                 480

Ser Val Ile Thr Gly Pro Gly Phe Thr Gly Gly Asp Ile Leu Arg Arg
                485                 490                 495

Asn Thr Phe Gly Asp Phe Val Ser Leu Gln Val Asn Ile Asn Ser Pro
            500                 505                 510

Ile Thr Gln Arg Tyr Arg Leu Arg Phe Arg Tyr Ala Ser Ser Arg Asp
        515                 520                 525

Ala Arg Val Ile Val Leu Thr Gly Ala Ala Ser Thr Gly Val Gly Gly
    530                 535                 540

Gln Val Ser Val Asn Met Pro Leu Gln Lys Thr Met Glu Ile Gly Glu
545                 550                 555                 560

Asn Leu Thr Ser Arg Thr Phe Arg Tyr Thr Asp Phe Ser Asn Pro Phe
                565                 570                 575

Ser Phe Arg Ala Asn Pro Asp Ile Ile Gly Ile Ser Glu Gln Pro Leu
            580                 585                 590

Phe Gly Ala Gly Ser Ile Ser Ser Gly Glu Leu Tyr Ile Asp Lys Ile
        595                 600                 605

Glu Ile Ile Leu Ala Asp Ala Thr Leu Glu Ala Glu Ser Asp Leu Glu
    610                 615                 620

Arg
625


<210> SEQ ID NO 9
<211> LENGTH: 1887
<212> TYPE: DNA
<213> ORGANISM: Bacillus thuringiensis

<400> SEQUENCE: 9

atggataaca accccaacat taacgagtgc atcccgtaca actgcctctc gaatccagaa      60

gaagtgctct tggatggcga gaggatttcg actggcaaca gctccatcga catttccctc     120

tccttggttc agttccttgt gtctaacttc gtccctggcg gtggcttcct tgttggcctt     180

atcgacttcg tctggggaat tgtcggaccc tcccagtggg atgcgtttct ggtgcagata     240

gagcagctga tcaacgagag gatcgctgag ttcgcgagaa atgctgcaat cgccaacctt     300

gaagggcttg gcaacaactt caacatctac gtggaggcgt tcaaggagtg ggaagaggac     360
```

```
cctaagaatc cagcgaccag aacgagggtt atagatcggt tccgcatcct cgatggcctt    420

ttggagaggg acatcccgag cttccgcatt tcgggatttg aggttcctct gctctcagtc    480

tacgctcaag ctgctaatct gcatctggcc atcttgaggg attcagtcat ctttggcgaa    540

cgctggggtc ttacgactat caacgtgaac gagaactaca atcggttgat tcggcacata    600

gacgagtatg ccgaccactg tgctaacacc tacaataggg gtctgaacaa tctgccaaag    660

tcaacgtatc aagactggat aacctacaat aggctcagac gggacctcac tctcaccgtg    720

ctggacatag ctgccttctt tccgaactac gacaaccgga gatatcctat tcaacccgtt    780

ggtcagctca ctcgcgaggt ctacaccgat cccctcatca acttcaatcc ccagctgcaa    840

tcggtcgcac agctgcccac cttcaatgtg atggaaaact cagcgatccg gaatccccat    900

ctgtttgaca tacttaacaa cctcactatc ttcaccgatt ggttttcagt tggacgcaac    960

ttctactggg gagggcacag agtgatttca agcctcattg gaggagggaa cattacatcg   1020

cctatctatg gaagggaggc caaccaagag ccaccaaggt ctttcacctt caacggtccg   1080

gtgttcagaa cacttagcaa tcccacattg cgcttgctgc aacagccgtg gccagcacca   1140

ccattcaatc tgaggggagt ggagggtgtg gagttctcga cgcctacaaa ctcctttacg   1200

tacagaggca gagggacagt ggactcactg acagaactcc cacctgagga caactctgtt   1260

cctccgaggg agggctactc gcaccggctt tgccatgcca ccttcgtcca gaggtctggc   1320

acgccttttc tgaccactgg ggttgtcttt agctggactc accgctcagc gacgctgacc   1380

aacacaatcg acccagagag gatcaatcag atccctctgg tgaagggctt tcgcgtttgg   1440

ggtggcacaa gcgtgatcac cggacctggt ttcactggtg gggatatcct cagacgcaat   1500

acgtttggcg atttcgtgag ccttcaagtc aacatcaatt ccccaatcac ccagagatat   1560

cggctccgct tcagatacgc ctcatccaga gacgcaaggg tcatcgtcct tactggagca   1620

gccagcaccg gagtcggagg ccaagttagc gtcaacatgc cgttgcagaa aacgatggaa   1680

atcggtgaaa acctcaccag cagaaccttt cgctatacag atttcagcaa ccctttctcc   1740

ttcagagcca atccggacat aatcggcata tccgagcagc ccttgttcgg tgctgggtcc   1800

atctcttctg gcgagctgta catcgacaag attgagatca ttctcgcaga tgcgactctg   1860

gaggctgaat cggatcttga aaggtga                                        1887
```

```
<210> SEQ ID NO 10
<211> LENGTH: 628
<212> TYPE: PRT
<213> ORGANISM: Bacillus thuringiensis

<400> SEQUENCE: 10

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95
```

```
Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
```

```
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg
625


<210> SEQ ID NO 11
<211> LENGTH: 1887
<212> TYPE: DNA
<213> ORGANISM: Artificial Sequence
<220> FEATURE:
<223> OTHER INFORMATION: synthesized coding region

<400> SEQUENCE: 11

atggataaca accccaacat taacgagtgc atcccgtaca actgcctctc gaatccagaa      60

gaagtgctct tggatggcga gaggatttcg actggcaaca gctccatcga catttccctc     120

tccttggttc agttccttgt gtctaacttc gtccctggcg ccggcttcct tgttggcctt     180

atcgacttcg tctggggaat tgtcggaccc tcccagtggg atgcgtttct ggtgcagata     240

gagcagctga tcaacgagag gatcgctgag ttcgcgagaa atgctgcaat cgccaacctt     300

gaagggcttg gcaacaactt caacatctac gtggaggcgt tcaaggagtg ggaagaggac     360

cctaagaatc cagcgaccag aacgagggtt atagatcggt tccgcatcct cgatggcctt     420

ttggagaggg acatcccgag cttccgcatt tcgggatttg aggttcctct gctctcagtc     480

tacgctcaag ctgctaatct gcatctggcc atcttgaggg attcagtcat ctttggcgaa     540

cgctggggtc ttacgactat caacgtgaac gagaactaca atcggttgat tcggcacata     600

gacgagtatg ccgaccactg tgctaacacc tacaataggg gtctgaacaa tctgccaaag     660

tcaacgtatc aagactggat aacctacaat aggctcagac gggacctcac tctcaccgtg     720

ctggacatag ctgccttctt tccgaactac gacaaccgga gatatcctat tcaacccgtt     780

ggtcagctca ctcgcgaggt ctacaccgat cccctcatca acttcaatcc ccagctgcaa     840

tcggtcgcac agctgcccac cttcaatgtg atggaaaact cagcgatccg gaatccccat     900

ctgtttgaca tacttaacaa cctcactatc ttcaccgatt ggttttcagt tggacgcaac     960

ttctactggg gagggcacag agtgatttca agcctcattg gaggagggaa cattacatcg    1020

cctatctatg gaagggaggc caaccaagag ccaccaaggt ctttcacctt caacggtccg    1080

gtgttcagaa cacttagcaa tcccacattg cgcttgctgc aacagccgtg gccagcacca    1140

ccattcaatc tgaggggagt ggagggtgtg gagttctcga cgcctacaaa ctcctttacg    1200

tacagaggca gagggacagt ggactcactg acagaactcc cacctgagga caactctgtt    1260

cctccgaggg agggctactc gcaccggctt tgccatgcca ccttcgtcca gaggtctggc    1320

acgccttttc tgaccactgg ggttgtcttt agctggactc accgctcagc gacgctgacc    1380
```

```
aacacaatcg acccagagag gatcaatcag atccctctgg tgaagggctt tcgcgtttgg   1440

ggtggcacaa gcgtgatcac cggacctggt ttcactggtg gggatatcct cagacgcaat   1500

acgtttggcg atttcgtgag ccttcaagtc aacatcaatt ccccaatcac ccagagatat   1560

cggctccgct tcagatacgc ctcatccaga gacgcaaggg tcatcgtcct tactggagca   1620

gccagcaccg gagtcggagg ccaagttagc gtcaacatgc cgttgcagaa aacgatggaa   1680

atcggtgaaa acctcaccag cagaaccttt cgctatacag atttcagcaa ccctttctcc   1740

ttcagagcca atccggacat aatcggcata tccgagcagc ccttgttcgg tgctgggtcc   1800

atctcttctg gcgagctgta catcgacaag attgagatca ttctcgcaga tgcgactctg   1860

gaggctgaat cggatcttga aaggtga                                      1887


<210> SEQ ID NO 12
<211> LENGTH: 628
<212> TYPE: PRT
<213> ORGANISM: Artificial Sequence
<220> FEATURE:
<223> OTHER INFORMATION: translated from synthesized coding region

<400> SEQUENCE: 12

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Ala Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270
```

```
Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg
625
```

<210> SEQ ID NO 13
<211> LENGTH: 1887
<212> TYPE: DNA
<213> ORGANISM: Artificial Sequence
<220> FEATURE:
<223> OTHER INFORMATION: synthesized coding region

<400> SEQUENCE: 13

```
atggataaca accccaacat taacgagtgc atcccgtaca actgcctctc gaatccagaa     60
gaagtgctct tggatggcga gaggatttcg actggcaaca gctccatcga catttccctc    120
tccttggttc agttccttgt gtctaacttc gtccctggcg gtggcttcat ggttggcctt    180
atcgacttcg tctggggaat tgtcggaccc tcccagtggg atgcgtttct ggtgcagata    240
gagcagctga tcaacgagag gatcgctgag ttcgcgagaa atgctgcaat cgccaacctt    300
gaagggcttg gcaacaactt caacatctac gtggaggcgt tcaaggagtg ggaagaggac    360
cctaagaatc cagcgaccag aacgagggtt atagatcggt tccgcatcct cgatggcctt    420
ttggagaggg acatcccgag cttccgcatt tcgggatttg aggttcctct gctctcagtc    480
tacgctcaag ctgctaatct gcatctggcc atcttgaggg attcagtcat ctttggcgaa    540
cgctggggtc ttacgactat caacgtgaac gagaactaca atcggttgat tcggcacata    600
gacgagtatg ccgaccactg tgctaacacc tacaataggg gtctgaacaa tctgccaaag    660
tcaacgtatc aagactggat aacctacaat aggctcagac gggacctcac tctcaccgtg    720
ctggacatag ctgccttctt tccgaactac gacaaccgga gatatcctat tcaacccgtt    780
ggtcagctca ctcgcgaggt ctacaccgat cccctcatca acttcaatcc ccagctgcaa    840
tcggtcgcac agctgcccac cttcaatgtg atggaaaact cagcgatccg gaatccccat    900
ctgtttgaca tacttaacaa cctcactatc ttcaccgatt ggttttcagt tggacgcaac    960
ttctactggg gagggcacag agtgatttca agcctcattg gaggagggaa cattacatcg   1020
cctatctatg gaagggaggc caaccaagag ccaccaaggt ctttcacctt caacggtccg   1080
gtgttcagaa cacttagcaa tcccacattg cgcttgctgc aacagccgtg gccagcacca   1140
ccattcaatc tgaggggagt ggagggtgtg gagttctcga cgcctacaaa ctcctttacg   1200
tacagaggca gagggacagt ggactcactg acagaactcc cacctgagga caactctgtt   1260
cctccgaggg agggctactc gcaccggctt tgccatgcca ccttcgtcca gaggtctggc   1320
acgccttttc tgaccactgg ggttgtcttt agctggactc accgctcagc gacgctgacc   1380
aacacaatcg acccagagag gatcaatcag atccctctgg tgaagggctt tcgcgtttgg   1440
ggtggcacaa gcgtgatcac cggacctggt ttcactggtg gggatatcct cagacgcaat   1500
acgtttggcg atttcgtgag ccttcaagtc aacatcaatt ccccaatcac ccagagatat   1560
cggctccgct tcagatacgc ctcatccaga gacgcaaggg tcatcgtcct tactggagca   1620
gccagcaccg gagtcggagg ccaagttagc gtcaacatgc cgttgcagaa aacgatggaa   1680
atcggtgaaa acctcaccag cagaaccttt cgctatacag atttcagcaa ccctttctcc   1740
ttcagagcca atccggacat aatcggcata tccgagcagc ccttgttcgg tgctgggtcc   1800
atctcttctg gcgagctgta catcgacaag attgagatca ttctcgcaga tgcgactctg   1860
gaggctgaat cggatcttga aaggtga                                       1887
```

<210> SEQ ID NO 14
<211> LENGTH: 628
<212> TYPE: PRT
<213> ORGANISM: Artificial Sequence
<220> FEATURE:
<223> OTHER INFORMATION: translated from synthesized coding region

<400> SEQUENCE: 14

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30
```

-continued

```
Asn Ser Ser Ile Asp Ile Ser Leu Ser Leu Val Gln Phe Leu Val Ser
        35                  40                  45

Asn Phe Val Pro Gly Gly Gly Phe Met Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445
```

```
Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg
625


<210> SEQ ID NO 15
<211> LENGTH: 1887
<212> TYPE: DNA
<213> ORGANISM: Artificial Sequence
<220> FEATURE:
<223> OTHER INFORMATION: synthesized coding region

<400> SEQUENCE: 15

atggataaca accccaacat taacgagtgc atcccgtaca actgcctctc gaatccagaa      60

gaagtgctct tggatggcga gaggatttcg actggcaaca gctccatcga catttccctc     120

tccttggttc agttccttgt gtctaacttc gtccctggcg gtggcttcgc cgttggcctt     180

atcgacttcg tctggggaat tgtcggaccc tcccagtggg atgcgtttct ggtgcagata     240

gagcagctga tcaacgagag gatcgctgag ttcgcgagaa atgctgcaat cgccaacctt     300

gaagggcttg gcaacaactt caacatctac gtggaggcgt tcaaggagtg ggaagaggac     360

cctaagaatc cagcgaccag aacgagggtt atagatcggt tccgcatcct cgatggcctt     420

ttggagaggg acatcccgag cttccgcatt tcgggatttg aggttcctct gctctcagtc     480

tacgctcaag ctgctaatct gcatctggcc atcttgaggg attcagtcat ctttggcgaa     540

cgctggggtc ttacgactat caacgtgaac gagaactaca atcggttgat tcggcacata     600

gacgagtatg ccgaccactg tgctaacacc tacaataggg gtctgaacaa tctgccaaag     660

tcaacgtatc aagactggat aacctacaat aggctcagac gggacctcac tctcaccgtg     720

ctggacatag ctgccttctt tccgaactac gacaaccgga gatatcctat tcaacccgtt     780

ggtcagctca ctcgcgaggt ctacaccgat cccctcatca acttcaatcc ccagctgcaa     840

tcggtcgcac agctgcccac cttcaatgtg atggaaaact cagcgatccg gaatccccat     900

ctgtttgaca tacttaacaa cctcactatc ttcaccgatt ggttttcagt tggacgcaac     960

ttctactggg gagggcacag agtgatttca agcctcattg gaggagggaa cattacatcg    1020
```

```
cctatctatg gaagggaggc caaccaagag ccaccaaggt ctttcacctt caacggtccg   1080
gtgttcagaa cacttagcaa tcccacattg cgcttgctgc aacagccgtg gccagcacca   1140
ccattcaatc tgaggggagt ggagggtgtg gagttctcga cgcctacaaa ctcctttacg   1200
tacagaggca gagggacagt ggactcactg acagaactcc cacctgagga caactctgtt   1260
cctccgaggg agggctactc gcaccggctt tgccatgcca ccttcgtcca gaggtctggc   1320
acgccttttc tgaccactgg ggttgtcttt agctggactc accgctcagc gacgctgacc   1380
aacacaatcg acccagagag gatcaatcag atccctctgg tgaagggctt tcgcgtttgg   1440
ggtggcacaa gcgtgatcac cggacctggt ttcactggtg gggatatcct cagacgcaat   1500
acgtttggcg atttcgtgag ccttcaagtc aacatcaatt ccccaatcac ccagagatat   1560
cggctccgct tcagatacgc ctcatccaga gacgcaaggg tcatcgtcct tactggagca   1620
gccagcaccg gagtcggagg ccaagttagc gtcaacatgc cgttgcagaa aacgatggaa   1680
atcggtgaaa acctcaccag cagaaccttt cgctatacag atttcagcaa ccctttctcc   1740
ttcagagcca atccggacat aatcggcata tccgagcagc ccttgttcgg tgctgggtcc   1800
atctcttctg gcgagctgta catcgacaag attgagatca ttctcgcaga tgcgactctg   1860
gaggctgaat cggatcttga aaggtga                                       1887
```

<210> SEQ ID NO 16
<211> LENGTH: 628
<212> TYPE: PRT
<213> ORGANISM: Artificial Sequence
<220> FEATURE:
<223> OTHER INFORMATION: translated from synthesized coding region

<400> SEQUENCE: 16

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Ala Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205
```

```
Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620
```

Asp Leu Glu Arg
625

<210> SEQ ID NO 17
<211> LENGTH: 1887
<212> TYPE: DNA
<213> ORGANISM: Artificial Sequence
<220> FEATURE:
<223> OTHER INFORMATION: synthesized coding region

<400> SEQUENCE: 17

```
atggataaca accccaacat taacgagtgc atcccgtaca actgcctctc gaatccagaa      60
gaagtgctct tggatggcga gaggatttcg actggcaaca gctccatcga catttccctc     120
tccttggttc agttccttgt gtctaacttc gtccctggcg gtggcttcct tgttggcctt     180
atcgacttcg tctggggaat ttcggaccc tcccagtggg atgcgtttct ggtgcagata     240
gagcagctga tcaacgagag gatcgctgag ttcgcgagaa atgctgcaat cgccaacctt     300
gaagggcttg gcaacaactt caacatctac gtggaggcgt tcaaggagtg ggaagaggac     360
cctaagaatc cagcgaccag aacgagggtt atagatcggt tccgcatcct cgatggcctt     420
ttggagaggg acatcccgag cttccgcatt tcgggatttg aggttcctct gctctcagtc     480
tacgctcaag ctgctaatct gcatctggcc atcttgaggg attcagtcat ctttggcgaa     540
cgctggggtc ttacgactat caacgtgaac gagaactaca atcggttgat tcggcacata     600
gacgagtatg ccgaccactg tgctaacacc tacaataggg gtctgaacaa tctgccaaag     660
tcaacgtatc aagactggat aacctacaat aggctcagac gggacctcac tctcaccgtg     720
ctggacatag ctgccttctt tccgaactac gacaaccgga gatatcctat tcaacccgtt     780
ggtcagctca ctcgcgaggt ctacaccgat cccctcatca acttcaatcc ccagctgcaa     840
tcggtcgcac agctgcccac cttcaatgtg atggaaaact cagcgatccg gaatccccat     900
ctgtttgaca tacttaacaa cctcactatc ttcaccgatt ggttttcagt tggacgcaac     960
ttctactggg gagggcacag agtgatttca agcctcattg gaggagggaa cattacatcg    1020
cctatctatg gaagggaggc caaccaagag ccaccaaggt ctttcacctt caacggtccg    1080
gtgttcagaa cacttagcaa tcccacattg cgcttgctgc aacagccgtg gccagcacca    1140
ccattcaatc tgaggggagt ggagggtgtg gagttctcga cgcctacaaa ctcctttacg    1200
tacagaggca gagggacagt ggactcactg acagaactcc cacctgagga caactctgtt    1260
cctccgaggg agggctactc gcaccggctt tgccatgcca ccttcgtcca gaggtctggc    1320
acgccttttc tgaccactgg ggttgtcttt agctggactc accgctcagc gacgctgacc    1380
aacacaatcg acccagagag gatcaatcag atccctctgg tgaagggctt tcgcgtttgg    1440
ggtggcacaa gcgtgatcac cggacctggt ttcactggtg gggatatcct cagacgcaat    1500
acgtttggcg atttcgtgag ccttcaagtc aacatcaatt ccccaatcac ccagagatat    1560
cggctccgct tcagatacgc ctcatccaga gacgcaaggg tcatcgtcct tactggagca    1620
gccagcaccg gagtcggagg ccaagttagc gtcaacatgc cgttgcagaa aacgatggaa    1680
atcggtgaaa acctcaccag cagaaccttt cgctatacag atttcagcaa ccctttctcc    1740
ttcagagcca atccggacat aatcggcata tccgagcagc ccttgttcgg tgctgggtcc    1800
atctcttctg gcgagctgta catcgacaag attgagatca ttctcgcaga tgcgactctg    1860
gaggctgaat cggatcttga aaggtga                                        1887
```

<210> SEQ ID NO 18

<211> LENGTH: 628
<212> TYPE: PRT
<213> ORGANISM: Artificial Sequence
<220> FEATURE:
<223> OTHER INFORMATION: translated from synthesized coding region

<400> SEQUENCE: 18

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Phe Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380
```

```
Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg
625
```

<210> SEQ ID NO 19
<211> LENGTH: 1887
<212> TYPE: DNA
<213> ORGANISM: Artificial Sequence
<220> FEATURE:
<223> OTHER INFORMATION: synthesized coding region

<400> SEQUENCE: 19

```
atggataaca accccaacat taacgagtgc atcccgtaca actgcctctc gaatccagaa     60

gaagtgctct tggatggcga gaggatttcg actggcaaca gctccatcga catttccctc    120

tccttggttc agttccttgt gtctaacttc gtccctggcg gtggcttcct tgttggcctt    180

atcgacttcg tctggggaat tatcggaccc tcccagtggg atgcgtttct ggtgcagata    240

gagcagctga tcaacgagag gatcgctgag ttcgcgagaa atgctgcaat cgccaacctt    300

gaagggcttg gcaacaactt caacatctac gtggaggcgt tcaaggagtg ggaagaggac    360

cctaagaatc cagcgaccag aacgagggtt atagatcggt tccgcatcct cgatggcctt    420

ttggagaggg acatcccgag cttccgcatt tcgggatttg aggttcctct gctctcagtc    480

tacgctcaag ctgctaatct gcatctggcc atcttgaggg attcagtcat ctttggcgaa    540

cgctggggtc ttacgactat caacgtgaac gagaactaca atcggttgat tcggcacata    600
```

```
gacgagtatg ccgaccactg tgctaacacc tacaataggg gtctgaacaa tctgccaaag    660

tcaacgtatc aagactggat aacctacaat aggctcagac gggacctcac tctcaccgtg    720

ctggacatag ctgccttctt tccgaactac gacaaccgga gatatcctat tcaacccgtt    780

ggtcagctca ctcgcgaggt ctacaccgat cccctcatca acttcaatcc ccagctgcaa    840

tcggtcgcac agctgcccac cttcaatgtg atggaaaact cagcgatccg gaatccccat    900

ctgtttgaca tacttaacaa cctcactatc ttcaccgatt ggttttcagt tggacgcaac    960

ttctactggg gagggcacag agtgatttca agcctcattg gaggagggaa cattacatcg   1020

cctatctatg gaagggaggc caaccaagag ccaccaaggt ctttcacctt caacggtccg   1080

gtgttcagaa cacttagcaa tcccacattg cgcttgctgc aacagccgtg gccagcacca   1140

ccattcaatc tgaggggagt ggagggtgtg gagttctcga cgcctacaaa ctcctttacg   1200

tacagaggca gagggacagt ggactcactg acagaactcc cacctgagga caactctgtt   1260

cctccgaggg agggctactc gcaccggctt tgccatgcca ccttcgtcca gaggtctggc   1320

acgccttttc tgaccactgg ggttgtcttt agctggactc accgctcagc gacgctgacc   1380

aacacaatcg acccagagag gatcaatcag atccctctgg tgaagggctt tcgcgtttgg   1440

ggtggcacaa gcgtgatcac cggacctggt ttcactggtg gggatatcct cagacgcaat   1500

acgtttggcg atttcgtgag ccttcaagtc aacatcaatt ccccaatcac ccagagatat   1560

cggctccgct tcagatacgc ctcatccaga gacgcaaggg tcatcgtcct tactggagca   1620

gccagcaccg gagtcggagg ccaagttagc gtcaacatgc cgttgcagaa aacgatggaa   1680

atcggtgaaa acctcaccag cagaaccttt cgctatacag atttcagcaa ccctttctcc   1740

ttcagagcca atccggacat aatcggcata tccgagcagc ccttgttcgg tgctgggtcc   1800

atctcttctg gcgagctgta catcgacaag attgagatca ttctcgcaga tgcgactctg   1860

gaggctgaat cggatcttga aaggtga                                        1887
```

```
<210> SEQ ID NO 20
<211> LENGTH: 628
<212> TYPE: PRT
<213> ORGANISM: Artificial Sequence
<220> FEATURE:
<223> OTHER INFORMATION: translated from synthesized coding region

<400> SEQUENCE: 20

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Ile Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
```

```
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560
```

```
Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg
625
```

<210> SEQ ID NO 21
<211> LENGTH: 1887
<212> TYPE: DNA
<213> ORGANISM: Artificial Sequence
<220> FEATURE:
<223> OTHER INFORMATION: synthesized coding region

<400> SEQUENCE: 21

```
atggataaca accccaacat taacgagtgc atcccgtaca actgcctctc gaatccagaa     60

gaagtgctct tggatggcga gaggatttcg actggcaaca gctccatcga catttccctc    120

tccttggttc agttccttgt gtctaacttc gtccctggcg gtggcttcct tgttggcctt    180

atcgacttcg tctggggaat tgtcggaccc tcccaggcgg atgcgtttct ggtgcagata    240

gagcagctga tcaacgagag gatcgctgag ttcgcgagaa atgctgcaat cgccaacctt    300

gaagggcttg gcaacaactt caacatctac gtggaggcgt tcaaggagtg ggaagaggac    360

cctaagaatc cagcgaccag aacgagggtt atagatcggt tccgcatcct cgatggcctt    420

ttggagaggg acatcccgag cttccgcatt tcgggatttg aggttcctct gctctcagtc    480

tacgctcaag ctgctaatct gcatctggcc atcttgaggg attcagtcat ctttggcgaa    540

cgctggggtc ttacgactat caacgtgaac gagaactaca atcggttgat tcggcacata    600

gacgagtatg ccgaccactg tgctaacacc tacaataggg gtctgaacaa tctgccaaag    660

tcaacgtatc aagactggat aacctacaat aggctcagac gggacctcac tctcaccgtg    720

ctggacatag ctgccttctt tccgaactac gacaaccgga gatatcctat tcaacccgtt    780

ggtcagctca ctcgcgaggt ctacaccgat cccctcatca acttcaatcc ccagctgcaa    840

tcggtcgcac agctgcccac cttcaatgtg atggaaaact cagcgatccg gaatccccat    900

ctgtttgaca tacttaacaa cctcactatc ttcaccgatt ggttttcagt tggacgcaac    960

ttctactggg gagggcacag agtgatttca agcctcattg gaggagggaa cattacatcg   1020

cctatctatg gaagggaggc caaccaagag ccaccaaggt ctttcacctt caacggtccg   1080

gtgttcagaa cacttagcaa tcccacattg cgcttgctgc aacagccgtg gccagcacca   1140

ccattcaatc tgaggggagt ggagggtgtg gagttctcga cgcctacaaa ctcctttacg   1200

tacagaggca gagggacagt ggactcactg acagaactcc cacctgagga caactctgtt   1260

cctccgaggg agggctactc gcaccggctt tgccatgcca ccttcgtcca gaggtctggc   1320

acgccttttc tgaccactgg ggttgtcttt agctggactc accgctcagc gacgctgacc   1380

aacacaatcg acccagagag gatcaatcag atccctctgg tgaagggctt tcgcgtttgg   1440

ggtggcacaa gcgtgatcac cggacctggt ttcactggtg gggatatcct cagacgcaat   1500

acgtttggcg atttcgtgag ccttcaagtc aacatcaatt ccccaatcac ccagagatat   1560

cggctccgct tcagatacgc ctcatccaga gacgcaaggg tcatcgtcct tactggagca   1620
```

```
gccagcaccg gagtcggagg ccaagttagc gtcaacatgc cgttgcagaa aacgatggaa   1680

atcggtgaaa acctcaccag cagaaccttt cgctatacag atttcagcaa ccctttctcc   1740

ttcagagcca atccggacat aatcggcata tccgagcagc ccttgttcgg tgctgggtcc   1800

atctcttctg gcgagctgta catcgacaag attgagatca ttctcgcaga tgcgactctg   1860

gaggctgaat cggatcttga aaggtga                                          1887
```

<210> SEQ ID NO 22
<211> LENGTH: 628
<212> TYPE: PRT
<213> ORGANISM: Artificial Sequence
<220> FEATURE:
<223> OTHER INFORMATION: translated from synthesized coding region

<400> SEQUENCE: 22

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Ala Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
```

```
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg
625
```

<210> SEQ ID NO 23
<211> LENGTH: 1887
<212> TYPE: DNA
<213> ORGANISM: Artificial Sequence
<220> FEATURE:
<223> OTHER INFORMATION: synthesized coding region

<400> SEQUENCE: 23

```
atggataaca accccaacat taacgagtgc atcccgtaca actgcctctc gaatccagaa      60

gaagtgctct tggatggcga gaggatttcg actggcaaca gctccatcga catttccctc     120

tccttggttc agttccttgt gtctaacttc gtccctggcg gtggcttcct tgttggcctt     180

atcgacttcg tctggggaat tgtcggaccc tcccagtggg atgcgtttct ggtgcagata     240
```

```
gagcagctga tcaacgagag gatcgctgag ttcgcgagaa atgctgcaat cgccaacctt    300

gaagggcttg gcaacaactt caacatctac gtggaggcgt tcaaggagtg ggaagaggac    360

cctaagaatc cagcgaccag aacgagggtt atagatcggt tccgcatcct cgatggcctt    420

ttggagaggg acatcccgag cttccgcatt tcgggatttg aggttcctct gctctcagtc    480

tacgctcaag ctgctaatct gcatctggcc atcttgaggg attcagtcat ctttggcgaa    540

cgctggggtc ttacgactat caacgtgaac gagaactaca atcggttgat tcggcacata    600

gacgagtatg ccgaccactg tgctaacacc tacaataggg gtctgaacaa tctgccaaag    660

tcaacgtatc aagactggat aacctacaat aggctcagac gggacctcac tctcaccgtg    720

ctggacatag ctgccttctt tccgaactac gacaaccgga gatatcctat tcaacccgtt    780

ggtcagctca ctcgcgaggt ctacaccgat cccctcatca acttcaatcc ccagctgcaa    840

tcggtcgcac agctgcccac cttcaatgtg atggaaaact cagcgatccg gaatccccat    900

ctgtttgaca tacttaacaa cctcactatc ttcaccgatt ggttttcagt tggacgcaac    960

ttctactggg gagggcacag agtgatttca agcctcattg gaggagggaa cattacatcg   1020

cctatctatg gaagggaggc caaccaagag ccaccaaggt ctttcacctt caacggtccg   1080

gtgttcagaa cacttagcaa tcccacattg cgcttgctgc aacagccgtg gccagcacca   1140

ccattcaatc tgaggggagt ggagggtgtg gagttctcga cgcctacaaa ctcctttacg   1200

tacagaggca gagggacagt ggactcactg acagaactcc cacctgagga caactctgtt   1260

cctccgaggg agggctactc gcaccggctt tgccatgcca ccttcgtcca gaggtctggc   1320

acgccttttc tgaccactgg ggttgtcttt agctggactc accgctcagc gacgctgacc   1380

aacacaatcg acccagagag gatcaatcag atccctctgg tgaagggctt tcgcgtttgg   1440

ggtggcacaa gcgtgatcac cggacctggt ttcactggtg gggatatcct cagacgcaat   1500

acgtttggcg atttcgtgag ccttcaagtc aacatcaatt ccccaatcac ccagagatat   1560

cggctccgct tcagatacgc ctcatccaga gacgcaaggg tcatcgtcct tactggagca   1620

gccagcaccg gagtcggagg ccaagttagc gtcaacatgc cgttgcagaa aacgatggaa   1680

atcggtgaaa acctcaccag cagaaccttt cgctatacag atttcagcaa ccctttctcc   1740

ttcagagcca atccggacat aatcggcata tccgagcagc ccttgatggg tgctgggtcc   1800

atctcttctg gcgagctgta catcgacaag attgagatca ttctcgcaga tgcgactctg   1860

gaggctgaat cggatcttga aaggtga                                       1887
```

```
<210> SEQ ID NO 24
<211> LENGTH: 628
<212> TYPE: PRT
<213> ORGANISM: Artificial Sequence
<220> FEATURE:
<223> OTHER INFORMATION: translated from synthesized coding region

<400> SEQUENCE: 24

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60
```

```
Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
```

```
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Met Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg
625


<210> SEQ ID NO 25
<211> LENGTH: 1887
<212> TYPE: DNA
<213> ORGANISM: Artificial Sequence
<220> FEATURE:
<223> OTHER INFORMATION: synthesized coding region

<400> SEQUENCE: 25

atggataaca accccaacat taacgagtgc atcccgtaca actgcctctc gaatccagaa      60

gaagtgctct tggatggcga gaggatttcg actggcaaca gctccatcga catttccctc     120

tccttggttc agttccttgt gtctaacttc gtccctggcg gtggcttcct tgttggcctt     180

atcgacttcg tctggggaat tgtcggaccc tcccagtggg atgcgtttct ggtgcagata     240

gagcagctga tcaacgagag gatcgctgag ttcgcgagaa atgctgcaat cgccaacctt     300

gaagggcttg gcaacaactt caacatctac gtggaggcgt tcaaggagtg ggaagaggac     360

cctaagaatc cagcgaccag aacgagggtt atagatcggt tccgcatcct cgatggcctt     420

ttggagaggg acatcccgag cttccgcatt tcgggatttg aggttcctct gctctcagtc     480

tacgctcaag ctgctaatct gcatctggcc atcttgaggg attcagtcat ctttggcgaa     540

cgctggggtc ttacgactat caacgtgaac gagaactaca atcggttgat tcggcacata     600

gacgagtatg ccgaccactg tgctaacacc tacaataggg gtctgaacaa tctgccaaag     660

tcaacgtatc aagactggat aacctacaat aggctcagac gggacctcac tctcaccgtg     720

ctggacatag ctgccttctt tccgaactac gacaaccgga gatatcctat tcaacccgtt     780

ggtcagctca ctcgcgaggt ctacaccgat cccctcatca acttcaatcc ccagctgcaa     840

tcggtcgcac agctgcccac cttcaatgtg atggaaaact cagcgatccg gaatccccat     900

ctgtttgaca tacttaacaa cctcactatc ttcaccgatt ggttttcagt tggacgcaac     960

ttctactggg gagggcacag agtgatttca agcctcattg gaggagggaa cattacatcg    1020

cctatctatg gaagggaggc caaccaagag ccaccaaggt ctttcacctt caacggtccg    1080

gtgttcagaa cacttagcaa tcccacattg cgcttgctgc aacagccgtg gccagcacca    1140

ccattcaatc tgaggggagt ggagggtgtg gagttctcga cgcctacaaa ctcctttacg    1200
```

```
tacagaggca gagggacagt ggactcactg acagaactcc cacctgagga caactctgtt   1260

cctccgaggg agggctactc gcaccggctt tgccatgcca ccttcgtcca gaggtctggc   1320

acgccttttc tgaccactgg ggttgtcttt agctggactc accgctcagc gacgctgacc   1380

aacacaatcg acccagagag gatcaatcag atccctctgg tgaagggctt tcgcgtttgg   1440

ggtggcacaa gcgtgatcac cggacctggt ttcactggtg ggatatcct cagacgcaat    1500

acgtttggcg atttcgtgag ccttcaagtc aacatcaatt ccccaatcac ccagagatat   1560

cggctccgct tcagatacgc ctcatccaga gacgcaaggg tcatcgtcct tactggagca   1620

gccagcaccg gagtcggagg ccaagttagc gtcaacatgc cgttgcagaa aacgatggaa   1680

atcggtgaaa acctcaccag cagaaccttt cgctatacag atttcagcaa ccctttctcc   1740

ttcagagcca atccggacat aatcggcata tccgagcagc ccttggccgg tgctgggtcc   1800

atctcttctg gcgagctgta catcgacaag attgagatca ttctcgcaga tgcgactctg   1860

gaggctgaat cggatcttga aaggtga                                        1887
```

```
<210> SEQ ID NO 26
<211> LENGTH: 628
<212> TYPE: PRT
<213> ORGANISM: Artificial Sequence
<220> FEATURE:
<223> OTHER INFORMATION: translated from synthesized coding region

<400> SEQUENCE: 26

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240
```

```
Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Ala Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg
625

<210> SEQ ID NO 27
<211> LENGTH: 1887
<212> TYPE: DNA
```

<213> ORGANISM: Artificial Sequence
<220> FEATURE:
<223> OTHER INFORMATION: synthesized coding region

<400> SEQUENCE: 27

```
atggataaca accccaacat taacgagtgc atcccgtaca actgcctctc gaatccagaa      60

gaagtgctct tggatggcga gaggatttcg actggcaaca gctccatcga catttccctc     120

tccttggttc agttccttgt gtctaacttc gtccctggcg ccggcttcct tgttggcctt     180

atcgacttcg tctggggaat tgtcggaccc tcccagatgg atgcgtttct ggtgcagata     240

gagcagctga tcaacgagag gatcgctgag ttcgcgagaa atgctgcaat cgccaacctt     300

gaagggcttg gcaacaactt caacatctac gtggaggcgt tcaaggagtg ggaagaggac     360

cctaagaatc cagcgaccag aacgagggtt atagatcggt tccgcatcct cgatggcctt     420

ttggagaggg acatcccgag cttccgcatt tcgggatttg aggttcctct gctctcagtc     480

tacgctcaag ctgctaatct gcatctggcc atcttgaggg attcagtcat ctttggcgaa     540

cgctggggtc ttacgactat caacgtgaac gagaactaca atcggttgat tcggcacata     600

gacgagtatg ccgaccactg tgctaacacc tacaataggg gtctgaacaa tctgccaaag     660

tcaacgtatc aagactggat aacctacaat aggctcagac gggacctcac tctcaccgtg     720

ctggacatag ctgccttctt tccgaactac gacaaccgga gatatcctat tcaacccgtt     780

ggtcagctca ctcgcgaggt ctacaccgat cccctcatca acttcaatcc ccagctgcaa     840

tcggtcgcac agctgcccac cttcaatgtg atggaaaact cagcgatccg gaatccccat     900

ctgtttgaca tacttaacaa cctcactatc ttcaccgatt ggttttcagt tggacgcaac     960

ttctactggg gagggcacag agtgatttca agcctcattg gaggagggaa cattacatcg    1020

cctatctatg gaagggaggc caaccaagag ccaccaaggt ctttcacctt caacggtccg    1080

gtgttcagaa cacttagcaa tcccacattg cgcttgctgc aacagccgtg gccagcacca    1140

ccattcaatc tgaggggagt ggagggtgtg gagttctcga cgcctacaaa ctcctttacg    1200

tacagaggca gagggacagt ggactcactg acagaactcc cacctgagga caactctgtt    1260

cctccgaggg agggctactc gcaccggctt tgccatgcca ccttcgtcca gaggtctggc    1320

acgccttttc tgaccactgg ggttgtcttt agctggactc accgctcagc gacgctgacc    1380

aacacaatcg acccagagag gatcaatcag atccctctgg tgaagggctt tcgcgtttgg    1440

ggtggcacaa gcgtgatcac cggacctggt ttcactggtg gggatatcct cagacgcaat    1500

acgtttggcg atttcgtgag ccttcaagtc aacatcaatt ccccaatcac ccagagatat    1560

cggctccgct tcagatacgc ctcatccaga gacgcaaggg tcatcgtcct tactggagca    1620

gccagcaccg gagtcggagg ccaagttagc gtcaacatgc cgttgcagaa aacgatggaa    1680

atcggtgaaa acctcaccag cagaaccttt cgctatacag atttcagcaa ccctttctcc    1740

ttcagagcca atccggacat aatcggcata tccgagcagc ccttgttcgg tgctgggtcc    1800

atctcttctg gcgagctgta catcgacaag attgagatca ttctcgcaga tgcgactctg    1860

gaggctgaat cggatcttga aaggtga                                        1887
```

<210> SEQ ID NO 28
<211> LENGTH: 628
<212> TYPE: PRT
<213> ORGANISM: Artificial Sequence
<220> FEATURE:
<223> OTHER INFORMATION: translated from synthesized coding region

<400> SEQUENCE: 28

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Ala Gly Phe Leu Val Gly Leu Ile Asp Phe Val
    50                  55                  60

Trp Gly Ile Val Gly Pro Ser Gln Met Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415
```

```
Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg
625
```

<210> SEQ ID NO 29
<211> LENGTH: 1887
<212> TYPE: DNA
<213> ORGANISM: Artificial Sequence
<220> FEATURE:
<223> OTHER INFORMATION: synthesized coding region

<400> SEQUENCE: 29

```
atggataaca accccaacat taacgagtgc atcccctaca actgcctctc gaatccagaa     60

gaagtgctct tggatggcga gaggatttcg actggcaaca gctccataga catttccctc    120

tccttggttc agttccttgt gtctaacttc gtccctggcg gtggcttcct tgttggatta    180

atcgacttcg tctggggaat tgtcggaccc tcccagtggg atgcgtttct ggtgcagata    240

gagcaattaa ttaatgaaag gatcgctgag ttcgcgagaa atgctgcaat cgccaacctt    300

gaagggcttg gcaacaactt caacatctac gtggaagcat ttaaggagtg ggaagaggac    360

cctaagaatc cagcgaccag aacgagggtt atagatcggt tccgcatcct cgatggcctt    420

ttggagaggg acatcccgag cttccgcatt tcgggatttg aggttcctct gctctcagtc    480

tacgctcaag ctgctaatct gcatctggcc atcttgaggg attcagtcat ctttggcgaa    540

cgctggggtc ttacgactat caacgtgaat gaaaactaca atcggttgat tcggcacata    600

gacgagtatg ccgaccactg tgctaacacc tacaataggg gattaaataa tctgccaaag    660

tcaacgtatc aagactggat aacatataat aggctcagac gggacctcac tctcaccgtg    720

ctggacatag ctgccttctt tccgaactac gacaaccgga gatatcctat tcaacccgtt    780

ggtcagctca ctcgcgaggt ctacaccgat ccattaatta atttcaatcc ccagctgcaa    840
```

```
tcggtcgcac agctgcccac cttcaatgtg atggaaaact cagcgatccg gaatccccat    900

ctctttgaca tacttaataa tctcactatc ttcaccgatt ggttttcagt tggacgcaac    960

ttctactggg gagggcacag agtgatttca agcctcattg gaggagggaa cattacatcg   1020

cctatctatg gaagggaggc caaccaggag ccaccaaggt ctttcacctt caacggtccg   1080

gtgttcagaa cacttagcaa tcccacattg cgcttgctgc aacagccgtg gccagcacca   1140

ccattcaatc tgaggggagt ggagggtgtg gagttctcga cgcctacaaa ctcctttacg   1200

tacagaggca gagggacagt ggactcactg acagaactcc cacctgagga caactctgtt   1260

cctccgaggg agggctactc gcaccggctt tgccatgcca ccttcgtcca gaggtctggc   1320

acgccttttc tgaccactgg ggttgtcttt agctggactc accgctcagc gacgctgacc   1380

aatacaatcg acccagagag aattaatcaa atccctctgg tgaagggctt tcgcgtttgg   1440

ggtggcacaa gcgtgatcac cggacctggt ttcactggtg gggatatcct cagacgcaat   1500

acgtttggcg atttcgtgag ccttcaagtc aacattaatt ccccaatcac ccagagatat   1560

cggctccgct tcagatacgc ctcatccaga gacgcaaggg tcatcgtcct tactggagca   1620

gccagcaccg gagtcggagg ccaagttagc gtcaacatgc cgttgcagaa aacgatggaa   1680

atcggtgaaa acctcaccag cagaaccttt cgctatacag atttcagcaa ccctttctcc   1740

ttcagagcca atccggatat aatcggcata tccgagcagc ccttgttcgg tgctgggtcc   1800

atctcttcag gcgagctgta catcgataaa attgagatca ttctcgcaga tgcgactctc   1860

gaggctgaat cggatcttga aaggtga                                       1887
```

```
<210> SEQ ID NO 30
<211> LENGTH: 628
<212> TYPE: PRT
<213> ORGANISM: Bacillus thuringiensis

<400> SEQUENCE: 30

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
```

```
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605
```

```
Asp Lys Ile Glu Ile Ile Leu Ala Asp Ala Thr Leu Glu Ala Glu Ser
    610                 615                 620

Asp Leu Glu Arg
625


<210> SEQ ID NO 31
<211> LENGTH: 1887
<212> TYPE: DNA
<213> ORGANISM: Artificial Sequence
<220> FEATURE:
<223> OTHER INFORMATION: synthesized coding region

<400> SEQUENCE: 31

atggataaca acccgaacat caacgagtgc atcccctaca actgcctgag caaccccgag     60

gaggtgctgc tggacggcga gaggatctca accggcaaca gcagcatcga catcagcctg    120

tccctggtgc agttcctggt gagcaacttc gtgccgggcg gcggcttcct ggtgggatta    180

atcgacttcg tgtggggcat cgtcggcccg tcccagtggg acgccttcct ggttcagatc    240

gagcaattaa ttaatgaaag gatagcagag ttcgcgagga acgcggccat cgccaacctg    300

gagggcctgg gcaacaactt caacatctac gtggaagcat ttaaggagtg ggaggaggac    360

cccaagaacc cggccacgag gacgagggtg atcgaccgct ttcgcatcct ggacggcctg    420

ctggagaggg acatcccgtc cttcagaatc agcggcttcg aggtcccgct gctgtccgtg    480

tacgcgcaag cggccaacct gcacctggcg atcctgaggg actccgtgat attcggcgag    540

aggtggggcc tgaccaccat caacgtgaat gaaaactaca accggctgat aaggcacatc    600

gacgagtacg ccgaccactg cgccaacacc tacaataggg gattaaataa tctgcccaag    660

agcacctacc aagactggat cacatataac cggctgagga gggacctgac cctgaccgtg    720

ctggacatcg ccgcgttctt cccgaactac gacaataggc gctacccgat ccagccggtg    780

ggccagctga cccgcgaggt gtacaccgac ccattaatta atttcaaccc gcagctccag    840

tccgtggccc agctgccgac cttcaacgtg atggagaaca gcgccatccg gaacccgcac    900

ctgttcgaca tcctgaataa tctgaccatc ttcaccgact ggttctcagt gggccggaac    960

ttctactggg gcggccatag ggtgatctcc agcctgatcg gcggcggcaa catcacctcc   1020

ccgatctacg ggagggaggc gaaccaggag ccgccgaggt ccttcacctt caacggcccg   1080

gtgtttagga ccctgtccaa cccgaccctg aggctgctcc agcagccgtg gccggcgccg   1140

ccgttcaacc tgaggggcgt ggagggcgtg gagttcagca ccccgaccaa cagcttcacc   1200

taccggggga ggggcaccgt ggactcactg accgagctgc cgccggagga caacagcgtg   1260

ccgccgaggg agggctacag ccataggctg tgccacgcca ccttcgtgca gaggagcggc   1320

accccgttct tgacgaccgg cgtggtgttc tcctggaccc accggagcgc gaccctgacc   1380

aatacaatcg acccggagag aattaatcaa atcccgctgg tgaagggctt ccgggtgtgg   1440

ggcggcacct ccgtgatcac cgggccgggc tttaccggcg gcgacatcct gaggaggaac   1500

acgttcggcg acttcgtgag cctccaagtg aacattaata gcccgatcac ccagcgctac   1560

cggctgaggt tccgctacgc gtcaagccgc gacgcgaggg tgatcgtgct gaccggcgcg   1620

gcctcaaccg gcgtgggcgg ccaagtgtcc gtgaacatgc cgctgcaaaa gacgatggag   1680

atcggcgaga acctgacctc aaggaccttc cgctacaccg acttcagcaa cccgttcagc   1740

tttagggcca acccggatat aatcggcatc agcgagcagc cgctgttcgg cgccggctcc   1800

atctcaagcg gcgagctgta catcgataaa atcgagatca tcctggcgga cgcgaccttg   1860
```

gaggccgagt ccgacctgga gaggtga 1887

<210> SEQ ID NO 32
<211> LENGTH: 628
<212> TYPE: PRT
<213> ORGANISM: Bacillus thuringiensis

<400> SEQUENCE: 32

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365
```

```
Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg
625
```

<210> SEQ ID NO 33
<211> LENGTH: 1887
<212> TYPE: DNA
<213> ORGANISM: Artificial Sequence
<220> FEATURE:
<223> OTHER INFORMATION: synthesized coding region

<400> SEQUENCE: 33

```
atggacaaca atcccaatat caatgagtgc atcccataca actgcctttc aaatcccgag      60

gaagtcttac tggatgggga aaggattagc actggcaatt ccagcattga catttccttg     120

agtctcgttc aattccttgt gagcaacttt gtgcctggcg gagggttctt ggttggtctc     180

atagactttg tttggggaat tgtaggacca tcacagtggg atgccttctt agtccagatt     240

gaacagctta tcaatgagag aatagctgag ttcgcaagaa atgctgcaat cgctaacttg     300

gagggactcg gcaacaactt caacatctac gtggaggctt tcaaagaatg ggaagaagat     360

cctaagaatc cagctactag gactagagtc atcgataggt ttaggattct tgatgggctg     420

ttggagcgtg acattccttc ctttaggatt agtggcttcg aggttcctct cctttctgtc     480

tatgctcaag cagccaatct ccatctcgcc attctccgtg attcagtaat cttcggagaa     540
```

```
agatggggtt tgacaacgat caatgtgaat gagaactaca acagattgat cagacacatt    600

gatgagtatg ctgatcattg tgctaacaca tacaacagag ggcttaacaa cctcccgaaa    660

tcaacatatc aagattggat aacctacaat agattgagga gggatctcac actgactgta    720

ctcgacattg ctgctttctt tcccaactac gataaccgta gatatcccat tcaacccgtc    780

ggacaactca ctcgtgaagt gtacacagat ccccttatca acttcaaccc acagttacaa    840

agtgttgcac agctgccaac cttcaatgtg atggaaaact ctgccattag gaatccacat    900

ctgtttgaca tacttaacaa cttgactatc tttacggatt ggtttagtgt ggggaggaac    960

ttctattggg gaggtcacag agtgattagc tctcttatcg gaggtgggaa cattacttca   1020

ccaatctatg gacgtgaagc aaatcaagaa ccaccacgtt cattcacctt caatggaccc   1080

gttttcagaa cactgtccaa tccgactctg agactgttgc agcaaccttg gccagcacct   1140

cctttcaact tgaggggtgt agagggagtc gagttttcca cacctactaa cagtttcacc   1200

tataggggtc gtggaactgt tgattctctt actgaacttc ctccagagga caattctgtt   1260

cctccgaggg aaggctattc acaccgtttg tgtcatgcaa cttttgttca gaggtctggc   1320

acacctttct taacaactgg cgtcgttttc agctggacac ataggagtgc aaccctcacg   1380

aatactatcg atccagagag aatcaatcag attcctcttg ttaagggctt tagggtgtgg   1440

ggtgggacct cagtgataac tggtcccggt ttcaccggag gagacatact tagaaggaac   1500

acctttgggg atttcgtttc tcttcaagta aacatcaatt ctcctatcac ccagagatac   1560

agacttaggt ttagatatgc tagtagccgt gacgccagag tcatagtgtt gactggtgct   1620

gcatcaactg gtgttggtgg gcaagtttca gtgaacatgc cacttcaaaa gacaatggag   1680

ataggtgaga acttgacgtc cagaaccttc agatacactg acttttctaa tcctttctct   1740

tttcgtgcta atccagacat cataggaatc agtgaacaac cgttgtttgg agctggttcc   1800

atttctagtg gagaattgta cattgacaag attgagatca tacttgccga tgccacgctc   1860

gaggctgaat ctgatctcga aaggtga                                       1887
```

<210> SEQ ID NO 34
<211> LENGTH: 628
<212> TYPE: PRT
<213> ORGANISM: Bacillus thuringiensis

<400> SEQUENCE: 34

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
```

```
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560
```

```
Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg
625


<210> SEQ ID NO 35
<211> LENGTH: 3495
<212> TYPE: DNA
<213> ORGANISM: Artificial Sequence
<220> FEATURE:
<223> OTHER INFORMATION: synthesized coding region

<400> SEQUENCE: 35

atggacaaca atcccaatat caatgagtgc atcccataca actgcctttc aaatcccgag     60

gaagtcttac tggatgggga aaggattagc actggcaatt ccagcattga catttccttg    120

agtctcgttc aattccttgt gagcaacttt gtgcctggcg gagggttctt ggttggtctc    180

atagactttg tttggggaat tgtaggacca tcacagtggg atgccttctt agtccagatt    240

gaacagctta tcaatgagag aatagctgag ttcgcaagaa atgctgcaat cgctaacttg    300

gagggactcg gcaacaactt caacatctac gtggaggctt tcaaagaatg ggaagaagat    360

cctaagaatc cagctactag gactagagtc atcgataggt ttaggattct tgatgggctg    420

ttggagcgtg acattccttc ctttaggatt agtggcttcg aggttcctct cctttctgtc    480

tatgctcaag cagccaatct ccatctcgcc attctccgtg attcagtaat cttcggagaa    540

agatggggtt tgacaacgat caatgtgaat gagaactaca acagattgat cagacacatt    600

gatgagtatg ctgatcattg tgctaacaca tacaacagag ggcttaacaa cctcccgaaa    660

tcaacatatc aagattggat aacctacaat agattgagga gggatctcac actgactgta    720

ctcgacattg ctgctttctt tcccaactac gataaccgta gatatcccat tcaacccgtc    780

ggacaactca ctcgtgaagt gtacacagat ccccttatca acttcaaccc acagttacaa    840

agtgttgcac agctgccaac cttcaatgtg atggaaaact ctgccattag gaatccacat    900

ctgtttgaca tacttaacaa cttgactatc tttacggatt ggtttagtgt ggggaggaac    960

ttctattggg gaggtcacag agtgattagc tctcttatcg gaggtgggaa cattacttca   1020

ccaatctatg gacgtgaagc aaatcaagaa ccaccacgtt cattcacctt caatggaccc   1080

gttttcagaa cactgtccaa tccgactctg agactgttgc agcaaccttg gccagcacct   1140

cctttcaact tgaggggtgt agagggagtc gagttttcca cacctactaa cagtttcacc   1200

tataggggtc gtggaactgt tgattctctt actgaacttc ctccagagga caattctgtt   1260

cctccgaggg aaggctattc acaccgtttg tgtcatgcaa cttttgttca gaggtctggc   1320

acacctttct taacaactgg cgtcgttttc agctggacac ataggagtgc aaccctcacg   1380

aatactatcg atccagagag aatcaatcag attcctcttg ttaagggctt tagggtgtgg   1440

ggtgggacct cagtgataac tggtcccggt ttcaccggag gagacatact tagaaggaac   1500

acctttgggg atttcgtttc tcttcaagta aacatcaatt ctcctatcac ccagagatac   1560

agacttaggt ttagatatgc tagtagccgt gacgccagag tcatagtgtt gactggtgct   1620
```

```
gcatcaactg gtgttggtgg gcaagtttca gtgaacatgc cacttcaaaa gacaatggag   1680
ataggtgaga acttgacgtc cagaaccttc agatacactg acttttctaa tcctttctct   1740
tttcgtgcta atccagacat cataggaatc agtgaacaac cgttgtttgg agctggttcc   1800
atttctagtg gagaattgta cattgacaag attgagatca tacttgccga tgccacgctc   1860
gaggctgaat ctgatctcga aagggcacag aaagctgtaa acgcattgtt tacaagttct   1920
aatcaaatcg gactcaaaac cgatgttacg gactatcaca tagatagggt ttctaatctt   1980
gtggaatgtc tttcagatga gttttgttta gatgagaaga aagaactttc agaaaaggtc   2040
aagcacgcca aaagactgtc cgatgaaagg aatctccttc aagacccaaa ctttcgtgga   2100
atcaataggc agctcgacag aggttggaga gggagcacag atatcaccat tcaaggagga   2160
gatgacgttt tcaaagagaa ctatgtcacc ttgttaggca cctttgatga gtgctatcca   2220
acttatctgt atcagaagat tgatgaatcc aagctgaagg cttacacaag atatcagctc   2280
agaggataca tcgaggactc ccaagatttg gagatatact tgattcgtta caatgcaaaa   2340
catgagaccg tgaatgttcc tggtactgga agtctctggc cactgtctgc tccgtcacct   2400
attgggaaat gtgcccatca ctcccaccat ttctcattgg acatagacgt tggctgcaca   2460
gatttgaatg aagatttggg tgtttgggtc atcttcaaga tcaaaactca agacggacac   2520
gctcgtttag gaaacttaga gtttcttgaa gagaagccct tggttgggga ggcacttgcc   2580
agagtaaaga gagctgaaaa gaagtggaga gataagaggg agaaacttga gtgggagact   2640
aacattgtgt acaaggaagc caaagaaagc gtggatgctc ttttcgtgaa ctctcagtat   2700
gataggttac aagcagacac caacatagca atgatacatg cagctgacaa aagagtccat   2760
tctattcgtg aggcttactt gccagaactt agtgtgattc ccggtgtcaa cgctgccatt   2820
ttcgaggaat tggaaggaag aatctttacg gctttcagcc tctatgacgc taggaatgtt   2880
atcaagaatg gtgatttcaa caatggcctc tcatgttgga atgtgaaagg tcatgttgat   2940
gtagaggagc aaaacaatca ccgtagcgtg ctggttgtcc cagaatggga agccgaagta   3000
agccaagaag ttagagtttg ccctggaaga ggctacattc tgcgtgtcac cgcttacaaa   3060
gaaggatatg gcgaagggtg cgtgactatt catgagattg agaacaatac tgacgaactt   3120
aagttttcaa actgcgtcga ggaggaagtg tatcctaaca acacagtgac ttgtaatgac   3180
tatacagcaa cgcaagagga atacgagggg acatacacca gtcgtaatcg tggttatgat   3240
ggtgcttatg aaagcaattc atccgttcca gctgactatg ccagtgccta cgaagagaag   3300
gcttacacgg atggcagaag agataaccca tgtgagtcca acagaggtta tggtgattac   3360
actcctcttc cagctggtta cgtgactaaa gagttagagt actttccgga gactgataag   3420
gtttggattg aaatcggaga gacagaaggg acattcatag tagattcagt tgagcttctt   3480
ctcatggaag aatga                                                     3495
```

<210> SEQ ID NO 36
<211> LENGTH: 1164
<212> TYPE: PRT
<213> ORGANISM: Artificial Sequence
<220> FEATURE:
<223> OTHER INFORMATION: translated from synthesized coding region

<400> SEQUENCE: 36

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
```

```
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445
```

```
Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg Ala Gln Lys Ala Val Asn Ala Leu Phe Thr Ser Ser
625                 630                 635                 640

Asn Gln Ile Gly Leu Lys Thr Asp Val Thr Asp Tyr His Ile Asp Arg
                645                 650                 655

Val Ser Asn Leu Val Glu Cys Leu Ser Asp Glu Phe Cys Leu Asp Glu
            660                 665                 670

Lys Lys Glu Leu Ser Glu Lys Val Lys His Ala Lys Arg Leu Ser Asp
        675                 680                 685

Glu Arg Asn Leu Leu Gln Asp Pro Asn Phe Arg Gly Ile Asn Arg Gln
    690                 695                 700

Leu Asp Arg Gly Trp Arg Gly Ser Thr Asp Ile Thr Ile Gln Gly Gly
705                 710                 715                 720

Asp Asp Val Phe Lys Glu Asn Tyr Val Thr Leu Leu Gly Thr Phe Asp
                725                 730                 735

Glu Cys Tyr Pro Thr Tyr Leu Tyr Gln Lys Ile Asp Glu Ser Lys Leu
            740                 745                 750

Lys Ala Tyr Thr Arg Tyr Gln Leu Arg Gly Tyr Ile Glu Asp Ser Gln
        755                 760                 765

Asp Leu Glu Ile Tyr Leu Ile Arg Tyr Asn Ala Lys His Glu Thr Val
    770                 775                 780

Asn Val Pro Gly Thr Gly Ser Leu Trp Pro Leu Ser Ala Pro Ser Pro
785                 790                 795                 800

Ile Gly Lys Cys Ala His His Ser His His Phe Ser Leu Asp Ile Asp
                805                 810                 815

Val Gly Cys Thr Asp Leu Asn Glu Asp Leu Gly Val Trp Val Ile Phe
            820                 825                 830

Lys Ile Lys Thr Gln Asp Gly His Ala Arg Leu Gly Asn Leu Glu Phe
        835                 840                 845

Leu Glu Glu Lys Pro Leu Val Gly Glu Ala Leu Ala Arg Val Lys Arg
    850                 855                 860
```

```
Ala Glu Lys Lys Trp Arg Asp Lys Arg Glu Lys Leu Glu Trp Glu Thr
865                 870                 875                 880

Asn Ile Val Tyr Lys Glu Ala Lys Glu Ser Val Asp Ala Leu Phe Val
                885                 890                 895

Asn Ser Gln Tyr Asp Arg Leu Gln Ala Asp Thr Asn Ile Ala Met Ile
            900                 905                 910

His Ala Ala Asp Lys Arg Val His Ser Ile Arg Glu Ala Tyr Leu Pro
        915                 920                 925

Glu Leu Ser Val Ile Pro Gly Val Asn Ala Ala Ile Phe Glu Glu Leu
    930                 935                 940

Glu Gly Arg Ile Phe Thr Ala Phe Ser Leu Tyr Asp Ala Arg Asn Val
945                 950                 955                 960

Ile Lys Asn Gly Asp Phe Asn Asn Gly Leu Ser Cys Trp Asn Val Lys
                965                 970                 975

Gly His Val Asp Val Glu Glu Gln Asn Asn His Arg Ser Val Leu Val
            980                 985                 990

Val Pro Glu Trp Glu Ala Glu Val  Ser Gln Glu Val Arg  Val Cys Pro
        995                 1000                1005

Gly Arg  Gly Tyr Ile Leu Arg  Val Thr Ala Tyr Lys  Glu Gly Tyr
    1010                1015                1020

Gly Glu  Gly Cys Val Thr Ile  His Glu Ile Glu Asn  Asn Thr Asp
    1025                1030                1035

Glu Leu  Lys Phe Ser Asn Cys  Val Glu Glu Glu Val  Tyr Pro Asn
    1040                1045                1050

Asn Thr  Val Thr Cys Asn Asp  Tyr Thr Ala Thr Gln  Glu Glu Tyr
    1055                1060                1065

Glu Gly  Thr Tyr Thr Ser Arg  Asn Arg Gly Tyr Asp  Gly Ala Tyr
    1070                1075                1080

Glu Ser  Asn Ser Ser Val Pro  Ala Asp Tyr Ala Ser  Ala Tyr Glu
    1085                1090                1095

Glu Lys  Ala Tyr Thr Asp Gly  Arg Arg Asp Asn Pro  Cys Glu Ser
    1100                1105                1110

Asn Arg  Gly Tyr Gly Asp Tyr  Thr Pro Leu Pro Ala  Gly Tyr Val
    1115                1120                1125

Thr Lys  Glu Leu Glu Tyr Phe  Pro Glu Thr Asp Lys  Val Trp Ile
    1130                1135                1140

Glu Ile  Gly Glu Thr Glu Gly  Thr Phe Ile Val Asp  Ser Val Glu
    1145                1150                1155

Leu Leu  Leu Met Glu Glu
    1160
```

<210> SEQ ID NO 37
<211> LENGTH: 3495
<212> TYPE: DNA
<213> ORGANISM: Artificial Sequence
<220> FEATURE:
<223> OTHER INFORMATION: synthesized coding region

<400> SEQUENCE: 37

```
atggataaca atccgaacat caatgaatgc atcccgtaca actgcctgag caacccggaa     60

gaagtgctgt tggatggaga acggatatca actggtaatt catcaattga tatttctctg    120

tcacttgttc agtttctggt atctaacttc gtcccaggcg gaggattcct ggttggatta    180

atagattttg tatggggaat agttggccct tctcaatggg atgcatttct agtacaaatt    240

gaacaattaa ttaatgaaag aatagctgaa tttgctagga atgctgctat tgctaattta    300
```

```
gaaggattag gaaacaattt caatatatat gtggaagcat ttaaagaatg ggaagaagat    360
cctaagaatc cagcaaccag gaccagagta attgatcgct ttcgtatact tgatgggcta    420
cttgaaaggg acattccttc gtttcgaatt tctggatttg aagtacccct tttatccgtt    480
tatgctcaag cggccaatct gcatctagct atattaagag attctgtaat ttttggagaa    540
agatggggat tgacaacgat aaatgtcaat gaaaactata atagactaat taggcatatt    600
gatgaatatg ctgatcactg tgcaaatacg tataatcggg gattaaataa tttaccgaaa    660
tctacgtatc aagattggat aacatataat cgattgcgga gagacttaac attgactgta    720
ttagatatcg ccgctttctt tccaaactat gacaatagga gatatccaat tcagccagtt    780
ggtcaactaa caagggaagt ttatacggac ccattaatta attttaatcc acagttacag    840
tctgtagctc aattacctac ttttaacgtt atggagaaca gcgcaattag aaatcctcat    900
ttatttgata tattgaataa tcttacaatc tttacggatt ggtttagtgt tggacgcaat    960
ttttattggg gaggacatcg agtaatatct agccttatag gaggtggtaa cataacatct   1020
cctatatatg gaagagaggc gaaccaggag cctccaagat cctttacttt taatggaccg   1080
gtatttagga ctttatcaaa tcctacttta cgattattac agcaaccttg gccagcgcca   1140
ccatttaatt tacgtggtgt tgaaggagta gaattttcta cacctacaaa tagctttacg   1200
tatcgaggaa gaggtacggt tgattcttta actgaattgc cgcctgagga taatagtgtg   1260
ccacctcgcg aaggatatag tcatcgttta tgtcatgcaa cttttgttca aagatctgga   1320
acaccttttt taacaactgg tgtagtattt tcttggacgc atcgtagtgc aactcttaca   1380
aatacaattg atccagagag aattaatcaa atacctttag tgaaaggatt tagagtttgg   1440
gggggcacct ctgtcattac aggaccagga tttacaggag gggatatcct tcgaagaaat   1500
acctttggtg attttgtatc tctacaagtc aatattaatt caccaattac ccaaagatac   1560
cgtttaagat ttcgttacgc ttccagtagg gatgcacgag ttatagtatt aacaggagcg   1620
gcatccacag gagtgggagg ccaagttagt gtaaatatgc ctcttcagaa aactatggaa   1680
atagggggaga acttaacatc tagaacattt agatataccg attttagtaa tcctttttca   1740
tttagagcta atccagatat aattgggata agtgaacaac ctctatttgg tgcaggttct   1800
attagtagcg gtgaacttta tatagataaa attgaaatta ttctagcaga tgcaacattt   1860
gaagcagaat ctgatttaga aagagcacaa aaggcggtga atgccctgtt tacttcttcc   1920
aatcaaatcg ggttaaaaac cgatgtgacg gactatcata tcgatcgagt atccaattta   1980
gttgagtgtt tatctgatga attttgtctg gatgaaaaaa aagaattgtc cgagaaagtc   2040
aaacatgcga agcgacttag tgatgagcgg aatttacttc aagatccaaa ctttagaggg   2100
atcaatagac aactagaccg tggctggaga ggaagtacgg atattaccat ccaaggaggc   2160
gatgacgtat ccaaagagaa ttacgttacg ctattgggta cctttgatga gtgctactta   2220
acgtatttat atcaaaaaat agatgagtcg aaattaaaag cctatacccg ttaccaatta   2280
agagggtata tcgaagatag tcaagactta gaaatctatt taattcgcta caatgccaaa   2340
cacgaaacag taaatgtgcc aggtacgggt tccttatggc cgctttcagc ccccaagtcca   2400
atcggaaaat gtgcccatca ttcccatcat ttctccttgg acattgatgt tggatgtaca   2460
gacttaaatg aggacttagg tgtatgggtg atattcaaga ttaagacgca agatggccat   2520
gcaagactag gaaatctaga atttctcgaa gagaaaccat tagtaggaga agcactagct   2580
cgtgtgaaaa gagcggagaa aaaatggaga gacaaacgtg aaaaattgga atgggaaaca   2640
```

```
aatattgttt ataaagaggc aaaagaatct gtagatgctt tatttgtaaa ctctcaatat   2700

gatagattac aagcggatac caacatcgcg atgattcatg cggcagataa acgcgttcat   2760

agcattcgag aagcttatct gcctgagctg tctgtgattc cgggtgtcaa tgcggctatt   2820

tttgaagaat tagaagggcg tattttcact gcattctccc tatatgatgc gagaaatgtc   2880

attaaaaatg gtgattttaa taatggctta tcctgctgga acgtgaaagg gcatgtagat   2940

gtagaagaac aaaacaacca ccgttcggtc cttgttgttc cggaatggga agcagaagtg   3000

tcacaagaag ttcgtgtctg tccgggtcgt ggctatatcc ttcgtgtcac agcgtacaag   3060

gagggatatg gagaaggttg cgtaaccatt catgagatcg agaacaatac agacgaactg   3120

aagtttagca actgtgtaga agaggaagta tatccaaaca acacggtaac gtgtaatgat   3180

tatactgcga ctcaagaaga atatgagggt acgtacactt ctcgtaatcg aggatatgac   3240

ggagcctatg aaagcaattc ttctgtacca gctgattatg catcagccta tgaagaaaaa   3300

gcatatacag atggacgaag agacaatcct tgtgaatcta acagaggata tggggattac   3360

acaccactac cagctggcta tgtgacaaaa gaattagagt acttcccaga aaccgataag   3420

gtatggattg agatcggaga aacggaagga acattcatcg tggacagcgt ggaattactt   3480

cttatggagg aataa                                                    3495
```

```
<210> SEQ ID NO 38
<211> LENGTH: 1164
<212> TYPE: PRT
<213> ORGANISM: Artificial Sequence
<220> FEATURE:
<223> OTHER INFORMATION: translated from synthesized coding region

<400> SEQUENCE: 38

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205
```

```
Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Phe Glu Ala Glu Ser
    610                 615                 620

Asp Leu Glu Arg Ala Gln Lys Ala Val Asn Ala Leu Phe Thr Ser Ser
```

```
625                 630                 635                 640

Asn Gln Ile Gly Leu Lys Thr Asp Val Thr Asp Tyr His Ile Asp Arg
                645                 650                 655

Val Ser Asn Leu Val Glu Cys Leu Ser Asp Glu Phe Cys Leu Asp Glu
            660                 665                 670

Lys Lys Glu Leu Ser Glu Lys Val Lys His Ala Lys Arg Leu Ser Asp
        675                 680                 685

Glu Arg Asn Leu Leu Gln Asp Pro Asn Phe Arg Gly Ile Asn Arg Gln
    690                 695                 700

Leu Asp Arg Gly Trp Arg Gly Ser Thr Asp Ile Thr Ile Gln Gly Gly
705                 710                 715                 720

Asp Asp Val Ser Lys Glu Asn Tyr Val Thr Leu Leu Gly Thr Phe Asp
                725                 730                 735

Glu Cys Tyr Leu Thr Tyr Leu Tyr Gln Lys Ile Asp Glu Ser Lys Leu
            740                 745                 750

Lys Ala Tyr Thr Arg Tyr Gln Leu Arg Gly Tyr Ile Glu Asp Ser Gln
        755                 760                 765

Asp Leu Glu Ile Tyr Leu Ile Arg Tyr Asn Ala Lys His Glu Thr Val
    770                 775                 780

Asn Val Pro Gly Thr Gly Ser Leu Trp Pro Leu Ser Ala Pro Ser Pro
785                 790                 795                 800

Ile Gly Lys Cys Ala His His Ser His His Phe Ser Leu Asp Ile Asp
                805                 810                 815

Val Gly Cys Thr Asp Leu Asn Glu Asp Leu Gly Val Trp Val Ile Phe
            820                 825                 830

Lys Ile Lys Thr Gln Asp Gly His Ala Arg Leu Gly Asn Leu Glu Phe
        835                 840                 845

Leu Glu Glu Lys Pro Leu Val Gly Glu Ala Leu Ala Arg Val Lys Arg
    850                 855                 860

Ala Glu Lys Lys Trp Arg Asp Lys Arg Glu Lys Leu Glu Trp Glu Thr
865                 870                 875                 880

Asn Ile Val Tyr Lys Glu Ala Lys Glu Ser Val Asp Ala Leu Phe Val
                885                 890                 895

Asn Ser Gln Tyr Asp Arg Leu Gln Ala Asp Thr Asn Ile Ala Met Ile
            900                 905                 910

His Ala Ala Asp Lys Arg Val His Ser Ile Arg Glu Ala Tyr Leu Pro
        915                 920                 925

Glu Leu Ser Val Ile Pro Gly Val Asn Ala Ala Ile Phe Glu Glu Leu
    930                 935                 940

Glu Gly Arg Ile Phe Thr Ala Phe Ser Leu Tyr Asp Ala Arg Asn Val
945                 950                 955                 960

Ile Lys Asn Gly Asp Phe Asn Asn Gly Leu Ser Cys Trp Asn Val Lys
                965                 970                 975

Gly His Val Asp Val Glu Glu Gln Asn Asn His Arg Ser Val Leu Val
            980                 985                 990

Val Pro Glu Trp Glu Ala Glu Val  Ser Gln Glu Val Arg  Val Cys Pro
        995                 1000                1005

Gly Arg  Gly Tyr Ile Leu Arg  Val Thr Ala Tyr Lys  Glu Gly Tyr
    1010                1015                1020

Gly Glu  Gly Cys Val Thr Ile  His Glu Ile Glu Asn  Asn Thr Asp
    1025                1030                1035

Glu Leu  Lys Phe Ser Asn Cys  Val Glu Glu Glu Val  Tyr Pro Asn
    1040                1045                1050
```

```
Asn Thr  Val Thr Cys Asn Asp  Tyr Thr Ala Thr Gln  Glu Glu Tyr
    1055                 1060                 1065

Glu Gly  Thr Tyr Thr Ser Arg  Asn Arg Gly Tyr Asp  Gly Ala Tyr
    1070                 1075                 1080

Glu Ser  Asn Ser Ser Val Pro  Ala Asp Tyr Ala Ser  Ala Tyr Glu
    1085                 1090                 1095

Glu Lys  Ala Tyr Thr Asp Gly  Arg Arg Asp Asn Pro  Cys Glu Ser
    1100                 1105                 1110

Asn Arg  Gly Tyr Gly Asp Tyr  Thr Pro Leu Pro Ala  Gly Tyr Val
    1115                 1120                 1125

Thr Lys  Glu Leu Glu Tyr Phe  Pro Glu Thr Asp Lys  Val Trp Ile
    1130                 1135                 1140

Glu Ile  Gly Glu Thr Glu Gly  Thr Phe Ile Val Asp  Ser Val Glu
    1145                 1150                 1155

Leu Leu  Leu Met Glu Glu
    1160
```

<210> SEQ ID NO 39
<211> LENGTH: 2109
<212> TYPE: DNA
<213> ORGANISM: Artificial Sequence
<220> FEATURE:
<223> OTHER INFORMATION: synthesized coding region

<400> SEQUENCE: 39

```
atggcacaga gcagtaggat ctgccacggt gtgcagaacc cgtgcgtgat catctcgaac     60

ctgagcaagt ccaaccagaa caagtcaccg ttctccgtgt ccctcaagac ccaccagcac    120

ccgagagcct acccgatcag cagctcctgg ggactgaaga agagtggcat gaccctgatc    180

ggctccgagc tgagaccgct gaaggtgatg tccagcgtgt cagcggataa caacccgaac    240

atcaacgagt gcatccccta caactgcctg agcaaccccg aggaggtgct gctggacggc    300

gagaggatct caaccggcaa cagcagcatc gacatcagcc tgtccctggt gcagttcctg    360

gtgagcaact tcgtgccggg cggcggcttc ctggtgggat taatcgactt cgtgtggggc    420

atcgtcggcc cgtcccagtg ggacgccttc ctggttcaga tcgagcaatt aattaatgaa    480

aggatagcag agttcgcgag gaacgcggcc atcgccaacc tggagggcct gggcaacaac    540

ttcaacatct acgtggaagc atttaaggag tgggaggagg accccaagaa cccggccacg    600

aggacgaggg tgatcgaccg ctttcgcatc ctggacggcc tgctggagag ggacatcccg    660

tccttcagaa tcagcggctt cgaggtcccg ctgctgtccg tgtacgcgca agcggccaac    720

ctgcacctgg cgatcctgag ggactccgtg atattcggcg agaggtgggg cctgaccacc    780

atcaacgtga atgaaaacta caaccggctg ataaggcaca tcgacgagta cgccgaccac    840

tgcgccaaca cctacaatag gggattaaat aatctgccca agagcaccta ccaagactgg    900

atcacatata accggctgag gagggacctg accctgaccg tgctggacat cgccgcgttc    960

ttcccgaact acgacaatag gcgctacccg atccagccgg tgggccagct gacccgcgag   1020

gtgtacaccg acccattaat taatttcaac ccgcagctcc agtccgtggc ccagctgccg   1080

accttcaacg tgatggagaa cagcgccatc cggaacccgc acctgttcga catcctgaat   1140

aatctgacca tcttcaccga ctggttctca gtgggccgga acttctactg ggggcggccat  1200

agggtgatct ccagcctgat cggcggcggc aacatcacct ccccgatcta cgggagggag   1260

gcgaaccagg agccgccgag gtccttcacc ttcaacggcc cggtgtttag gaccctgtcc   1320
```

```
aacccgaccc tgaggctgct ccagcagccg tggccggcgc cgccgttcaa cctgaggggc   1380

gtggagggcg tggagttcag caccccgacc aacagcttca cctaccgggg gaggggcacc   1440

gtggactcac tgaccgagct gccgccggag gacaacagcg tgccgccgag ggagggctac   1500

agccataggc tgtgccacgc caccttcgtg cagaggagcg gcaccccgtt cttgacgacc   1560

ggcgtggtgt tctcctggac ccaccggagc gcgaccctga ccaatacaat cgacccggag   1620

agaattaatc aaatcccgct ggtgaagggc ttccgggtgt ggggcggcac ctccgtgatc   1680

accgggccgg gctttaccgg cggcgacatc ctgaggagga acacgttcgg cgacttcgtg   1740

agcctccaag tgaacattaa tagcccgatc acccagcgct accggctgag gttccgctac   1800

gcgtcaagcc gcgacgcgag ggtgatcgtg ctgaccggcg cggcctcaac cggcgtgggc   1860

ggccaagtgt ccgtgaacat gccgctgcaa aagacgatgg agatcggcga gaacctgacc   1920

tcaaggacct tccgctacac cgacttcagc aacccgttca gctttagggc caacccggat   1980

ataatcggca tcagcgagca gccgctgttc ggcgccggct ccatctcaag cggcgagctg   2040

tacatcgata aaatcgagat catcctggcg gacgcgacct tggaggccga gtccgacctg   2100

gagaggtga                                                           2109
```

```
<210> SEQ ID NO 40
<211> LENGTH: 702
<212> TYPE: PRT
<213> ORGANISM: Artificial Sequence
<220> FEATURE:
<223> OTHER INFORMATION: translated from synthesized coding region

<400> SEQUENCE: 40

Met Ala Gln Ser Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
            20                  25                  30

Val Ser Leu Lys Thr His Gln His Pro Arg Ala Tyr Pro Ile Ser Ser
        35                  40                  45

Ser Trp Gly Leu Lys Lys Ser Gly Met Thr Leu Ile Gly Ser Glu Leu
    50                  55                  60

Arg Pro Leu Lys Val Met Ser Ser Val Ser Ala Asp Asn Asn Pro Asn
65                  70                  75                  80

Ile Asn Glu Cys Ile Pro Tyr Asn Cys Leu Ser Asn Pro Glu Glu Val
                85                  90                  95

Leu Leu Asp Gly Glu Arg Ile Ser Thr Gly Asn Ser Ser Ile Asp Ile
            100                 105                 110

Ser Leu Ser Leu Val Gln Phe Leu Val Ser Asn Phe Val Pro Gly Gly
        115                 120                 125

Gly Phe Leu Val Gly Leu Ile Asp Phe Val Trp Gly Ile Val Gly Pro
    130                 135                 140

Ser Gln Trp Asp Ala Phe Leu Val Gln Ile Glu Gln Leu Ile Asn Glu
145                 150                 155                 160

Arg Ile Ala Glu Phe Ala Arg Asn Ala Ala Ile Ala Asn Leu Glu Gly
                165                 170                 175

Leu Gly Asn Asn Phe Asn Ile Tyr Val Glu Ala Phe Lys Glu Trp Glu
            180                 185                 190

Glu Asp Pro Lys Asn Pro Ala Thr Arg Thr Arg Val Ile Asp Arg Phe
        195                 200                 205

Arg Ile Leu Asp Gly Leu Leu Glu Arg Asp Ile Pro Ser Phe Arg Ile
    210                 215                 220
```

```
Ser Gly Phe Glu Val Pro Leu Leu Ser Val Tyr Ala Gln Ala Ala Asn
225                 230                 235                 240

Leu His Leu Ala Ile Leu Arg Asp Ser Val Ile Phe Gly Glu Arg Trp
                245                 250                 255

Gly Leu Thr Thr Ile Asn Val Asn Glu Asn Tyr Asn Arg Leu Ile Arg
            260                 265                 270

His Ile Asp Glu Tyr Ala Asp His Cys Ala Asn Thr Tyr Asn Arg Gly
        275                 280                 285

Leu Asn Asn Leu Pro Lys Ser Thr Tyr Gln Asp Trp Ile Thr Tyr Asn
    290                 295                 300

Arg Leu Arg Arg Asp Leu Thr Leu Thr Val Leu Asp Ile Ala Ala Phe
305                 310                 315                 320

Phe Pro Asn Tyr Asp Asn Arg Arg Tyr Pro Ile Gln Pro Val Gly Gln
                325                 330                 335

Leu Thr Arg Glu Val Tyr Thr Asp Pro Leu Ile Asn Phe Asn Pro Gln
            340                 345                 350

Leu Gln Ser Val Ala Gln Leu Pro Thr Phe Asn Val Met Glu Asn Ser
        355                 360                 365

Ala Ile Arg Asn Pro His Leu Phe Asp Ile Leu Asn Asn Leu Thr Ile
    370                 375                 380

Phe Thr Asp Trp Phe Ser Val Gly Arg Asn Phe Tyr Trp Gly Gly His
385                 390                 395                 400

Arg Val Ile Ser Ser Leu Ile Gly Gly Gly Asn Ile Thr Ser Pro Ile
                405                 410                 415

Tyr Gly Arg Glu Ala Asn Gln Glu Pro Pro Arg Ser Phe Thr Phe Asn
            420                 425                 430

Gly Pro Val Phe Arg Thr Leu Ser Asn Pro Thr Leu Arg Leu Leu Gln
        435                 440                 445

Gln Pro Trp Pro Ala Pro Pro Phe Asn Leu Arg Gly Val Glu Gly Val
    450                 455                 460

Glu Phe Ser Thr Pro Thr Asn Ser Phe Thr Tyr Arg Gly Arg Gly Thr
465                 470                 475                 480

Val Asp Ser Leu Thr Glu Leu Pro Pro Glu Asp Asn Ser Val Pro Pro
                485                 490                 495

Arg Glu Gly Tyr Ser His Arg Leu Cys His Ala Thr Phe Val Gln Arg
            500                 505                 510

Ser Gly Thr Pro Phe Leu Thr Thr Gly Val Val Phe Ser Trp Thr His
        515                 520                 525

Arg Ser Ala Thr Leu Thr Asn Thr Ile Asp Pro Glu Arg Ile Asn Gln
    530                 535                 540

Ile Pro Leu Val Lys Gly Phe Arg Val Trp Gly Gly Thr Ser Val Ile
545                 550                 555                 560

Thr Gly Pro Gly Phe Thr Gly Gly Asp Ile Leu Arg Arg Asn Thr Phe
                565                 570                 575

Gly Asp Phe Val Ser Leu Gln Val Asn Ile Asn Ser Pro Ile Thr Gln
            580                 585                 590

Arg Tyr Arg Leu Arg Phe Arg Tyr Ala Ser Ser Arg Asp Ala Arg Val
        595                 600                 605

Ile Val Leu Thr Gly Ala Ala Ser Thr Gly Val Gly Gly Gln Val Ser
    610                 615                 620

Val Asn Met Pro Leu Gln Lys Thr Met Glu Ile Gly Glu Asn Leu Thr
625                 630                 635                 640
```

-continued

```
Ser Arg Thr Phe Arg Tyr Thr Asp Phe Ser Asn Pro Phe Ser Phe Arg
                645                 650                 655

Ala Asn Pro Asp Ile Ile Gly Ile Ser Glu Gln Pro Leu Phe Gly Ala
            660                 665                 670

Gly Ser Ile Ser Ser Gly Glu Leu Tyr Ile Asp Lys Ile Glu Ile Ile
        675                 680                 685

Leu Ala Asp Ala Thr Leu Glu Ala Glu Ser Asp Leu Glu Arg
    690                 695                 700
```